(12) United States Patent
Murakami et al.

(10) Patent No.: US 11,006,844 B2
(45) Date of Patent: May 18, 2021

(54) PULSE WAVE MEASURING DEVICE, PULSE WAVE MEASURING METHOD, AND RECORDING MEDIUM

(71) Applicant: Panasonic Intellectual Property Management Co., Ltd., Osaka (JP)

(72) Inventors: Kenta Murakami, Osaka (JP); Mototaka Yoshioka, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 947 days.

(21) Appl. No.: 15/666,854

(22) Filed: Aug. 2, 2017

(65) Prior Publication Data
US 2018/0055391 A1 Mar. 1, 2018

(30) Foreign Application Priority Data

Aug. 26, 2016 (JP) .............................. JP2016-166278
Apr. 20, 2017 (JP) .............................. JP2017-083759

(51) Int. Cl.
*A61B 5/024* (2006.01)
*G06T 7/00* (2017.01)
(Continued)

(52) U.S. Cl.
CPC ........ *A61B 5/02433* (2013.01); *A61B 5/0013* (2013.01); *A61B 5/0255* (2013.01);
(Continued)

(58) Field of Classification Search
CPC ...... A61B 2562/0233; A61B 2562/063; A61B 2576/00; A61B 5/0013; A61B 5/02125;
(Continued)

(56) References Cited

U.S. PATENT DOCUMENTS

| 2007/0118026 | A1 | 5/2007 | Kameyama et al. |
| 2009/0141124 | A1* | 6/2009 | Liu ........................ A61B 5/489 348/65 |

(Continued)

FOREIGN PATENT DOCUMENTS

| JP | 2004-146873 | 5/2004 |
| JP | 2007-130182 | 5/2007 |

(Continued)

*Primary Examiner* — Amanda Lauritzen Moher
(74) *Attorney, Agent, or Firm* — Wenderoth, Lind & Ponack, L.L.P.

(57) ABSTRACT

A pulse wave measuring device includes a processor and a memory. The processor obtains a visible light image, in a visible light wavelength range, of a user irradiated with visible light by a visible light source, obtains an infrared light image, in an infrared light wavelength range, of the user irradiated with infrared light by an infrared light source, extracts a visible light wave indicative of a user's pulse wave from the visible light image, extracts an infrared light wave indicative of a user's pulse wave from the infrared light image, computes a correlation value between the visible and infrared light waves, supplies a control signal for controlling the amount of infrared light emitted from the infrared light source to the infrared light source in accordance with the correlation value, calculates biological information by using at least one of the visible and infrared light waves, and outputs the biological information.

15 Claims, 24 Drawing Sheets

(51) Int. Cl.
*G06K 9/00* (2006.01)
*A61B 5/0255* (2006.01)
*A61B 5/00* (2006.01)
*G06K 9/20* (2006.01)
*H04N 5/33* (2006.01)
*H04N 5/225* (2006.01)
*A61B 5/021* (2006.01)

(52) U.S. Cl.
CPC ........ *A61B 5/02416* (2013.01); *A61B 5/4812* (2013.01); *A61B 5/6889* (2013.01); *A61B 5/6891* (2013.01); *A61B 5/7225* (2013.01); *A61B 5/7278* (2013.01); *G06K 9/0053* (2013.01); *G06K 9/2018* (2013.01); *G06T 7/0016* (2013.01); *H04N 5/332* (2013.01); *A61B 5/02125* (2013.01); *A61B 5/7246* (2013.01); *A61B 5/742* (2013.01); *A61B 2562/0233* (2013.01); *A61B 2562/063* (2013.01); *A61B 2576/00* (2013.01); *G06K 2209/05* (2013.01); *G06T 2207/30101* (2013.01); *H04N 5/2256* (2013.01)

(58) Field of Classification Search
CPC ............ A61B 5/02416; A61B 5/02433; A61B 5/0255; A61B 5/4812; A61B 5/6889; A61B 5/6891; A61B 5/7225; A61B 5/7246; A61B 5/7278; A61B 5/742; G06K 2209/05; G06K 9/0053; G06K 9/2018; G06T 2207/30101; G06T 7/0016; G16H 30/40; H04N 5/2256; H04N 5/332
See application file for complete search history.

(56) References Cited

U.S. PATENT DOCUMENTS

| | | | |
|---|---|---|---|
| 2013/0245465 A1 | 9/2013 | Kasama | |
| 2014/0316293 A1* | 10/2014 | Ahmad | A61B 5/725 |
| | | | 600/508 |
| 2015/0257659 A1* | 9/2015 | Broers | A61B 5/748 |
| | | | 600/473 |
| 2016/0100766 A1 | 4/2016 | Yoshioka et al. | |

FOREIGN PATENT DOCUMENTS

| | | | | |
|---|---|---|---|---|
| JP | 2007-151579 | 6/2007 | | |
| JP | 2011-019973 | 2/2011 | | |
| JP | 2013-192620 | 9/2013 | | |
| JP | 2016-077890 | 5/2016 | | |
| JP | 2018038553 | * | 3/2018 | ............... A61B 5/02 |

* cited by examiner

FIG. 13
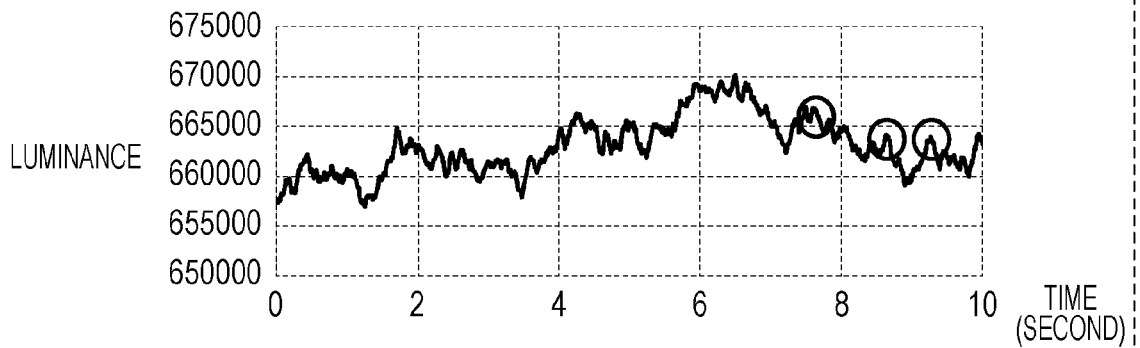
(a) LIGHT SOURCE LEVEL 1
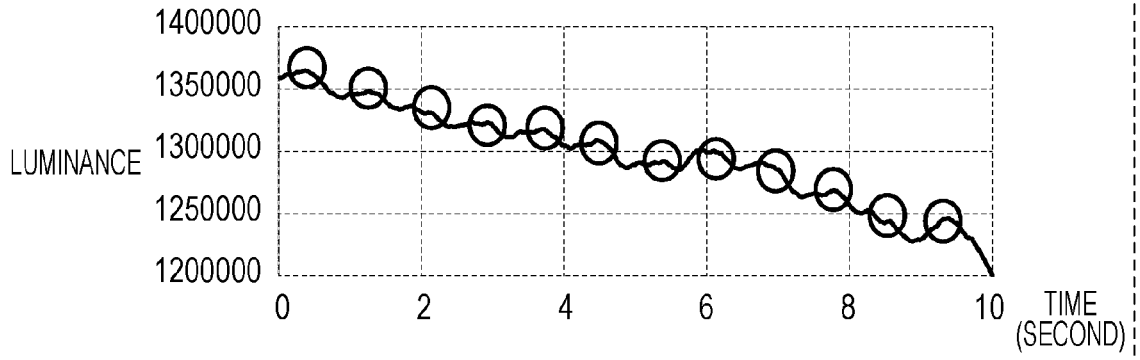
(b) LIGHT SOURCE LEVEL 2
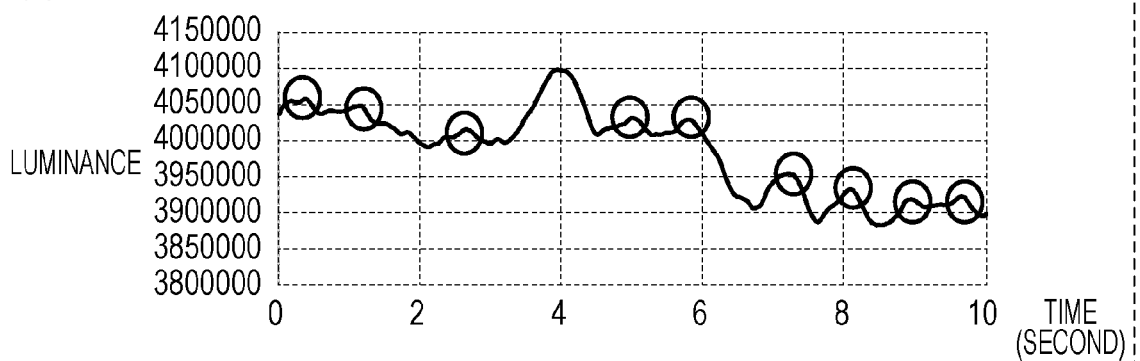
(c) LIGHT SOURCE LEVEL 3
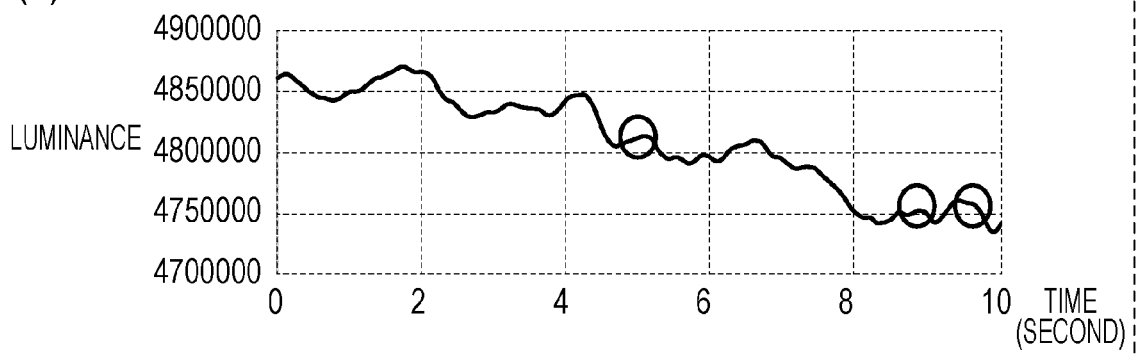
(d) LIGHT SOURCE LEVEL 4

PULSE WAVE MEASURING DEVICE, PULSE WAVE MEASURING METHOD, AND RECORDING MEDIUM

BACKGROUND

1. Technical Field

The present disclosure relates to a pulse wave measuring device that measures a pulse wave of a person in a non-contact manner, a pulse wave measuring method, and a recording medium.

2. Description of the Related Art

Japanese Unexamined Patent Application Publication No. 2013-192620 discloses a technique for measuring a heartbeat and a sleep stage in a non-contact manner, for example, by using a millimeter-wave, visible light, or infrared light.

Japanese Unexamined Patent Application Publication No. 2004-146873 discloses a technique for switching a mode of an imaging device from an infrared imaging mode in which a subject is irradiated with infrared light to a normal imaging mode well.

However, the techniques disclosed in Japanese Unexamined Patent Application Publication No. 2013-192620 and Japanese Unexamined Patent Application Publication No. 2004-146873 need further improvements.

SUMMARY

In one general aspect, the techniques disclosed here feature a pulse wave measuring device including: a processor; and a memory, wherein the processor performs processes including: obtaining a first visible light image, in a visible light wavelength range, of a user irradiated with visible light by a visible light source, obtaining a first infrared light image, in an infrared light wavelength range, of the user irradiated with infrared light by an infrared light source, extracting a first visible light wave that is a wave indicative of a pulse wave of the user from the obtained first visible light image, extracting a first infrared light wave that is a wave indicative of a pulse wave of the user from the obtained first infrared light image, computing a first correlation value between the extracted first visible light wave and the extracted first infrared light wave, performing a first determining process for determining whether or not the computed first correlation value is equal to or larger than a second threshold value, supplying a first control signal for decreasing a light amount of the visible light emitted from the visible light source to the visible light source and supplying a second control signal for increasing a light amount of the infrared light emitted from the infrared light source to the infrared light source in a case where the processor determines, as a result of the first determining process, that the computed first correlation value is equal to or larger than the second threshold value, obtaining a second visible light image, in the visible light wavelength range, of the user irradiated with visible light based on the first control signal by the visible light source, obtaining a second infrared light image, in the infrared light wavelength range, of the user irradiated with infrared light based on the second control signal by the infrared light source, extracting a second visible light wave that is a wave indicative of a pulse wave of the user from the obtained second visible light image, extracting a second infrared light wave that is a wave indicative of a pulse wave of the user from the obtained second infrared light image, calculating biological information by using at least one of the extracted second visible light wave and second infrared light wave, and outputting the calculated biological information.

According to the present disclosure, further improvements can be achieved.

It should be noted that general or specific embodiments may be implemented as a system, a method, an integrated circuit, a computer program, a computer-readable storage medium, or any selective combination thereof. Examples of the computer-readable storage medium include a non-volatile storage medium such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 13 is a graph illustrating infrared light waves obtained in a case where a human skin image is obtained by using an infrared light camera at different levels of the light amount of the infrared light source;

DETAILED DESCRIPTION

Figure 1:
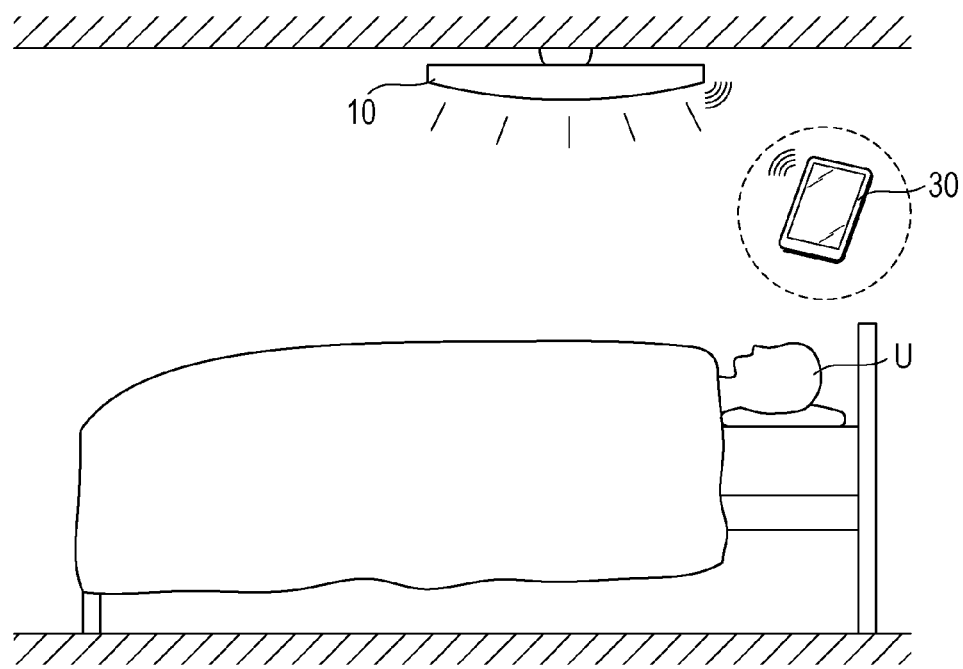
FIG. 1 is a schematic view illustrating a state where a pulse wave measuring device according to the present embodiment is used by a user.

Underlying Knowledge Forming Basis of the Present Disclosure

The inventor of the present invention found that the following problems occur in the techniques described in BACKGROUND.

Japanese Unexamined Patent Application Publication No. 2013-192620 does not disclose adjustment of a light amount of an infrared light source in a case where a pulse wave is obtained in a dark room. It is therefore undesirably difficult to measure a heartbeat and a pulse wave in a dark room in a non-contact manner.

Japanese Unexamined Patent Application Publication No. 2004-146873, in which the mode is switched by using a ratio of luminance of visible light and luminance of infrared light, it is undesirably not easy to measure a pulse wave in a case where this mode switching using the ratio of luminance is applied to pulse wave measurement in a dark room.

In view of the circumstances, the present disclosure provides a pulse wave measuring device and the like that are capable of precisely measuring a pulse wave in a dark room.

A pulse wave measuring device according to one aspect of the present disclosure is a pulse wave measuring device including: a processor; and a memory, wherein the processor performs processes including: obtaining a first visible light image, in a visible light wavelength range, of a user irradiated with visible light by a visible light source, obtaining a first infrared light image, in an infrared light wavelength range, of the user irradiated with infrared light by an infrared light source, extracting a first visible light wave that is a wave indicative of a pulse wave of the user from the obtained first visible light image, extracting a first infrared light wave that is a wave indicative of a pulse wave of the user from the obtained first infrared light image, computing a first correlation value between the extracted first visible light wave and the extracted first infrared light wave, performing a first determining process for determining whether or not the computed first correlation value is equal to or larger than a second threshold value, supplying a first control signal for decreasing a light amount of the visible light emitted from the visible light source to the visible light source and supplying a second control signal for increasing a light amount of the infrared light emitted from the infrared light source to the infrared light source in a case where the processor determines, as a result of the first determining process, that the computed first correlation value is equal to or larger than the second threshold value, obtaining a second visible light image, in the visible light wavelength range, of the user irradiated with visible light based on the first control signal by the visible light source, obtaining a second infrared light image, in the infrared light wavelength range, of the user irradiated with infrared light based on the second control signal by the infrared light source, extracting a second visible light wave that is a wave indicative of a pulse wave of the user from the obtained second visible light image, extracting a second infrared light wave that is a wave indicative of a pulse wave of the user from the obtained second infrared light image, calculating biological information by using at least one of the extracted second visible light wave and second infrared light wave, and outputting the calculated biological information.

With this configuration, a first correlation value between a first visible light wave obtained from a first visible light image capturing a user's pulse wave and a first infrared light wave obtained from a first infrared light image capturing the same pulse wave is computed, and the light amount of infrared light emitted from an infrared light source is controlled in accordance with the first correlation value. It is therefore possible to properly adjust the light amount of infrared light, thereby making it possible to precisely calculate biological information.

The pulse wave measuring device may be, for example, configured such that in the computing the first correlation value, the processor performs processes including: extracting a plurality of first peak points from the first visible light wave by dividing the first visible light wave into a plurality of first unit waves on a basis of a pulse wave cycle that is a cycle of the pulse wave and then extracting, for each of the plurality of first unit waves, a first peak point that is a first top point indicative of a maximum value of the first unit wave or a first bottom point indicative of a minimum value of the first unit wave, extracting a plurality of second peak points from the first infrared light wave by dividing the first infrared light wave into a plurality of second unit waves on a basis of the pulse wave cycle and then extracting, for each of the plurality of second unit waves, a second peak point that is a second top point indicative of a maximum value of the second unit wave or a second bottom point indicative of a minimum value of the second unit wave, calculating a plurality of first heartbeat time intervals by calculating, for each of the plurality of extracted first peak points, a first heartbeat time interval that is a time interval between a first time point of the first peak point and a second time point of another first peak point that is adjacent, in a time sequence, to the first peak point, calculating a plurality of second heartbeat time intervals by calculating, for each of the plurality of extracted second peak points, a second heartbeat time interval that is a time interval between a third time point of the second peak point and a fourth time point of another second peak point that is adjacent, in a time sequence, to the second peak point, and computing, as the first correlation value, a first correlation coefficient between the plurality of first heartbeat time intervals and the plurality of second heartbeat time intervals that correspond to each other in a time sequence by using an equation 1:

$$\rho 1 = \frac{\sigma_{12}}{\sigma_1 \sigma_2}$$

where $\rho 1$ is the first correlation value, $\sigma_{12}$ is a covariance of the plurality of first heartbeat time intervals and the plurality of second heartbeat time intervals, $\sigma_1$ is a first standard deviation that is a standard deviation of the plurality of first heartbeat time intervals, and $\sigma_2$ is a second standard deviation that is a standard deviation of the plurality of second heartbeat time intervals.

With this configuration, a first correlation coefficient is computed as a first correlation value by comparing first heartbeat time intervals calculated from a first visible light wave and second heartbeat time intervals calculated from a first infrared light wave. It is therefore possible to easily compute the first correlation value between the first visible light wave and the first infrared light wave.

The pulse wave measuring device may be, for example, configured such that the processor further performs processes including: performing a second determining process for determining whether or not the first standard deviation is larger than a fourth threshold value and the second standard deviation is larger than the fourth threshold value, performing a third determining process and a fourth determining process in a case where the processor determines, as a result of the second determining process, that the first standard deviation is larger than the fourth threshold value and the second standard deviation is larger than the fourth threshold value, the third determining process being a process for determining whether or not a first time difference between one of the plurality of first heartbeat time intervals and one of the plurality of second heartbeat time intervals that corresponds to the one first heartbeat time interval in a time sequence is smaller than a fifth threshold value, and the fourth determining process being a process for determining whether or not the first time difference is larger than a sixth threshold value that is larger than the fifth threshold value, supplying the second control signal to the infrared light source in a case where the processor determines, as a result of the third determining process and the fourth determining process, that the first time difference is larger than the sixth threshold value, and supplying a third control signal for increasing the light amount of the visible light emitted from the visible light source to the visible light source and supplying a fourth control signal for decreasing the light amount of the infrared light emitted from the infrared light source to the infrared light source in a case where the processor determines, as a result of the third determining process and the fourth determining process, that the first time difference is not less than the fifth threshold value and not more than the sixth threshold value.

The pulse wave measuring device may be, for example, configured such that the processor further performs processes including: performing a fifth determining process for determining whether or not the second standard deviation is equal to or smaller than the fourth threshold value in a case where the processor determines, as a result of the third determining process and the fourth determining process, that the first time difference is smaller than the fifth threshold value, supplying the first control signal to the visible light source and supplying the second control signal to the infrared light source in a case where the processor determines, as a result of the fifth determining process, that the second standard deviation is equal to or smaller than the fourth threshold value, and supplying the third control signal to the visible light source and supplying the fourth control signal to the infrared light source in a case where the processor determines, as a result of the fifth determining process, that the second standard deviation is larger than the fourth threshold value.

With the configuration, it is possible to properly adjust the light amount of the visible light source and the light amount of the infrared light source.

The pulse wave measuring device may be, for example, configured such that the processor further performs processes including: storing, as a first slope in the memory, a slope of a first straight line connecting one of the plurality of first top points and one of the plurality of first bottom points that immediately follows, in a time sequence, the one first top point, extracting a plurality of third peak points from the second visible light wave by dividing the second visible light wave into a plurality of third unit waves on a basis of the pulse wave cycle and then extracting, for each of the plurality of third unit waves, a third peak point that is a third top point indicative of a maximum value of the third unit wave and a third bottom point indicative of a minimum value of the third unit wave, extracting a plurality of fourth peak points from the second infrared light wave by dividing the second infrared light wave into a plurality of fourth unit waves on a basis of the pulse wave cycle and then extracting, for each of the plurality of fourth unit waves, a fourth peak point that is a fourth top point indicative of a maximum value of the fourth unit wave or a fourth bottom point indicative of a minimum value of the fourth unit wave, calculating a plurality of third heartbeat time intervals by calculating, for each of the plurality of extracted third peak points, a third heartbeat time interval that is a time interval between a fifth time point of the third peak point and a sixth time point of another third peak point that is adjacent, in a time sequence, to the third peak point, calculating a plurality of fourth heartbeat time intervals by calculating, for each of the plurality of extracted fourth peak points, a fourth heartbeat time interval that is a time interval between a seventh time point of the fourth peak point and an eighth time point of another fourth peak point that is adjacent, in a time sequence, to the fourth peak point; computing a second correlation coefficient between the plurality of third heartbeat time intervals and the plurality of fourth heartbeat time intervals that correspond to each other in a time sequence by using an equation 2:

$$\rho 2 = \frac{\sigma_{34}}{\sigma_3 \sigma_4}$$

where $\rho 2$ is the second correlation coefficient, $\sigma_{34}$ is a covariance of the plurality of third heartbeat time intervals and the plurality of fourth heartbeat time intervals, $\sigma_3$ is a third standard deviation that is a standard deviation of the plurality of third heartbeat time intervals, and $\sigma_4$ is a fourth standard deviation that is a standard deviation of the plurality of fourth heartbeat time intervals, repeatedly obtaining the second visible light image, extracting the second visible light wave, obtaining the second infrared light image, extracting the second infrared light wave, and computing the second correlation coefficient, in the repeated computing the second correlation coefficient, comparing, with the first slope stored in the memory, a second slope that is a slope of a second straight line connecting one of the plurality of fourth top points and one of the plurality of fourth bottom points that immediately follows, in a time sequence, the one fourth top point in the second infrared light wave thus repeatedly obtained, and supplying the second control signal to the infrared light source until the second slope becomes the first slope.

With the configuration, the second slope in the second infrared light wave after adjustment of the light amount of the infrared light source and the first slope stored in the memory are compared. It is therefore possible to effectively determine whether or not the light amount of the infrared light source has become a proper light amount.

The pulse wave measuring device may be, for example, configured such that the processor further performs processing including: performing a sixth determining process for determining whether or not the third standard deviation is larger than the fourth threshold value and the fourth standard deviation is larger than the fourth threshold value, performing a seventh determining process and an eighth determining process in a case where the processor determines, as a result of the sixth determining process, that the third standard deviation is larger than the fourth threshold value and the fourth standard deviation is larger than the fourth threshold value, the seventh determining process being a process for determining whether or not a second time difference between one of the plurality of third heartbeat time intervals and one of the plurality of fourth heartbeat time intervals that corresponds, in a time sequence, to the one third heartbeat time interval is smaller than the fifth threshold value, and the eighth determining process being a process for determining whether or not the second time difference is larger than the sixth threshold value, supplying the second control signal to the infrared light source in a case where the processor determines, as a result of the seventh determining process and the eighth determining process, that the second time difference is larger than the sixth threshold value, and supplying the third control signal to the visible light source and supplying the fourth control signal to the infrared light source in a case where the processor determines, as a result of the seventh determining process and the eighth determining process, that the second time difference is not less than the fifth threshold value and not more than the sixth threshold value.

The pulse wave measuring device may be, for example, configured such that the processor further performs processes including: performing a ninth determining process for determining whether or not the fourth standard deviation is equal to or smaller than the fourth threshold value in a case where the processor determines, as a result of the seventh determining process and the eighth determining process, that the second time difference is smaller than the fifth threshold value; supplying the first control signal to the visible light source and supplying the second control signal to the infrared light source in a case where the processor determines, as a result of the ninth determining process, that the fourth standard deviation is equal to or smaller than the fourth threshold value, and supplying the third control signal to the visible light source and supplying the fourth control signal to the infrared light source in a case where the processor determines, as a result of the ninth determining process, that the fourth standard deviation is larger than the fourth threshold value.

The pulse wave measuring device may be, for example, configured such that in the repeated computing the second correlation coefficient, the processor performs a tenth determining process for determining whether or not the number of third peak points or the number of fourth peak points within a first predetermined period is larger than a first threshold value; in a case where the processor determines, as a result of the tenth determining process, that the number of third peak points or the number of fourth peak points within the first predetermined period is larger than the first threshold value, the processor performs processes including: extracting a plurality of first inflection points by extracting, for each of the plurality of third top points, a first inflection point that is an inflection point between the third top point and a third bottom point that immediately follows, in a time sequence, the third top point among the plurality of third bottom points, extracting a plurality of second inflection points by extracting, for each of the plurality of fourth top points, a second inflection point that is an inflection point between the fourth top point and a fourth bottom point that immediately follows, in a time sequence, the fourth top point among the plurality of fourth bottom points, calculating, as the third heartbeat time interval, for each of the plurality of extracted first inflection points, a time interval between a ninth time point of the first inflection point and a tenth time point of another first inflection point adjacent to the first inflection point, calculating, as the fourth heartbeat time interval, for each of the plurality of extracted second inflection points, a time interval between an eleventh time point of the second inflection point and a twelfth time point of another second inflection point adjacent to the second inflection point, and computing, as the second correlation coefficient, a correlation coefficient between (i) the plurality of third heartbeat time intervals, calculated by using the first inflection points, and (ii) the plurality of fourth heartbeat time intervals, calculated by using the second inflection points interval, that correspond to each other in a time sequence by using the equation 2.

With the configuration, it is possible to calculate each heartbeat time interval by using inflection points in a case where a large number of peak points are obtained.

The pulse wave measuring device may be, for example, configured such that in a case where an absolute error between the third heartbeat time interval and the fourth heartbeat time interval that correspond to each other in a time sequence among the third heartbeat time intervals and the fourth heartbeat time intervals is larger than a third threshold value, the processor further performs processes including: comparing the number of third peak points and the number of fourth peak points, specifying which of the third heartbeat time interval and the fourth heartbeat time interval for which the absolute error is larger than the third threshold value is a heartbeat time interval computed by a peak point included in peak points that have been determined to be smaller in number as a result of the comparing, and excluding the peak point used for computation of the specified heartbeat time interval from computation of the specified heartbeat time interval.

With the configuration, it is possible to delete an excessive peak point, thereby making it possible to obtain proper third heartbeat time intervals or fourth heartbeat time intervals.

The pulse wave measuring device may be, for example, configured such that the processor further performs processes including: comparing the number of third peak points and the number of fourth peak points, and specifying which of the plurality of third heartbeat time intervals and the plurality of fourth heartbeat time intervals are heartbeat time intervals computed by peak points that have been determined to be smaller in number as a result of the comparing; and in a case where a standard deviation of the specified heartbeat time intervals is equal to or smaller than the fourth threshold value, the processor performs processes including: extracting a plurality of first inflection points by extracting, for each of the plurality of third top points, a first inflection point that is an inflection point between the third top point and a third bottom point that immediately follows, in a time sequence, the third top point among the plurality of third bottom points, extracting a plurality of second inflection points by extracting, for each of the plurality of fourth top points, a second inflection point that is an inflection point between the fourth top point and a fourth bottom point that immediately follows, in a time sequence, the fourth top point among the plurality of fourth bottom points, calculating, as the third heartbeat time interval, for each of the plurality of extracted first inflection points, a time interval between a thirteenth time point of the first inflection point and a fourteenth time point of another first inflection point adjacent to the first inflection point, calculating, as the fourth heartbeat time interval, for each of the plurality of extracted second inflection points, a time interval between a fifteenth time point of the second inflection point and a sixteenth time point of another second inflection point adjacent to the second inflection point, and calculating, as the second correlation coefficient, a correlation coefficient between (i) the plurality of third heartbeat time intervals, calculated by using the first inflection points, and (ii) the plurality of fourth heartbeat time intervals, calculated by using the second inflection points, that correspond to each other in a time sequence by using the equation 2.

With the configuration, it is possible to properly adjust the light amount of the visible light source and the light amount of the infrared light source.

The pulse wave measuring device may be, for example, configured such that in the extracting the plurality of first peak points, the processor extracts the plurality of first peak points from the first visible light wave obtained during a period other than a period in which the light amount of the visible light source is controlled by the first control signal; in the extracting the plurality of second peak points, the processor extracts the plurality of second peak points from the first infrared light wave obtained during a period other than a period in which the light amount of the infrared light source is controlled by the second control signal; in the extracting the plurality of third peak points, the processor extracts the plurality of third peak points from the second visible light wave obtained during a period other than a period in which the light amount of the visible light source is controlled by the third control signal; and in the extracting the plurality of fourth peak points, the processor extracts the plurality of fourth peak points from the second infrared light wave obtained during a period other than a period in which the light amount of the infrared light source is controlled by the fourth control signal.

With the configuration, it is possible to properly extract the first through fourth peak points, thereby making it possible to precisely calculate biological information.

The pulse wave measuring device may be, for example, configured such that in the supplying the first control signal or the third control signal, the processor suspends supply of the first control signal or the third control signal until successive two or more first peak points are extracted within a second predetermined period from the first visible light wave or until successive two or more third peak points are extracted within the second predetermined period from the second visible light wave; and in the supplying the second control signal or the fourth control signal, the processor suspends supply of the second control signal or the fourth control signal until successive two or more second peak points are extracted within the second predetermined period from the first infrared light wave or until successive two or more fourth peak points are extracted within the second predetermined period from the second infrared light wave.

With the configuration, it is possible to properly extract the first through fourth peak points, thereby making it possible to precisely calculate biological information.

A pulse wave measuring method according to one aspect of the present disclosure a pulse wave measuring method including: obtaining first visible light images, in a visible light wavelength range, of a user irradiated with first visible light by a visible light source; obtaining first infrared light images, in an infrared light wavelength range, of the user irradiated with first infrared light by an infrared light source; extracting a first visible light wave from the first visible light images; extracting a first infrared light wave from the first infrared light images; computing a correlation value between the first visible light wave and the first infrared light wave; causing, when the correlation value is equal to or larger than a threshold value, (i) the visible light source to emit second visible light, an amount per unit time of the second visible light being smaller than an amount per unit time of the first visible light and (ii) the infrared light source to emit second infrared light, an amount per unit time of the second infrared light being larger than an amount per unit time of the first infrared light; obtaining second visible light images, in the visible light wavelength range, of the user irradiated with the second visible light; obtaining second infrared light images, in the infrared light wavelength range, of the user irradiated with the second infrared light; extracting a second visible light wave from the second visible light images; extracting a second infrared light wave from the second infrared light images; calculating biological information by using at least one of the second visible light wave and the second infrared light wave; and outputting the biological information, wherein the computation of the correlation value includes: extracting first peak points at first times included in first unit waves, the first peak points being either first maximum points included in the first unit waves or first minimum points included in the first unit waves, the first visible light wave including the first unit waves, the first maximum points corresponding to the first unit waves, respectively, the first minimum points corresponding to the first unit waves, respectively, and the first unit waves corresponding to the first times, respectively, extracting second peak points at second times included in second unit waves, the second peak points being either second maximum points included in the second unit waves or second minimum points included in the second unit waves, the first infrared light wave including the second unit waves, the second maximum points corresponding to the second unit waves, respectively, the second minimum points corresponding to the second unit waves, respectively, and the second unit waves corresponding to the second times, respectively, calculating first heartbeat time intervals on a basis of the first times, each of the first heartbeat time intervals being a time interval between a first time and a second time, the first time and the second time being included in the first times, none of times included in the first times being provided between the first time and the second time, calculating second heartbeat time intervals on a basis of the second times, each of the second heartbeat time intervals being a time interval between a third time and a fourth time, the third time and the fourth time being included in the second times, none of times included in the second times being provided between the third time and the fourth time, and calculating the correlation value using an equation 1:

$$\rho 1 = \frac{\sigma_{12}}{\sigma_1 \sigma_2}$$

where $\rho 1$ is the correlation value, $\sigma_{12}$ is a covariance of the first heartbeat time intervals and the second heartbeat time intervals, $\sigma 1$ is a first standard deviation that is a standard deviation of the first heartbeat time intervals, and $\rho 2$ is a second standard deviation that is a standard deviation of the second heartbeat time intervals.

It should be noted that general or specific embodiments may be implemented as a system, a method, an integrated circuit, a computer program, a computer-readable storage medium such as a CD-ROM, or any selective combination thereof. Embodiment In the present embodiment, a pulse wave measuring device that obtains user's pulse waves from a visible light image of the user and an infrared light image of the user, respectively and controls a light source on the basis of a correlation value between features of the two pulse waves thus obtained is described.

1-1. Configuration
1-1-1. Pulse Wave Measuring Device

A configuration of a pulse wave measuring device according to the present embodiment is described below.

Figure 2:
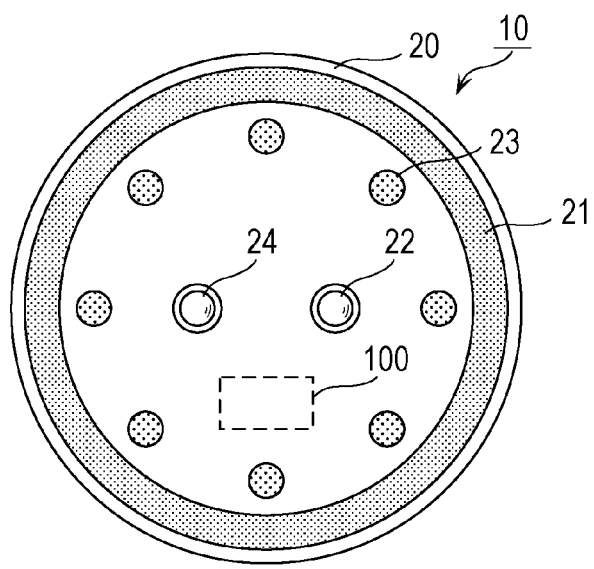
FIG. 2 is a plan view of the pulse wave measuring device viewed from below.
Figure 3:
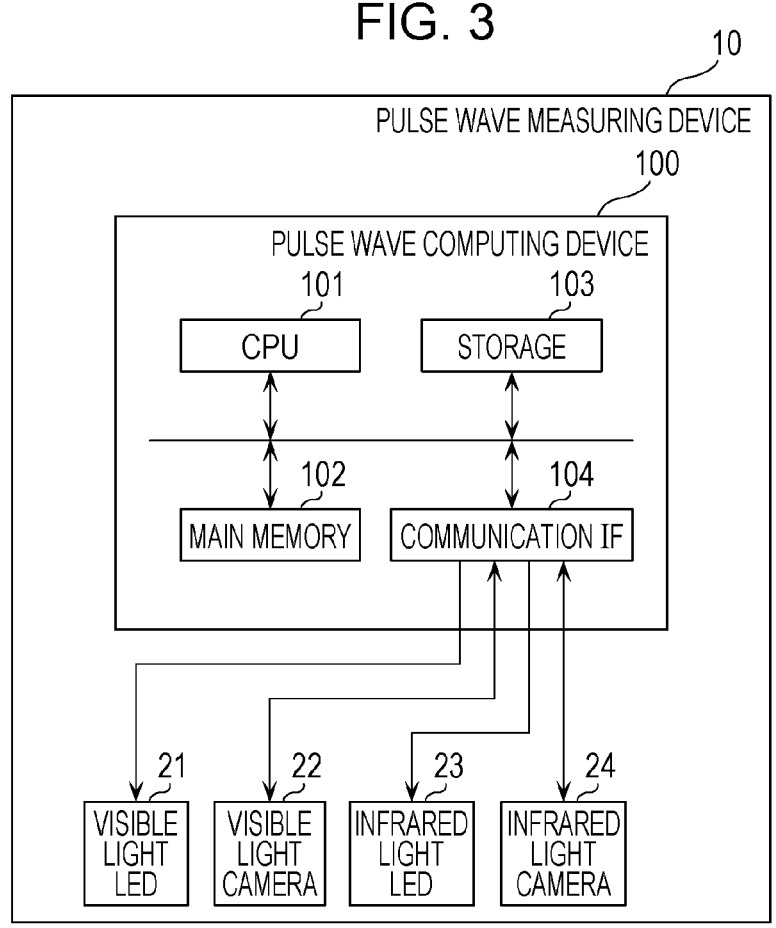
FIG. 3 is a block diagram illustrating a hardware configuration of the pulse wave measuring device.

FIG. 1 is a schematic view illustrating a state where a pulse wave measuring device 10 according to the present embodiment is used by a user U. FIG. 2 is a plan view of the pulse wave measuring device 10 viewed from below. FIG. 3 is a block diagram illustrating an example of a hardware configuration of the pulse wave measuring device 10.

Figure 5:
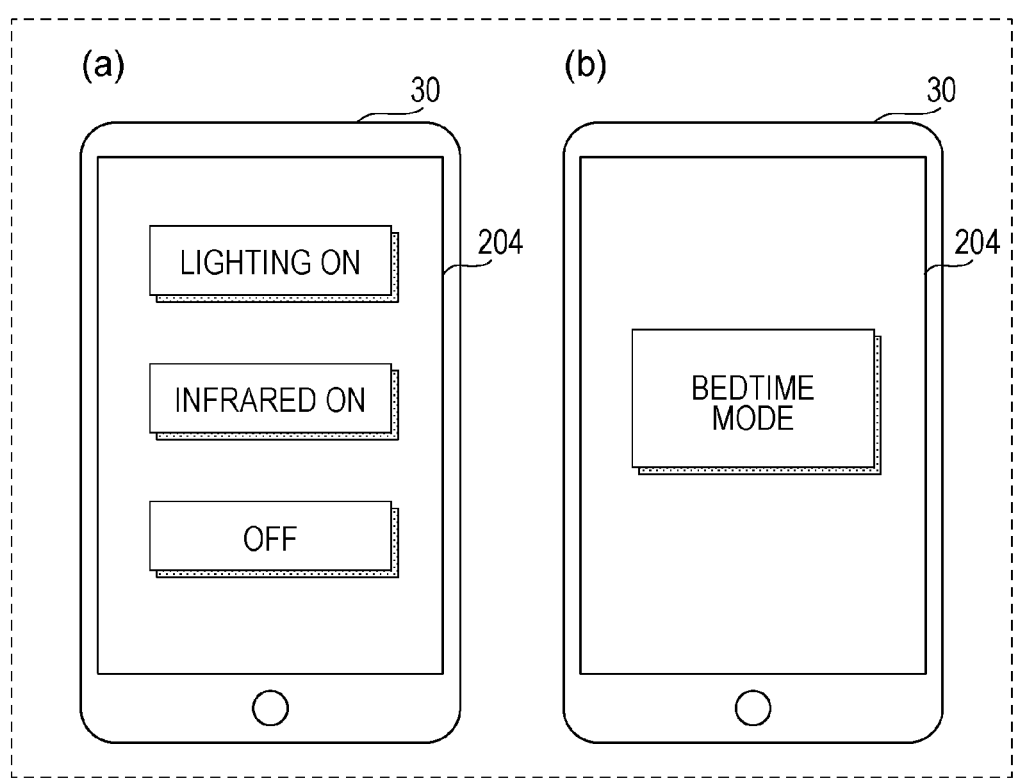
FIG. 5 is a diagram for explaining an example of use of the pulse wave measuring device.

FIG. 5 illustrates an example of a UI for operation of the pulse wave measuring device 10 that is displayed on a mobile terminal 30.

The pulse wave measuring device 10 includes a visible light LED 21, a visible light camera 22, an infrared light LED 23, and an infrared light camera 24. The pulse wave measuring device 10 may include a pulse wave computing device 100.

As illustrated in FIG. 2, the pulse wave measuring device 10 has a housing 20, and the constituent elements illustrated in FIG. 3 are disposed on a surface (e.g., a lower surface) of the housing 20 from which light is emitted. Specifically, the pulse wave measuring device 10 has, on the lower surface of the housing 20, the visible light LED (light emitting diode) 21, the visible light camera 22, the infrared light LED 23, and the infrared light camera 24. Furthermore, the pulse wave measuring device 10 includes the pulse wave computing device 100 that obtains user's pulse waves by using an image taken by the visible light camera 22 and an image taken by the infrared light camera 24 and controls a light amount of the visible light LED 21 and a light amount of the infrared light LED 23 on the basis of a correlation value between the two pulse waves thus obtained.

The visible light LED 21 is a light source that emits visible light and is, for example, a white LED. The visible light is light within a visible light wavelength range (e.g., 400 nm to 800 nm). The visible light LED 21 is, for example, disposed in a ring shape on the lower surface of the housing 20. The visible light LED 21 may be a plurality of bombshell-shaped LEDs, may be a plurality of surface mount device (SMD) LEDs, or may be chip on board (COB) LEDs. The visible light LED 21 need not be disposed in a ring shape.

The visible light camera 22 is a camera that captures visible light. The visible light camera 22 is disposed close to a center of the visible light LED 21 disposed in a ring shape. That is, the visible light camera 22 is disposed so as to be surrounded by the visible light LED 21. The visible light camera 22 is a camera that includes an image sensor such as a charge coupled device (CCD) image sensor or a complementary metal oxide semiconductor (CMOS) image sensor. The visible light camera 22 causes the image sensor to obtain, as three kinds (RGB (Red, Green, and Blue)) of signals, visible light, i.e., light within a wavelength range from 400 nm to 800 nm by applying RGB color filters to the image sensor.

The infrared light LED 23 is a light source that emits infrared light. The infrared light is light within an infrared light wavelength range (e.g., 800 nm to 2500 nm). The infrared light LED 23 is disposed in a ring shape on an inner side of the visible light LED 21. The infrared light LED 23 may be a plurality of bombshell-shaped LEDs, may be a plurality of surface mount device (SMD) LEDs, or may be chip on board (COB) LEDs. The infrared light LED 23 need not be disposed in a ring shape. The infrared light LED 23 may be disposed on an outer side of the visible light LED 21 instead of being disposed on an inner side of the visible light LED 21.

The infrared light camera 24 is a camera that captures infrared light. The infrared light camera 24 may be a camera that captures an electromagnetic wave within a wavelength range (e.g., 700 nm to 900 nm) including part of the visible light wavelength range. The infrared light camera 24 is disposed close to a center of the infrared light LED 23 disposed in a ring shape. That is, the infrared light camera 24 is disposed so as to be surrounded by the infrared light LED 23. The infrared light camera 24 has a filter that is different from the filters of the visible light camera 22 and causes an image sensor to obtain, as one kind (monochromatic) of signal, infrared light, i.e., light within the wavelength range of 800 nm or higher.

The pulse wave computing device 100 is disposed in the housing 20. The pulse wave computing device 100 includes a central processing unit (CPU) 101, a main memory 102, a storage 103, and a communication interface (IF) 104.

The CPU 101 is a processor that executes a control program stored in the storage 103 or the like.

The main memory 102 is a volatile storage region (main storage device) used as a work area during execution of the control program by the CPU 101.

The storage 103 is a non-volatile storage region (auxiliary storage device) in which a control program, various kinds of data, and the like are held.

The communication IF 104 is a communication interface for transmission and reception of data to and from another device over a network. Specifically, the communication IF 104 supplies control signals for controlling the visible light LED 21, the visible light camera 22, the infrared light LED 23, and the infrared light camera 24 to the visible light LED 21, the visible light camera 22, the infrared light LED 23, and the infrared light camera 24. Furthermore, the communication IF 104 obtains imaging data obtained by the visible light camera 22 and the infrared light camera 24.

The communication IF 104 may be a communication interface that can be communicably connected to the mobile terminal 30. Specifically, the communication IF 104 may be a wireless local area network (LAN) interface that complies with an IEEE802.11a,b,g,n standard or may be a wireless communication interface that complies with a Bluetooth (Registered Trademark) standard.

1-1-2. Mobile Terminal

A hardware configuration of the mobile terminal 30 is described below with reference to FIG. 4.

Figure 4:
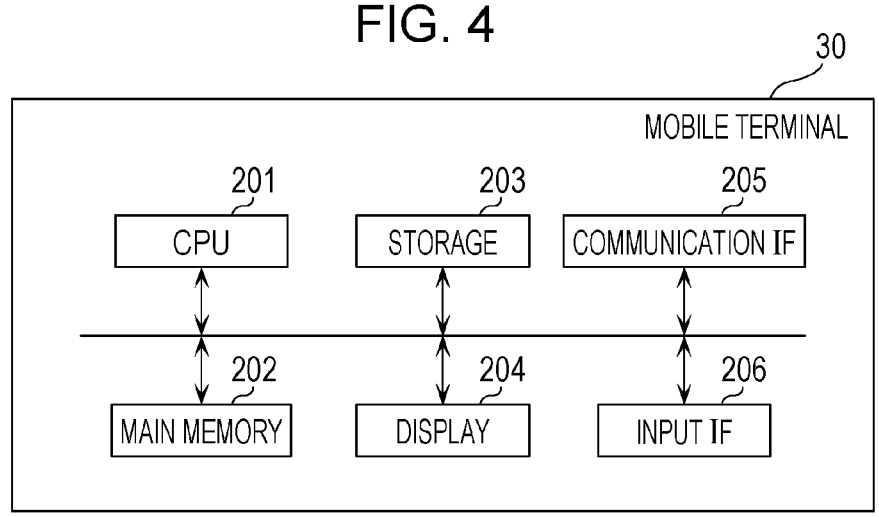
FIG. 4 is a block diagram illustrating an example of a hardware configuration of a mobile terminal according to the present embodiment.

FIG. 4 is a block diagram illustrating an example of a hardware configuration of the mobile terminal according to the present embodiment.

As illustrated in FIG. 4, the mobile terminal 30 includes a CPU 201, a main memory 202, a storage 203, a display 204, a communication IF 205, and an input IF 206. The mobile terminal 30 is, for example, an information terminal, such as a smartphone or a tablet terminal, that can perform communication.

The CPU 201 is a processor that executes a control program stored in the storage 203 or the like.

The main memory 202 is a volatile storage region (main storage device) used as a work area during execution of the control program by the CPU 201.

The storage 203 is a non-volatile storage region (auxiliary storage device) in which a control program, various kinds of data, and the like are held.

The display 204 is a display device on which a result of processing in the CPU 201 is displayed. The display 204 is, for example, a liquid crystal display or an organic EL display.

The communication IF 205 is a communication interface for communication with the pulse wave measuring device 10. The communication IF 205 may be, for example, a wireless local area network (LAN) interface that complies with a IEEE802.11a,b,g,n standard or may be a wireless communication interface that complies with a Bluetooth (Registered Trademark) standard. Alternatively, the communication IF 205 may be a wireless communication interface that complies with a communication standard used in a mobile communication system such as a third generation mobile communication system (3G), fourth generation mobile communication system (4G), or an LTE (Registered Trademark).

The input IF 206 is, for example, a touch panel that is disposed on a surface of the display 204 and receives user's input on a user interface (UI) displayed on the display 204. The input IF 206 may be an input device such as a numerical keypad or a keyboard.

Figure 6:
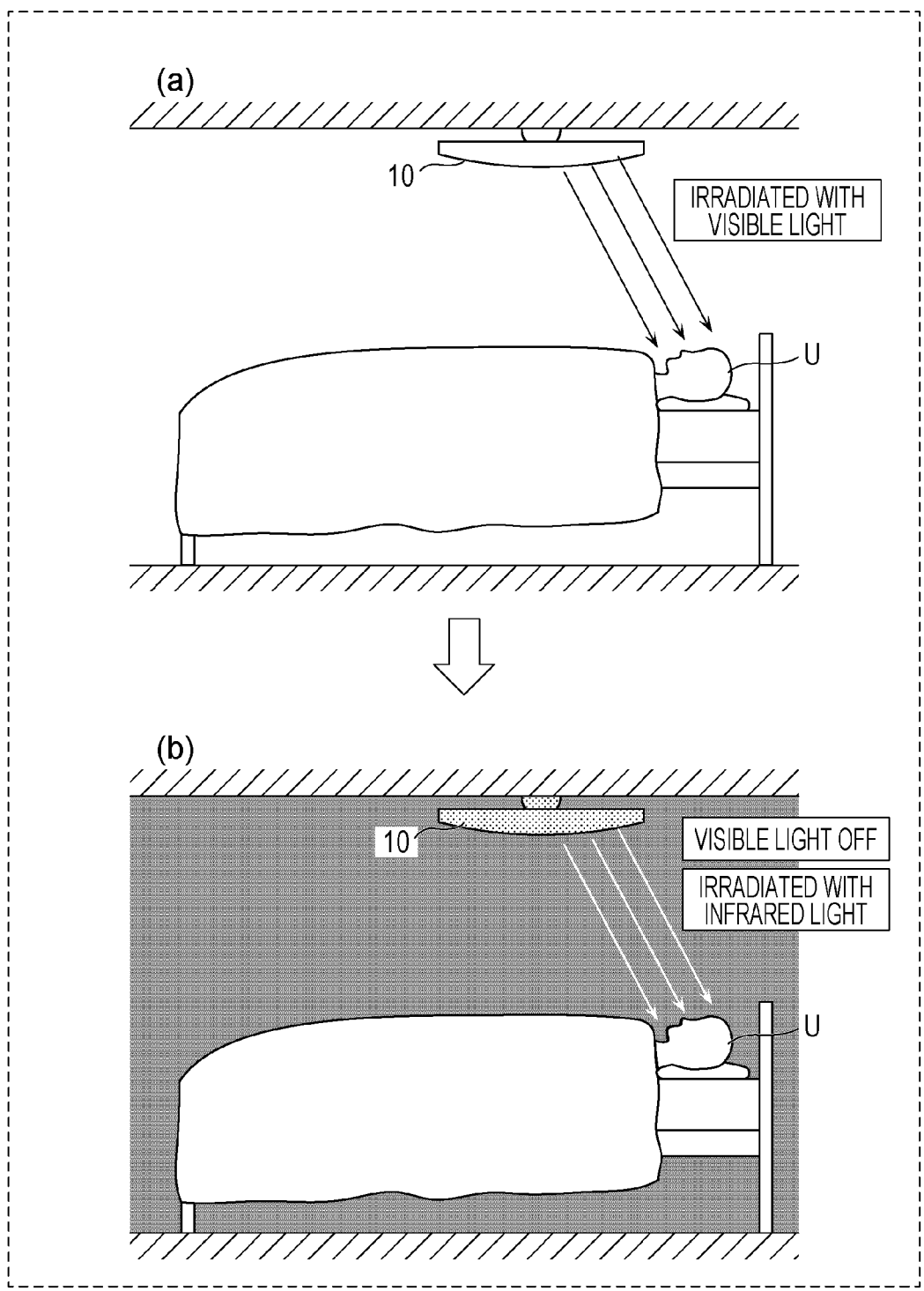
FIG. 6 is a diagram for explaining an example of use of the pulse wave measuring device.

FIGS. 5 and 6 are diagrams for explaining an example of use of the pulse wave measuring device 10.

The mobile terminal 30 may, for example, display, on the display 204, the UI for operation of the pulse wave measuring device 10 as illustrated in FIG. 5. The mobile terminal 30 may transmit a control signal to the pulse wave measuring device 10 in accordance with input made on the UI.

In the pulse wave measuring device 10, the mobile terminal 30 can be used by a user for switching on and off the visible light LED 21 and the infrared light LED 23. For example, the mobile terminal 30 can be used as a remote control of the pulse wave measuring device 10 by activating a remote control app for controlling the pulse wave measuring device 10 on the mobile terminal 30. A user can turn on the visible light LED 21 irrespective of whether the infrared light LED 23 is on or off by selecting "LIGHTING ON" as illustrated in FIG. 5(a).

FIG. 6(a) illustrates an example of a state where the visible light LED 21 is on. In a case where a user selects "INFRARED ON", the infrared light source can be turned on irrespective of whether the visible light LED 21 is on or off. For example, FIG. 6(b) illustrates a state where the visible light LED 21 is off and the infrared light LED is on. In a case where only infrared light is on, a user does not feel bright and therefore can sleep as usual. In a case where the user selects "OFF", both of the visible light LED 21 and the infrared light LED 23 are turned off, and the user is not irradiated with any of the light.

In a case where a user selects "BEDTIME MODE", which starts from a state where the visible light LED 21 is on and the infrared light LED is off, the visible light LED 21 gradually decreases a light amount thereof and is finally turned off and the infrared light LED 23 is turned on and gradually increases a light amount thereof. In this way, an optimum light amount of the infrared light LED 23 is determined, and a pulse wave of the user can be obtained even during sleep.

1-2. Functional Configuration

Next, a functional configuration of the pulse wave measuring device 10 is described below with reference to FIG. 7.

Figure 7:
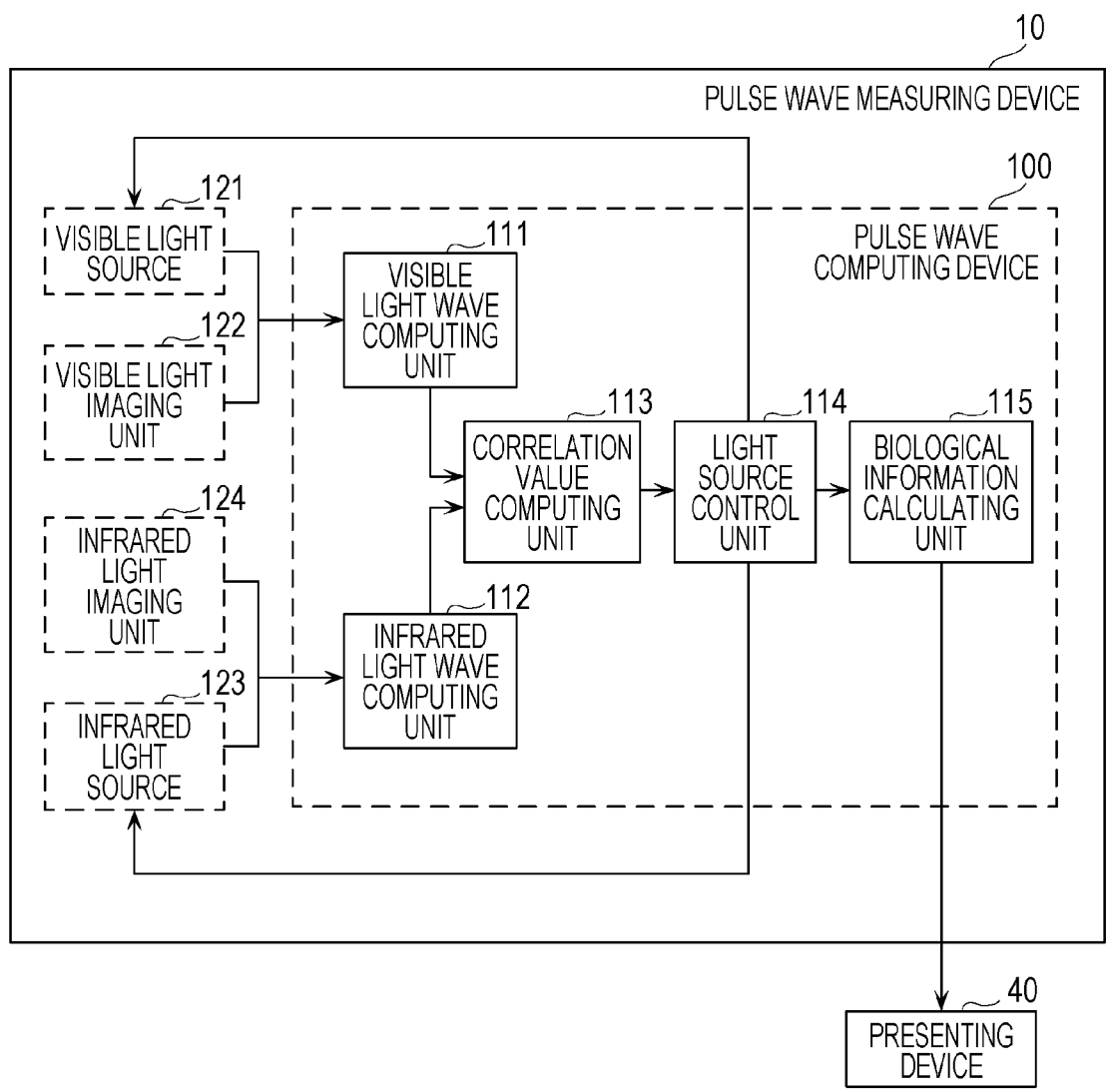
FIG. 7 is a block diagram illustrating an example of a functional configuration of the pulse wave measuring device according to the present embodiment.

FIG. 7 is a block diagram illustrating an example of a functional configuration of the pulse wave measuring device according to the present embodiment.

As illustrated in FIG. 7, the pulse wave measuring device 10 includes a visible light source 121, a visible light imaging unit 122, an infrared light source 123, an infrared light imaging unit 124, and the pulse wave computing device 100.

The visible light source 121 irradiates a user with visible light, and a light amount of the visible light is adjusted by a light source control unit 114. The visible light source 121 is realized, for example, by the visible light LED 21. The visible light source 121 may be realized by a fluorescent lamp.

Although the light amount of the visible light source 121 is controlled by the light source control unit 114 in this example, the present embodiment is not limited to this. The light amount of the visible light source 121 may be manually controlled by the user by using a controller. For example, in a case where the user can sleep under visible light of an amount that is equal to or smaller than a predetermined light amount, this allows the user to sleep while obtaining a pulse wave of the user in a state where the user is irradiated with visible light of an amount that is equal to or smaller than the predetermined light amount by the visible light source 121.

The visible light source 121 may be set so as to be activated every time the user enters a room. This makes it possible to obtain pulse wave information of the user every time the user enters the room, thereby making it possible to obtain pulse wave information during, before, and after sleep.

The visible light imaging unit 122 takes, in a visible light wavelength range, an image of a subject irradiated with visible light by the visible light source 121. Specifically, the visible light imaging unit 122 supplies a visible light image, in a visible light wavelength range (e.g., color), of skin of an irradiated user to a visible light wave computing unit 111 of the pulse wave computing device 100. The visible light imaging unit 122 supplies, for example, a plurality of visible light images taken at a plurality of different timings to the visible light wave computing unit 111. For example, visible light imaging unit 122 supplies, as the visible light images, skin images obtained by imaging skin including a human face or hand. The skin images are images of the same position of skin including a human face or hand that are taken at a plurality of successive timings and are, for example, a moving image or a plurality of still images. The visible light imaging unit 122 is realized, for example, by the visible light camera 22.

The infrared light source 123 irradiates the user with infrared light, and a light amount of the infrared light is adjusted by the light source control unit 114. The infrared light source 123 is realized, for example, by the infrared light LED 23.

The infrared light imaging unit 124 takes, in an infrared light wavelength range, a subject irradiated with infrared light by the infrared light source 123. Specifically, the infrared light imaging unit 124 supplies an infrared light image, in an infrared light wavelength range (e.g., monochromatic), of skin of an irradiated user to an infrared light wave computing unit 112 of the pulse wave computing device 100. The infrared light imaging unit 124 supplies, for example, a plurality of infrared light images taken at a plurality of different timings to the infrared light wave computing unit 112. The infrared light imaging unit 124 images the same portion as the portion imaged by the visible light imaging unit 122. For example, the infrared light imaging unit 124 supplies, as the infrared light images, skin images of skin including a human face or hand. This is because similar pulse waves can be obtained in a visible light wavelength range and an infrared light wavelength range by causing the infrared light imaging unit 124 to image the same portion as the portion imaged by the visible light imaging unit 122 and thus features of the pulse waves can be easily compared.

In order to image the same portion, regions of interest (ROIs) having the same size are set in the visible light imaging unit 122 and the infrared light imaging unit 124. Then, it may be determined whether or not the same portion has been imaged by comparing images within the ROIs taken by the visible light imaging unit 122 and the infrared light imaging unit 124, for example, by using pattern recognition. Alternatively, the same portion may be specified by obtaining coordinates and sizes of feature points in eyes, a nose, a mouth, and the like by face recognition using the visible light image obtained by the visible light imaging unit 122 and the infrared light image obtained by the infrared light imaging unit 124 and then computing a coordinate (relative position) from the feature points in the eyes, nose, mouth, and the like in consideration of a ratio of sizes of the eyes, nose, mouth, and the like.

The skin images obtained by the infrared light imaging unit 124 are images of the same portion of skin including a human face or hand that are taken at a plurality of successive timings and are, for example, a moving image or a plurality of still images, as in the case of the skin images obtained by the visible light imaging unit 122. The infrared light imaging unit 124 is realized, for example, by the infrared light camera 24.

The pulse wave computing device 100 includes the visible light wave computing unit 111, the infrared light wave computing unit 112, a correlation value computing unit 113, a light source control unit 114, and a biological information calculating unit 115. The constituent elements of the pulse wave computing device 100 are described below in order.

Visible Light Wave Computing Unit

The visible light wave computing unit 111 obtains visible light images from the visible light imaging unit 122 and extracts a visible light wave that is a wave indicative of a user's pulse wave from the obtained visible light images. The visible light wave computing unit 111 extracts a first visible light wave from first visible light images obtained before control of the light amount of the visible light source 121. Furthermore, the visible light wave computing unit 111 extracts a second visible light wave from second visible light images obtained after control of the light amount of the visible light source 121. The control of the light amount of the visible light source 121 refers to supplying, from the light source control unit 114 that will be described later to the visible light source 121, a first control signal for decreasing the light amount of visible light emitted from the visible light source 121 or a third control signal for increasing the light amount of visible light emitted from the visible light source 121. As described above, the plurality of visible light images obtained from the visible light imaging unit 122 include the first visible light images obtained before control of the light amount of the visible light source 121 and the second visible light images obtained after control of the light amount of the visible light source 121. The visible light waves extracted from the plurality of visible light image include the first visible light wave extracted from the first visible light images and the second visible light wave extracted from the second visible light images.

The visible light wave computing unit 111 may extract a plurality of first feature points that are predetermined feature points in the extracted first visible light wave. Specifically, the visible light wave computing unit 111 extracts a plurality of first peak points from the first visible light wave by dividing the first visible light wave into a plurality of first unit waves on the basis of a pulse wave cycle that is a cycle of a pulse wave and then extracting, for each of the plurality of first unit waves, a first peak point that is a first top point indicative of a maximum value of the first unit wave or a first bottom point indicative of a minimum value of the first unit wave. The first peak points are an example of the first feature points.

The visible light wave computing unit 111 obtains pulse wave timings as the feature points of the visible light wave and then computes a heartbeat time interval from adjacent pulse wave timings. That is, the visible light wave computing unit 111 calculates, for each of the plurality of extracted first feature points, a period between the first feature point and another first feature point adjacent to this first feature point as a first heartbeat time interval. For example, the visible light wave computing unit 111 calculates a plurality of first heartbeat time intervals by calculating, for each of the plurality of extracted first peak points, a first heartbeat time interval that is a time interval between a first time point of the first peak point and a second time point of another first peak point that is adjacent in a time sequence to the first peak point.

Specifically, the visible light wave computing unit 111 extracts a visible light wave on the basis of a temporal change of luminance extracted from a plurality of visible light images associated with respective imaging timings. That is, each of the plurality of visible light images obtained from the visible light imaging unit 122 is associated with a time point at which the visible light image is taken by the visible light imaging unit 122. The visible light wave computing unit 111 obtains timings of user's pulse waves (hereinafter also referred to as pulse wave timings) by obtaining intervals between predetermined features points of the visible light wave. Then, the visible light wave computing unit 111 calculates, for each of the plurality of obtained pulse wave timings, an interval between the pulse wave timing and a next pulse wave timing as a heartbeat time interval.

The visible light wave computing unit 111 may extract a plurality of third feature points that are predetermined feature points in the extracted second visible light wave. Specifically, the visible light wave computing unit 111 may extract a plurality of third peak points from the second visible light wave by dividing the second visible light wave into a plurality of third unit waves on the basis of a pulse wave cycle and then extracting, for each of the plurality of third unit waves, a third peak point that is a third top point indicative of a maximum value of the third unit wave or a bottom point indicative of a minimum value of the third unit wave. The third peak points are an example of the third feature points.

The visible light wave computing unit 111 may calculate a plurality of third heartbeat time intervals by calculating, for each of the plurality of extracted third peak points, a third heartbeat time interval that is a time interval between a fifth time point of the third peak point and a sixth time point of another third peak point that is adjacent in a time sequence to the third peak point.

For example, the visible light wave computing unit 111 specifies a timing at which a change in luminance is largest by using the extracted visible light wave and specifies the specified timing as a pulse wave timing. Alternatively, the visible light wave computing unit 111 specifies a position of a face or a hand in a plurality of visible light images by using a face or hand pattern that is held in advance and then specifies a visible light wave by using a temporal change in luminance of the specified position. The visible light wave computing unit 111 calculate a pulse wave timing by using the specified visible light wave. The pulse wave timing is a time point at which a predetermined feature point is obtained in a temporal wave of luminance, i.e., a temporal wave of a pulse wave. The predetermined feature point is, for example, a peak position (a time point of a top point or a bottom point) of the temporal wave of luminance. The peak position can be specified by using a known local search method such as a hill climbing method, an autocorrelation method, or a method using a differential function. The visible light wave computing unit 111 can be realized, for example, by the CPU 101, the main memory 102, the storage 103, and the like.

In general, a pulse wave is a change in blood pressure or volume in a peripheral vascular system caused by a beat of a heart. That is, a pulse wave is a change in volume of a blood vessel that occurs when blood is sent from a heart and reaches a face or a hand due to contraction of the heart. When the volume of a blood vessel in a face or a hand changes, the amount of blood passing the blood vessel changes. This changes a color of skin depending on the amount of components in the blood such as hemoglobin. Accordingly, luminance of the face or hand in taken images changes in accordance with a pulse wave. That is, information on movement of blood can be obtained by using a temporal change in luminance of the face or hand obtained from images of the face or hand taken at a plurality of timings. In this way, the visible light wave computing unit 111 obtains a pulse wave timing by computing information on movement of blood from a plurality of images taken in a time sequence.

Images of luminance of a green wavelength range in visible light images may be used to obtain a pulse wave timing in a visible light wavelength range. This is because a change in luminance caused by a pulse wave is large close to a green wavelength range in images taken in a visible light wavelength range. In a visible light image including a plurality of pixels, luminance, in the green wavelength range, of pixels corresponding to a face or a hand in which a large amount of blood flows is lower than luminance, in the green wavelength range, of pixels corresponding to the face or hand in which a small amount of blood flows.

Figure 8:
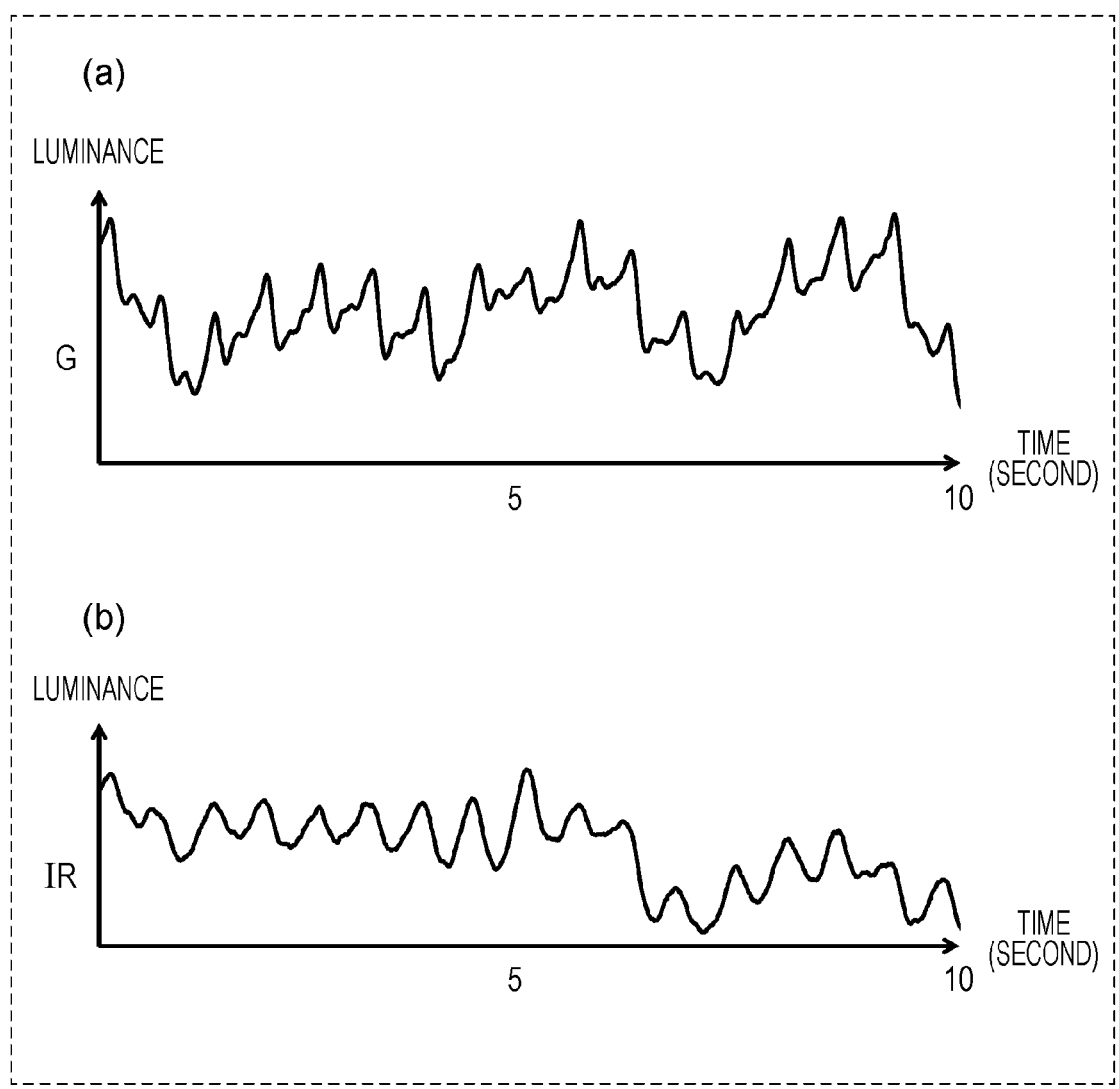
FIG. 8 is a graph illustrating an example of a change in luminance of a visible light image and an infrared light image according to the present embodiment.

FIG. 8(a) is a graph illustrating an example of a change in luminance of a visible light image, especially a change in luminance of green in the present embodiment. Specifically, FIG. 8(a) illustrates a change in luminance of a green component (G) in a cheek region of a user in visible light images taken by the visible light imaging unit 122. In the graph illustrated in FIG. 8(a), the horizontal axis represents a time, and the vertical axis represents luminance of the green component (G). As is clear from FIG. 8(a), the luminance periodically changes due to a pulse wave.

Under an ordinary circumstance, i.e., in a case where skin is imaged in a visible light wavelength range, a visible light image includes noise due to scattering light caused by lighting or various factors. In view of this, the visible light wave computing unit 111 may obtain a visible light image in which a change in luminance of skin caused by a pulse wave is large by performing signal processing using a filter or the like on a visible light image obtained from the visible light imaging unit 122. An example of the filter used for the signal processing is a low-pass filter. That is, in the present embodiment, the visible light wave computing unit 111 performs the process for extracting a visible light wave by using a change in luminance of the green component (G) passed through a low-pass filter.

Figure 9:
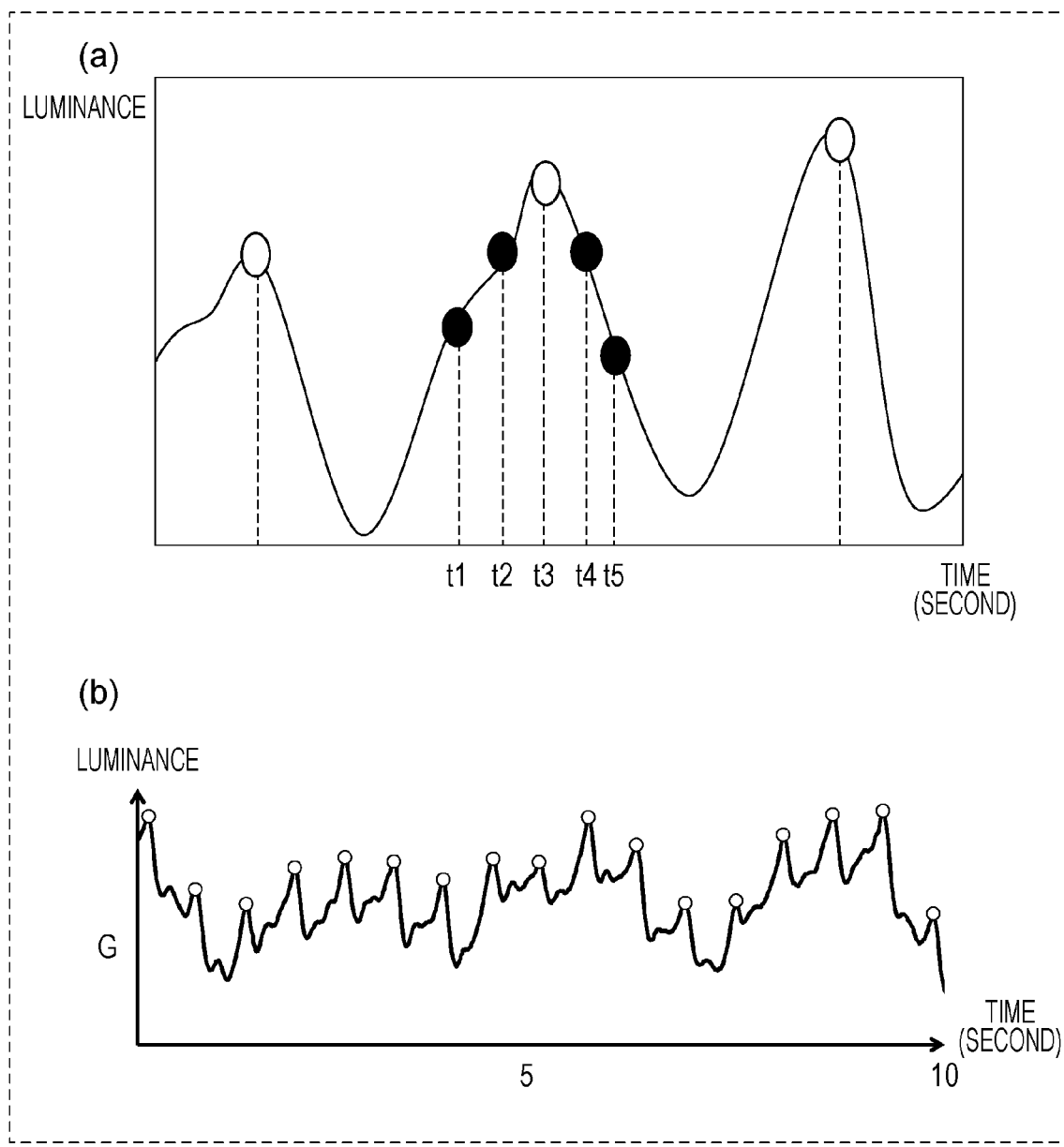
FIG. 9 is a graph illustrating an example of calculation of a pulse wave timing according to the present embodiment.

FIG. 9(a) is a graph illustrating an example of calculation of a pulse wave timing according to the present embodiment. In the graph illustrated in FIG. 9(a), the horizontal axis represents a time, and the vertical axis represents luminance. In the temporal wave in the graph of FIG. 9(a), each of the points at time points t1 to t5 is an inflection point or a top point. The points in the temporal wave of the graph include inflection points and peak points (top points and bottom points) as feature points. A top point is a point indicative of a local maximum value of a portion bulging upward in the temporal wave, and a bottom point is a point indicative of local minimum value of a portion bulging downward in the temporal wave. A time point at which a point (top point) having larger luminance than previous and next time points is obtained or a time point at which a point (bottom point) having smaller luminance than previous and next time points is obtained among the points included in the temporal wave is a pulse wave timing.

A method for specifying a position of a top point i.e., a method for peak search is described by using the luminance temporal waveform in the graph illustrated in FIG. 9(a). The visible light wave computing unit 111 regards a point at the time point t2 as a current reference point in the temporal waveform of the luminance. The visible light wave computing unit 111 compares the point at the time point t2 and the point at the time point t1 previous to the time point t2 and compares the point at the time point t2 and the point at the time point t3 next to the time point t2. The visible light wave computing unit 111 determines that the reference point is positive in a case where the luminance of the reference point is higher than both of the luminance of the point at the previous time point and the luminance of the point at the next time point. That is, in this case, the visible light wave computing unit 111 determines that the reference point is a peak point (top point) and that the time point of the reference point is a pulse wave timing.

Meanwhile, in a case where the luminance of the reference point is lower than at least one of the luminance of the point at the previous time point and the luminance of the point at the next time point, the visible light wave computing unit 111 determines that the reference point is negative. That is, in this case, the visible light wave computing unit 111 determines that the reference point is not a peak point (top point) and that the time point of the reference point is not a pulse wave timing.

In FIG. 9(a), the luminance of the point at the time point t2 is higher than the luminance of the point at the time point t1, but the luminance of the point at the time point t2 is lower than the luminance of the point at the time point t3 Accordingly, the visible light wave computing unit 111 determines that the point at the time point t2 is negative. Next, the visible light wave computing unit 111 increments the reference point by one and regards the point at the next time point t3 as the reference point. Since the luminance of the point at the time point t3 is higher than both of the luminance of the point at the time point t2 previous to the time point t3 and the luminance of the point at the time point t4 next to the time point t3, the visible light wave computing unit 111 determines that the point at the time point t3 is positive. The visible light wave computing unit 111 supplies a time point of a point determined to be positive to the correlation value computing unit 113 as a pulse wave timing. In this way, time points indicated by the while circles are specified as pulse wave timings as illustrated in FIG. 9(b).

The visible light wave computing unit 111 may specify a pulse wave timing by considering that a heartbeat time interval is, for example, from 333 ms to 1000 ms on the basis of knowledge of a general heart rate (e.g., 60 bpm to 180 bpm). By considering a general heartbeat time interval, the visible light wave computing unit 111 can specify a proper pulse wave timing by making the comparison concerning luminance as for some points without the need to make the comparison concerning luminance for all of the points. That is, it is only necessary to make the comparison concerning luminance by using, as a reference point, each of points within a range from 333 ms to 1000 ms from a pulse wave timing that is obtained last. In this case, it is possible to specify a next pulse wave timing without making the comparison concerning luminance by using, as a reference point, points that are outside this range. This makes it possible to achieve a robust pulse wave timing obtaining process under an ordinary circumstance.

The visible light wave computing unit 111 calculates a heartbeat time interval by calculating a temporal difference between adjacent pulse wave timings. The heartbeat time interval fluctuates over time. Therefore, by comparing the heartbeat time interval with a heartbeat time interval of a pulse wave specified from an infrared light wave obtained in the same period, the heartbeat time interval can be used to compute a correlation value at a predetermined feature point between the visible light wave and the infrared light wave.

Figure 10:
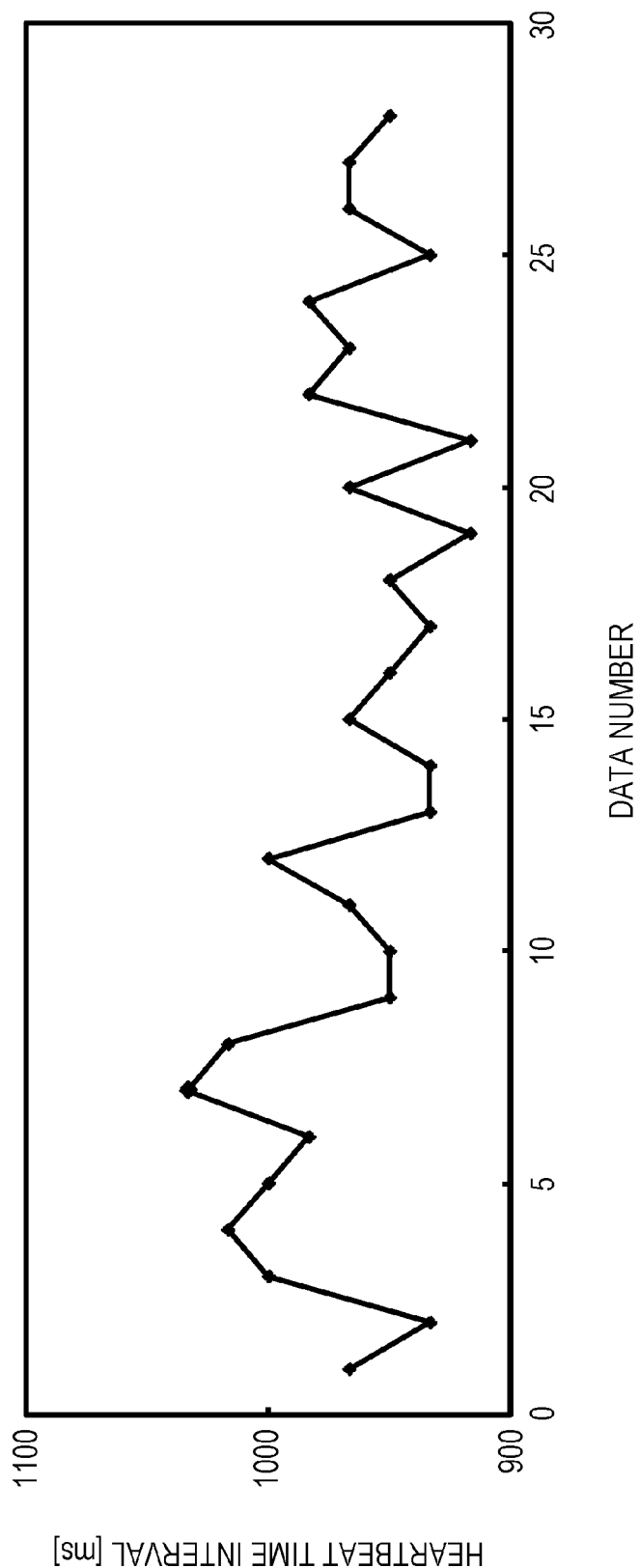
FIG. 10 is a graph illustrating an example of heartbeat time intervals obtained in a time sequence.

FIG. 10 is a graph illustrating an example of heartbeat time intervals obtained in a time sequence. In the graph illustrated in FIG. 10, the horizontal axis represents a data number associated with a heartbeat time interval obtained in a time sequence, and the vertical axis represents a heartbeat time interval. As is clear from FIG. 10, the heartbeat time interval fluctuates over time. The data number is an order in which data (a heartbeat time interval in this example) is stored in a memory. That is, a data number corresponding to an n-th (n is a natural number) recorded heartbeat time interval is "n".

The visible light wave computing unit 111 may further extract a time point of an inflection point that immediately follows a pulse wave timing in a visible light wave. Specifically, the visible light wave computing unit 111 obtains a local minimum point of visible light differential luminance by calculating a first derivation of a luminance value of the visible light wave and then calculates a time point of the local minimum point as a time point of an inflection point (hereinafter referred to as an inflection point timing). That is, the visible light wave computing unit 111 may extract, as predetermined feature points, a plurality of inflection points each located between a top point and a bottom point.

The visible light wave computing unit 111 may calculate an inflection point timing by considering that a heartbeat time interval is, for example, 333 ms to 1000 ms on the basis of general knowledge of a heart rate. This makes it possible to more accurately calculate an inflection point timing since an inflection point that is irrelevant with a heartbeat is not specified even in a case where such an inflection point is included in a visible light wave.

Figure 11:
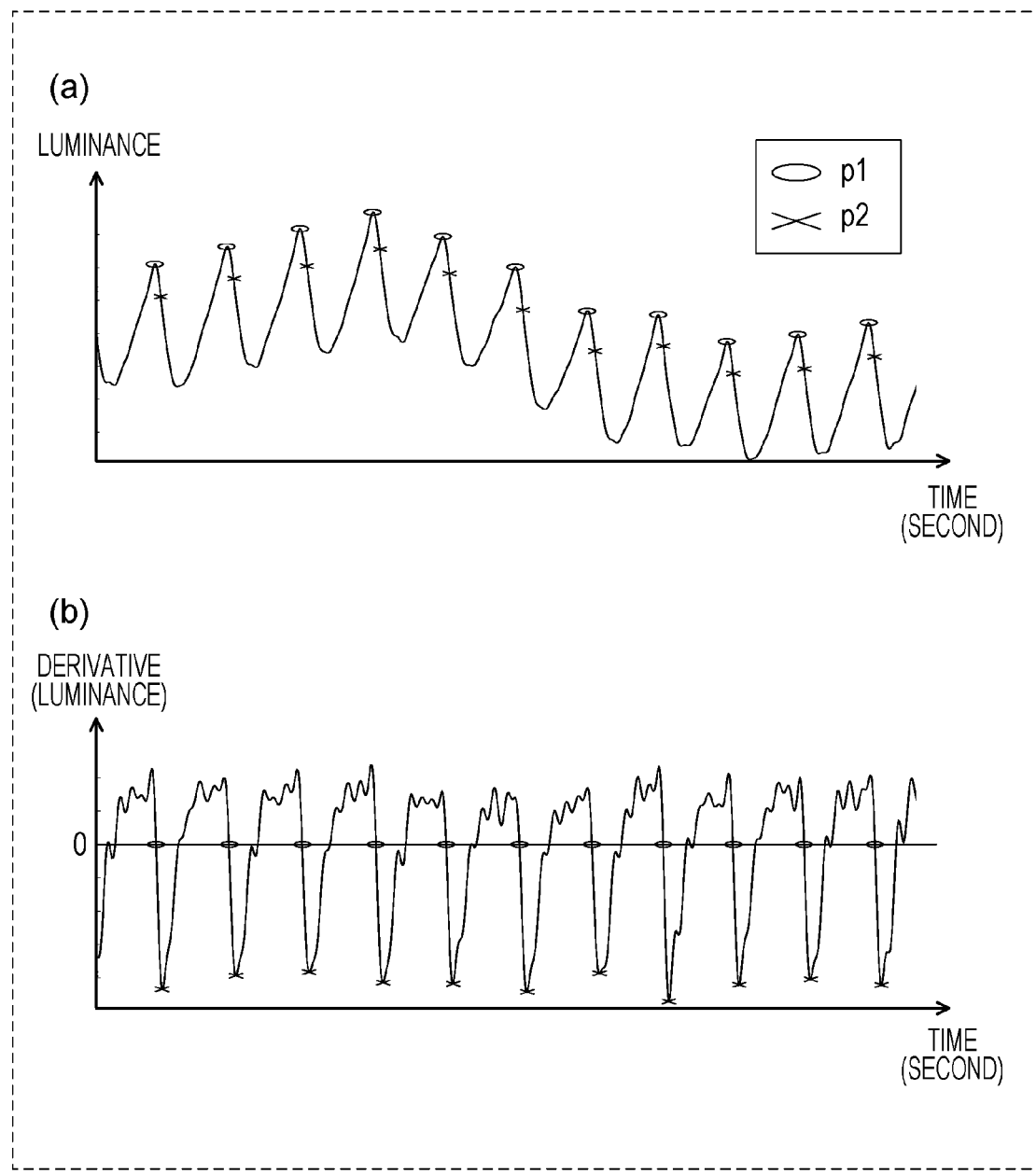
FIG. 11 is a graph for explaining a method for extracting inflection points from a pulse wave.

FIG. 11 is a graph for explaining a method for extracting inflection points from a pulse wave. Specifically, FIG. 11(a) is a graph illustrating a visible light wave obtained from visible light images, and FIG. 11(b) is a graph plotting first derivative values of FIG. 11(a). In FIG. 11(a), the circles represent top points among peak points, and the x marks represent inflection points. In FIG. 11(b), the circles represents points corresponding to the top points in FIG. 11(a), and the x marks represents points corresponding to the inflection points in FIG. 11(a). In the graph illustrated in FIG. 11(a), the horizontal axis represents a time, and the vertical axis represents a luminance value. In the graph illustrated in FIG. 11(b), the horizontal axis represents a time, and the vertical axis represents a derivative of the luminance value.

Especially visible light images capturing green light are used to extract a visible light wave as described above. The principle of extraction of the visible light wave is described below. In a case where the amount of blood in a blood vessel in a face, a hand, or the like increases or decreases in accordance with a pulse wave, the amount of hemoglobin in blood increases or decreases in accordance with the amount of blood. That is, the amount of hemoglobin that absorbs light in a green wavelength range increases or decreases in accordance with the increase or decrease in the amount of blood in the blood vessel. Accordingly, in visible light images taken by the visible light imaging unit 122, a color of skin close to the blood vessel changes in accordance with the increase or decrease in the amount of blood, and a luminance value of visible light, especially a green component fluctuates accordingly. Specifically, since hemoglobin absorbs green light, a luminance value in a visible light image decreases by a value corresponding to an amount absorbed by hemoglobin.

A gradient from a top point to a next bottom point of a visible light wave is steeper than a gradient from a bottom point to a top point of the visible light wave. Accordingly, a period from a bottom point to a top point is relatively susceptible to the influence of noise. Meanwhile, a period from a top point to a next bottom point in which a gradient is steep is less susceptible to the influence of noise. Accordingly, an inflection point timing existing between the top point and the next bottom point is also less susceptible to the influence of noise and is therefore can be obtained relatively stably. For this reason, the visible light wave computing unit 111 may calculate, as a heartbeat time interval, a time difference between inflection points each existing between a top point and a next bottom point.

A peak point of a visible light wave described above is a point at which a derivative becomes 0 immediately before an inflection point. Specifically, as is clear from FIG. 11(b), a time point of a point at which a derivative becomes 0 immediately before an x mark representing an inflection point corresponds to a time point of a circle representing a top point of FIG. 11(a). The visible light wave computing unit 111 may limit top points obtained from a visible light wave to those immediately before inflection points by using this characteristic.

Furthermore, the visible light wave computing unit 111 calculates a slope from a top point to a bottom point of the visible light wave. The visible light wave computing unit 111 calculates a first slope of a first straight line connecting one of a plurality of first top points and one of a plurality of first bottom points that immediately follows, in a time sequence, the one first top point. The slope in the visible light wave is preferably made as large as possible by adjusting the luminance of the visible light source 121. This is because as the slope becomes larger, the sharpness of a top point of the visible light wave becomes higher, and as a result, a time deviation of a pulse wave timing caused by filter processing or the like becomes smaller.

Figure 12:
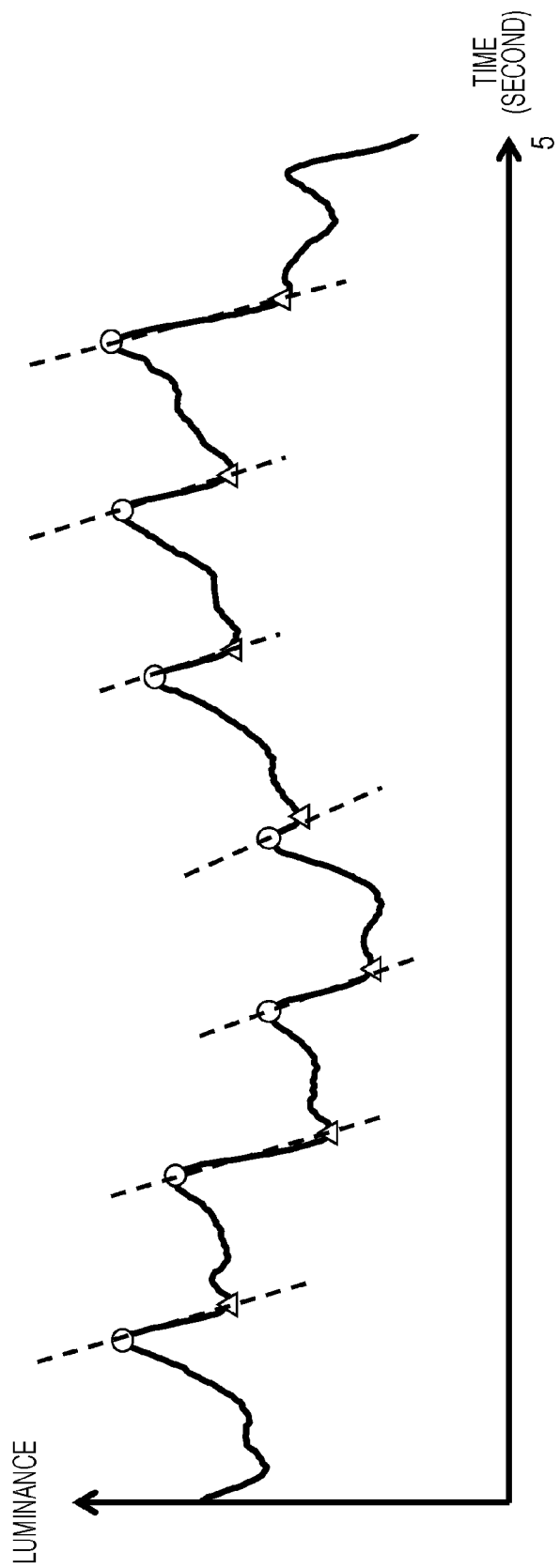
FIG. 12 is a graph illustrating a visible light wave for explaining a method for computing a slope from a top point to a bottom point in a visible light wave.

FIG. 12 is a graph illustrating a visible light wave for explaining a method for computing a slope of the visible light wave. In the graph illustrated in FIG. 12, the horizontal axis represents a time, the vertical axis represents a luminance value, the circles represent top points, and triangles represent bottom points. The visible light wave computing unit 111 connects a top point (circle) and a next bottom point (triangle) with a straight line and calculates a slope of the straight line. The slope thus calculated varies depending on the amount of light emitted from a light source of the visible light source 121, a portion of user's skin obtained by the visible light imaging unit 122, and the like. Therefore, the light amount of the visible light source 121 and an ROI corresponding to a user's portion in the visible light imaging unit 122 are set so that a clear pulse wave can be obtained, for example, so that a heartbeat time interval from 333 ms to 1000 ms can be continuously obtained. In this way, slope information can be recorded and compared with slope information in a pulse wave of infrared light. The visible light wave computing unit 111 records, in a memory (e.g., the storage 103) as a first slope A, a slope from a top point to a bottom point in a visible light wave in an initial state, i.e., in a state from when the visible light source 121 is turned on to when the light source control unit 114 changes the light amount of visible light of the visible light source 121 and the light amount of infrared light of the infrared light source 123. The pulse wave measuring device 10 gradually decreases the light amount of the visible light source 121 to zero and gradually increases the light amount of the infrared light source 123 while comparing feature points of the visible light wave and feature points of the infrared light wave. Since the light amount of visible light is gradually decreased, a slope from a top point to a bottom point of the visible light wave is largest in the initial state.

Infrared Light Wave Computing Unit

The infrared light wave computing unit 112 obtains infrared light images from the infrared light imaging unit 124 and extracts an infrared light wave that is a wave indicative of a user's pulse wave from the obtained infrared light images. The infrared light wave computing unit 112 extracts a first infrared light wave from first infrared light images obtained before control of the light amount of the infrared light source 123. Furthermore, the infrared light wave computing unit 112 extracts a second infrared light wave from second infrared light images obtained after control of the light amount of the infrared light source 123. The control of the light amount of the infrared light source 123 refers to supplying, from the light source control unit 114 that will be described later to the infrared light source 123, a second control signal for increasing the light amount of infrared light of the infrared light source 123 or a fourth control signal for decreasing the light amount of infrared light of the infrared light source 123. As described above, the plurality of infrared light images obtained from the infrared light imaging unit 124 include the first infrared light images obtained before control of the light amount of the infrared light source 123 and the second infrared light images obtained after control of the light amount of the infrared light source 123.

The infrared light wave computing unit 112 may extract a plurality of second feature points that are predetermined feature points in the extracted first infrared light wave. Specifically, the infrared light wave computing unit 112 extracts a plurality of second peak points from the first infrared light wave by dividing the first infrared light wave into a plurality of second unit waves on the basis of a pulse wave cycle and then extracting, for each of the plurality of second unit waves, a second peak point that is a second top point indicative of a maximum value of the second unit wave or a second bottom point indicative of a minimum value of the second unit wave. The second peak points are an example of the second feature points.

The infrared light wave computing unit 112 obtains pulse wave timings as the features points of the infrared light wave as in the case of the visible light wave computing unit 111 and then computes a heartbeat time interval from adjacent pulse wave timings. That is, the infrared light wave computing unit 112 calculates, for each of the plurality of extracted second feature points, a period between the second feature point and another second feature point adjacent to the second feature point as a second heartbeat time interval. Specifically, the infrared light wave computing unit 112 extracts an infrared light wave on the basis of a temporal change in luminance extracted from a plurality of infrared light images. That is, each of the plurality of infrared light images obtained from the infrared light imaging unit 124 is associated with a time point at which the infrared light image is taken by the infrared light imaging unit 124. For example, the infrared light wave computing unit 112 calculates a plurality of second heartbeat time intervals by calculating, for each of the plurality of extracted second peak points, a second heartbeat time interval that is a time interval between a third time point of the second peak point and a fourth time point of another second peak point that is adjacent in a time sequence to the second peak point.

The infrared light wave computing unit 112 may extract a plurality of fourth feature points that are predetermined feature point of the extracted second infrared light wave. Specifically, the infrared light wave computing unit 112 may extract a plurality of fourth peak points from the second infrared light wave by dividing the second infrared light wave into a plurality of fourth unit waves on the basis of a pulse wave cycle and then extracting, for each of the plurality of fourth unit waves, a fourth peak point that is a fourth top point indicative of a maximum value of the fourth unit wave or a fourth bottom point indicative of a minimum value of the fourth unit wave. The fourth peak points are an example of the fourth feature points.

The infrared light wave computing unit 112 may calculate a plurality of fourth heartbeat time intervals by calculating, for each of the plurality of extracted fourth peak points, a fourth heartbeat time interval that is a time interval between a seventh time point of the fourth peak point and an eighth time point of another fourth peak point that is adjacent in a time sequence to the fourth peak point.

The infrared light wave computing unit 112 can specify a peak position that is a predetermined feature point of the infrared light wave by using a known local search method such as a hill climbing method, an autocorrelation method, or a method using a differential function as in the case of the visible light wave computing unit 111. The infrared light wave computing unit 112 can be realized, for example, by the CPU 101, the main memory 102, the storage 103, and the like as in the case of the visible light wave computing unit 111.

In general, luminance of a skin region such as a face or a hand changes from one infrared light image to another depending on the amount of components such as hemoglobin in blood as in the case of visible light images. That is, information on movement of blood can be obtained by using a temporal change in luminance of the face or hand obtained from images of the face or hand taken at a plurality of timings. In this way, the infrared light wave computing unit 112 obtains a pulse wave timing by computing information on movement of blood from a plurality of images taken in a time sequence.

Images of luminance of a wavelength range of 800 nm or higher in infrared light images may be used to obtain a pulse wave timing in an infrared light wavelength range. This is because a change in luminance caused by a pulse wave is large close to a wavelength range of 800 nm to 950 nm in images taken in an infrared light wavelength range.

FIG. 8(b) is a graph illustrating an example of a change in luminance of an infrared light image in the present embodiment. Specifically, FIG. 8(b) illustrates a change in luminance in a cheek region of a user in infrared light images taken by the infrared light imaging unit 124. In the graph illustrated in FIG. 8(b), the horizontal axis represents a time, and the vertical axis represents luminance. As is clear from FIG. 8(b), the luminance periodically changes due to a pulse wave, However, in a case where skin is imaged in an infrared light wavelength range, the amount of infrared light absorbed by hemoglobin is small as compared to a case where skin is imaged in a visible light wavelength range. That is, an infrared light image taken in an infrared light wavelength range is more likely to contain noise due to various factors such as a body motion. In view of this, the infrared light wave computing unit 112 may obtain an infrared light image in which a change in luminance caused by a pulse wave is large by performing signal processing using a filter or the like on a taken infrared light image and irradiating a user's skin region with a proper light amount of infrared light. An example of the filter used for the signal processing is a low-pass filter. That is, in the present embodiment, the infrared light wave computing unit 112 performs the process for extracting an infrared light wave by using a change in luminance of infrared light passed through a low-pass filter. A method for determining the light amount of infrared light emitted from the infrared light source 123 will be described in association with the correlation value computing unit 113 or the light source control unit 114.

Next, a method for peak search in the infrared light wave computing unit 112 is described. A method similar to the method for peak search in a visible light wave can be used as a method for peak search in an infrared light wave.

The infrared light wave computing unit 112 may specify a pulse wave timing by considering that a heartbeat time interval is, for example, from 333 ms to 1000 ms on the basis of knowledge of a general heart rate (e.g., 60 bpm to 180 bpm) as in the case of the visible light wave computing unit 111. By considering a general heartbeat time interval, the infrared light wave computing unit 112 can specify a proper pulse wave timing by making the comparison concerning luminance as for some points without the need to make the comparison concerning luminance for all of the points. That is, it is only necessary to make the comparison concerning luminance by using, as a reference point, each of points within a range from 333 ms to 1000 ms from a pulse wave timing that is obtained last. In this case, it is possible to specify a next pulse wave timing without making the comparison concerning luminance by using, as a reference point, points that are outside this range.

The infrared light wave computing unit 112 calculates a heartbeat time interval by calculating a temporal difference between adjacent pulse wave timings as in the case of the visible light wave computing unit 111. The infrared light wave computing unit 112 may further extract a time point of an inflection point that immediately follows a pulse wave timing in an infrared light wave. For example, the infrared light wave computing unit 112 obtains a local minimum point of infrared light differential luminance by calculating a first derivation of a luminance value of the infrared light wave and then calculates a time point of the local minimum point as a time point of an inflection point (hereinafter referred to as an inflection point timing). That is, the infrared light wave computing unit 112 may extract, as predetermined feature points, a plurality of inflection points each located between a top point and a bottom point.

Furthermore, the infrared light wave computing unit 112 calculates a slope from a top point to a bottom point of the infrared light wave as in the case of the visible light wave computing unit 111. That is, the infrared light wave computing unit 112 calculates a second slope of a second straight line connecting one of a plurality of fourth top points and one of a plurality of fourth bottom points that immediately follows, in a time sequence, the fourth top point in a second infrared light wave.

As described above, the infrared light wave computing unit 112 extracts a plurality of predetermined feature points as second feature points by performing processing similar to the processing performed by the visible light wave computing unit 111. However, an infrared light wave markedly changes depending on a light amount of infrared light emitted from a light source as compared with a visible light wave. That is, an infrared light wave is more susceptible to the influence of a light amount of a light source than a visible light wave.

FIG. 13 is a graph illustrating infrared light waves obtained in cases where human skin images are obtained by an infrared light camera at different levels of light amounts of an infrared light source. From FIG. 13(a) to FIG. 13(d), a light amount level of the infrared light source is gradually increased. Specifically, the light source level 1 indicates that a light amount is smallest. The light amount increases as the light source level increases. The light source level 4 indicates that the light amount is largest. As the light source level increases by one, a control voltage of the light source increases by approximately 0.5 V. The circles in each of the graphs illustrated in FIG. 13 represent peak positions (top points) of a pulse wave. In a case where the light amount of the light source is small as in FIG. 13(a), more noise is contained than infrared light from the infrared light source, and it is therefore difficult to specify a pulse wave timing. Meanwhile, in a case where the light amount of the light source is large as in FIGS. 13(c) and 13(d), a change in luminance of skin that occurs in accordance with a pulse wave is buried in the light amount of the light source. This reduces the shape of the pulse wave, thereby making it difficult to specify a pulse wave timing.

In a case where a pulse wave is obtained by using images taken in a visible light wavelength range by irradiation of visible light, a pulse wave can be sufficiently obtained even in a case where visible light of a light amount that is not too strong for human eyes is emitted. However, in a case where a pulse wave is obtained by using images taken in an infrared light wavelength range by irradiation of infrared light, noise is contained or the light amount of the infrared light becomes too large as described above even in a case where the light amount of the infrared light is controlled. It is therefore difficult to obtain a pulse wave unless the light amount is in a limited range. Furthermore, even in a case where the light amount of the infrared light source is preset to a predetermined value, a proper light amount changes depending on an obtained skin portion, a user's skin type, a skin color, and the like. It is therefore difficult to preset a proper light amount. It is therefore necessary to control the light amount of infrared light to a proper value by using the correlation value computing unit 113 described below while decreasing the light amount of visible light so that a visible light wave and an infrared light wave match each other.

Correlation Value Computing Unit

The correlation value computing unit 113 computes a correlation value between a visible light wave obtained from the visible light wave computing unit 111 and an infrared light wave obtained from the infrared light wave computing unit 112. Then, the correlation value computing unit 113 determines a command to adjust the light amount of the visible light source 121 and the light amount of the infrared light source 123 in accordance with the calculated correlation value and then supplies the determined command to the light source control unit 114.

The correlation value computing unit 113 obtains a plurality of first heartbeat time intervals calculated from a first visible light wave and a plurality of second heartbeat time interval calculated from a first infrared light wave from the visible light wave computing unit 111 and the infrared light wave computing unit 112, respectively. Then, the correlation value computing unit 113 computes a first correlation value between the plurality of first heartbeat time intervals and the plurality of second heartbeat time intervals that correspond to each other in a time sequence.

Figure 14:
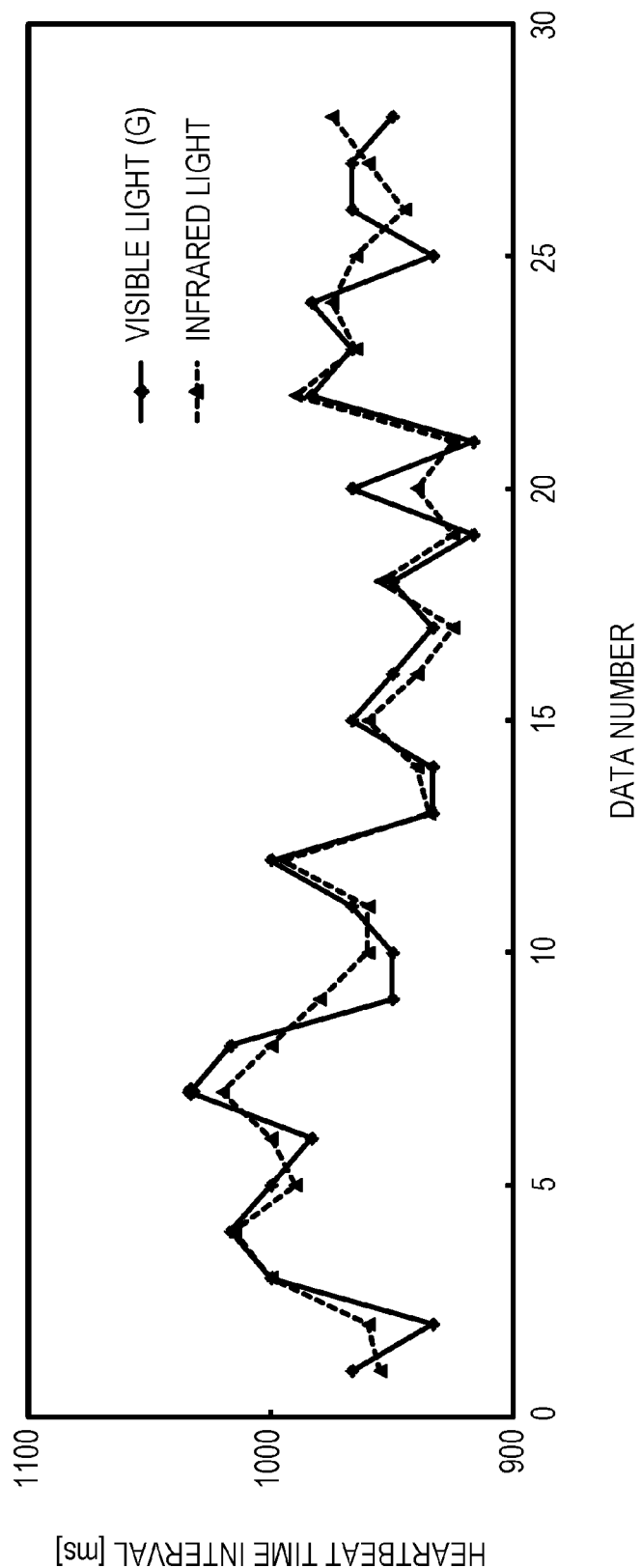
FIG. 14 is a graph plotting, in a time sequence, data of first heartbeat time intervals and second heartbeat time intervals.

Furthermore, the correlation value computing unit 113 obtains a plurality of third heartbeat time intervals calculated from a second visible light wave and a plurality of fourth heartbeat time intervals calculated from a second infrared light wave from the visible light wave computing unit 111 and the infrared light wave computing unit 112, respectively. Then, the correlation value computing unit 113 may compute a second correlation value between the plurality of third heartbeat time intervals and the plurality of fourth heartbeat time intervals that correspond to each other in a time sequence, FIG. 14 is a graph plotting first heartbeat time intervals and second heartbeat time intervals in a time sequence. In the graph illustrated in FIG. 14, the horizontal axis represents a data number in a time sequence, and the vertical axis represents a heartbeat time interval corresponding to the data number. The data number is an order in which data of a heartbeat time interval is recorded on a memory. Specifically, a data number corresponding to an n-th (n is a natural number) recorded first heartbeat time interval is "n". Furthermore, a data number corresponding to an nth (n is a natural number) recorded second heartbeat time interval is "n". Furthermore, it can be said that a first heartbeat time interval and a second heartbeat time interval that are given the same data number, which are results of measurement of a pulse wave at the same timing, are results of measurement of a pulse wave at almost the same timing as long as there is no measurement error. That is, the plurality of first heartbeat time intervals and the plurality of second heartbeat time intervals includes a single pair of first heartbeat time interval and second heartbeat time interval that correspond to each other in a time sequence.

The correlation value computing unit 113 computes a correlation value between the plurality of first heartbeat time intervals and the plurality of second heartbeat time intervals by using a correlation method. Specifically, the correlation value computing unit 113 computes, as a first correlation value, a first correlation coefficient between the plurality of first heartbeat time intervals and the plurality of second heartbeat time intervals that correspond to each other in a time sequence by using the following equation 1:

$$\rho 1 = \frac{\sigma_{12}}{\sigma_1 \sigma_2} \qquad \text{equation 1}$$

σ1: the first correlation coefficient
$\sigma_{12}$: a covariance of the plurality of first heartbeat time intervals and the plurality of second heartbeat time intervals
$\sigma_1$: a first standard deviation that is a standard deviation of the plurality of first heartbeat time intervals
$\sigma_2$: a second standard deviation that is a standard deviation of the plurality of second heartbeat time intervals Furthermore, the correlation value computing unit 113 computes, as a second correlation value, a second correlation coefficient between the plurality of third heartbeat time intervals and the plurality of fourth heartbeat time intervals that correspond to each other in a time sequence by using the following equation 2:

$$\rho 2 = \frac{\sigma_{34}}{\sigma_3 \sigma_4} \qquad \text{equation 2}$$

ρ2: the second correlation coefficient
$\sigma_{34}$: a covariance of the plurality of third heartbeat time intervals and the plurality of fourth heartbeat time intervals
$\sigma_3$: a third standard deviation that is a standard deviation of the plurality of third heartbeat time intervals
$\sigma_4$: a fourth standard deviation that is a standard deviation of the plurality of fourth heartbeat time intervals The correlation value computing unit 113 determines that the plurality of first heartbeat time intervals and the plurality of second heartbeat time intervals roughly match each other, for example, in a case where the first correlation coefficient is equal to or larger than a second threshold value (e.g., 0.8). Then, the correlation value computing unit 113 transmits, for example, a "TRUE" signal to the light source control unit 114 as a signal indicating that the plurality of first heartbeat time intervals and the plurality of second heartbeat time intervals roughly match each other. Meanwhile, the correlation value computing unit 113 determines that the plurality of first heartbeat time intervals and the plurality of second heartbeat time intervals do not match each other in a case where the correlation coefficient is smaller than the second threshold value (e.g., 0.8). Then, the correlation value computing unit 113 transmits, for example, a "FALSE" signal to the light source control unit 114 as a signal indicating that the plurality of first heartbeat time intervals and the plurality of second heartbeat time intervals do not match each other. The correlation value computing unit 113 also performs the aforementioned process on the second correlation coefficient as in the case of the first correlation coefficient.

Furthermore, the correlation value computing unit 113 may determine not only a correlation value between the first heartbeat time intervals and the second heartbeat time intervals, but also whether or not each heartbeat time interval is proper and then transmit a result of the determination to the light source control unit 114. Specifically, the correlation value computing unit 113 determines whether or not an absolute error between a first heartbeat time interval and a second heartbeat time interval that correspond to each other in a time sequence among the plurality of first heartbeat time intervals and the plurality of second heartbeat time intervals is larger than a third threshold value (e.g., 200 ms). For example, the correlation value computing unit 113 calculates an absolute error between a first heartbeat time interval and a second heartbeat time interval that have the same data number and determines whether or not this absolute error is larger than the third threshold value. Then, for example, the correlation value computing unit 113 determines that the number of peak points of a visible light wave or an infrared light wave is excessive in a case where the correlation value computing unit 113 determines that the absolute error is larger than the third threshold value. Then, the correlation value computing unit 113 transmits a wave (the visible light wave or the infrared light wave) having the excessive number of peak points to the light source control unit 114. The absolute error is computed by the following equation 3:

$$E = RRI_{RGB} - RRI_{IR} \qquad \text{equation 3}$$

In the equation 3, e represents an absolute error between a first heartbeat time interval and a second heartbeat time interval that correspond to each other, $RRI_{RGB}$ represents the first heartbeat time interval, and $RRI_{IR}$ represents the second heartbeat time interval.

Furthermore, the correlation value computing unit 113 determines that the number of peak points of visible light is excessive in a case where e is smaller than (−1)×the third threshold value (e.g., −200 ms), whereas the correlation value computing unit 113 determines that the number of peak points of infrared light is excessive in a case where e is larger than the third threshold value (e.g., 200 ms). Then, the correlation value computing unit 113 transmits, as a result of the determination, information indicating which of the visible light wave and the infrared light wave has the excessive number of peak points to the light source control unit 114. In this way, it can be specified, from a difference between heartbeat time intervals corresponding to the two waves, that an excessive number of peak points have been obtained in any of the waves or that failure to obtain peak points has occurred.

For example, in a case where the correlation value computing unit 113 determines that an absolute error between a first heartbeat time interval and a second heartbeat time interval that correspond to each other is larger than the third threshold value and that an excessive number of peak points have been obtained in a visible light wave, the correlation value computing unit 113 trans a "FALSE, RGB" signal indicative of the result of the determination to the light source control unit 114. In a case where the correlation value computing unit 113 determines that the absolute error is larger than the third threshold value and that an excessive number of peak points have been obtained in an infrared light wave, the correlation value computing unit 113 transmits "FALSE, IR" indicative of the result of the determination to the light source control unit 114.

Figure 15:
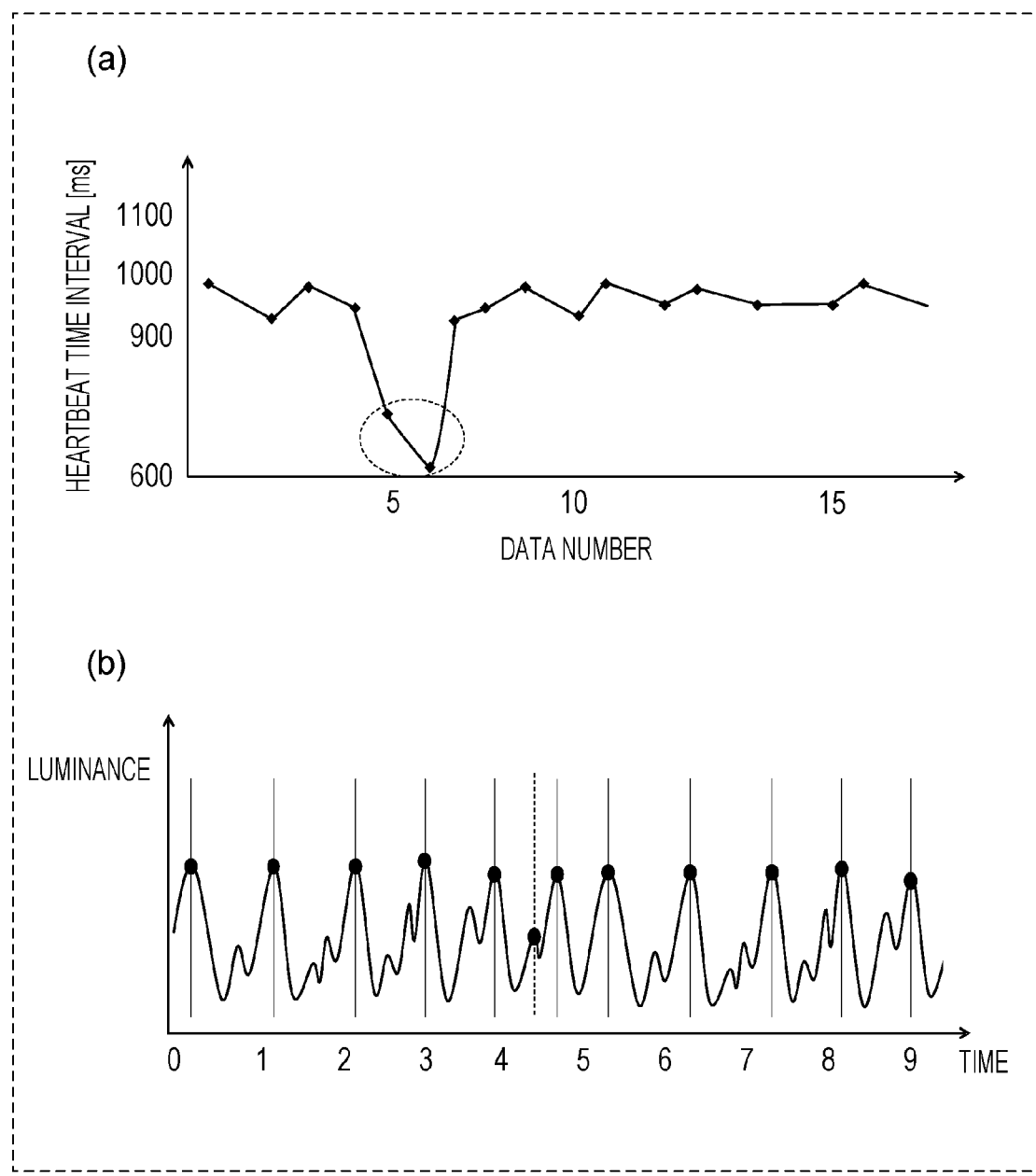
FIG. 15 is a diagram for explaining a specific example of a determining process for determining whether or not a heartbeat time interval is proper.

FIG. 15 is a diagram for explaining a specific example of the process for determining whether or not a heartbeat time interval is proper. FIG. 15(a) is a graph illustrating a case where a plurality of obtained heartbeat time intervals are not proper. FIG. 15(b) is a graph illustrating an example of a visible light wave or an infrared light wave corresponding to FIG. 15(a). In the graph of FIG. 15(a), the horizontal axis represents a data number in a time sequence, and the vertical axis represents a heartbeat time interval that corresponds to the data number. In the graph of FIG. 15(b), the horizontal axis represents a time, and the vertical axis represents luminance in an image.

In FIG. 15(a), two heartbeat time intervals surrounded by the dotted line is a portion that is not proper. A heartbeat time interval generally fluctuates, but hardly fluctuates rapidly. For example, in a region other than the portion surrounded by the dotted line in FIG. 15(a), an average of heartbeat time intervals is approximately 950 ms, and a standard deviation thereof is approximately 50 ms. However, the two heartbeat time intervals surrounded by the dotted line have approximately 600 ms to 700 ms. That is, there is a rapid change in value. This rapid change occurs because the portion indicated by the broken line in FIG. 15(b) has been obtained as a peak point. That is, this rapid change occurs because the visible light wave computing unit 111 or the infrared light wave computing unit 112 has obtained an excessive number of peak points.

In a case where a result like the one illustrated in FIG. 15 is obtained only in the visible light wave computing unit 111 or the infrared light wave computing unit 112, the number of pieces of data of the plurality of first heartbeat time intervals and the number of pieces of data of the plurality of second heartbeat time intervals do not match as a result of comparison.

Figure 16:
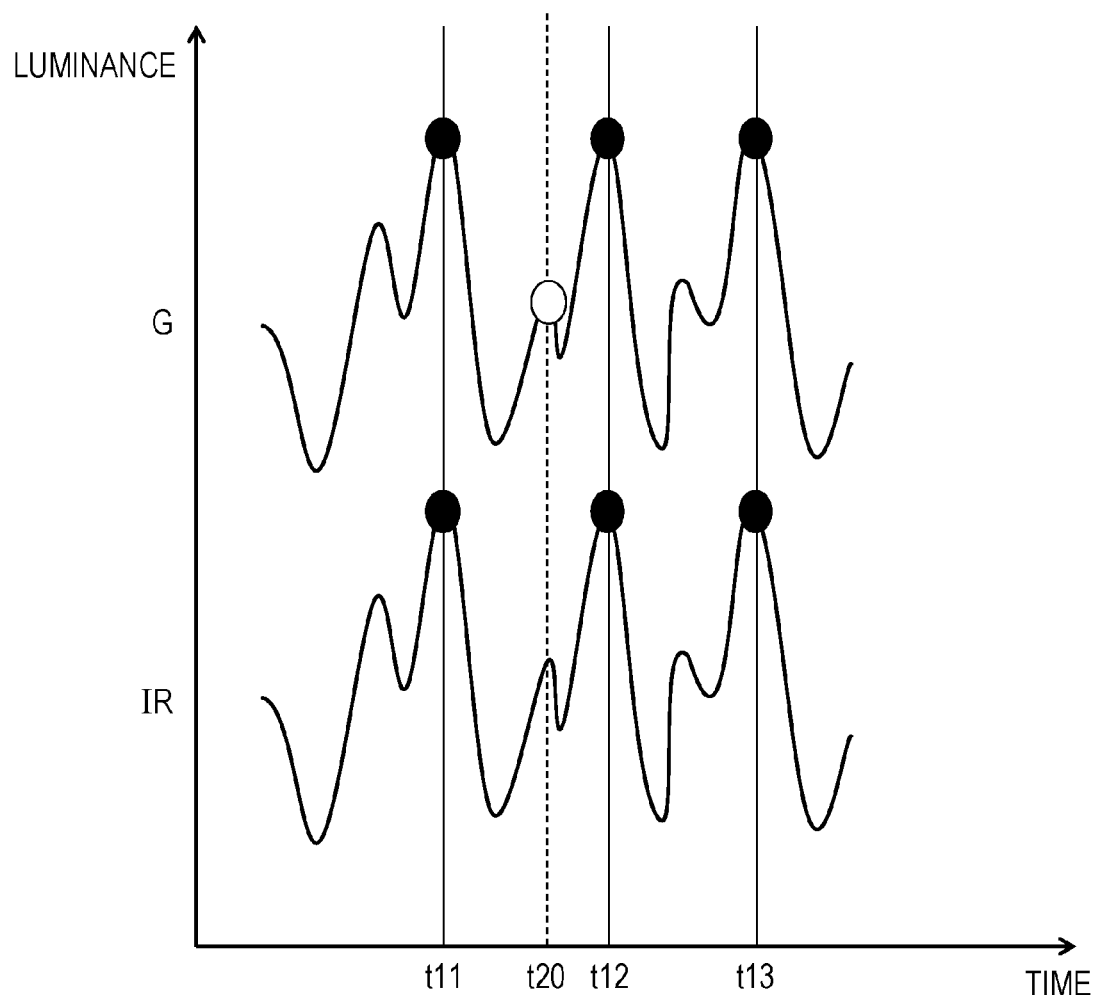
FIG. 16 is a diagram illustrating an example of a case where an excessive number of peak points have obtained in a visible light wave and where an excessive number of peak points have not been obtained in a corresponding infrared light wave.

FIG. 16 illustrates this state. FIG. 16 is a diagram for explaining an example of a case where an excessive number of peak points have been obtained in a visible light wave and an excessive number of peak points have not been obtained in a corresponding infrared light wave, Data of a plurality of first or second heartbeat time intervals are stored in the storage 103, for example, in a format (data No, heartbeat time interval). Data indicative of a plurality of first heartbeat time intervals obtained in a visible light wave are, for example, (x, t20−t11), (x+1, t12−t20), and (x+2, t13−t12). Data indicative of a plurality of second heartbeat time intervals obtained in an infrared light wave are, for example, (x, t12−t11) and (x+1, t13−t12). When the data obtained in the visible light wave and the data obtained in the infrared light wave are compared, the number of data obtained in the visible light wave and the number of data obtained in the infrared light wave are different although the data are obtained in the same time interval t11 to t13. This causes a discrepancy in all of subsequent correspondences between data of the first heartbeat time intervals and data of the second heartbeat time intervals, thereby deviating a correlation value between time-fluctuating heartbeat time intervals.

Accordingly, the correlation value computing unit 113 deletes a single pulse wave peak from a wave having a larger number of peak points in a case where an absolute error, calculated for each data number, between third and fourth heartbeat time intervals obtained by the visible light wave computing unit 111 and the infrared light wave computing unit 112 is equal to or larger than the third threshold value, e.g., 200 ms. Then, the correlation value computing unit 113 subtracts one from each of data numbers after the data number corresponding to the deleted peak.

As described above, in a case where it is determined that an excessive number of peak points (i.e., predetermined feature points) have been obtained, the correlation value computing unit 113 may exclude a predetermined feature point used for computation of a heartbeat time interval in a wave (a visible light wave or an infrared light wave) having a larger number of predetermined feature points from computation of the heartbeat time interval. Specifically, in a case where e is smaller than (−1)×the third threshold value, the correlation value computing unit 113 excludes a peak point used for computation of $RRI_{RGB}$ used to calculate e from computation of the first heartbeat time interval. In a case where e is larger than the third threshold value, the correlation value computing unit 113 excludes a peak point used for computation of $RRI_{IR}$ used to calculate e from computation of the second heartbeat time interval.

That is, the correlation value computing unit 113 determines whether or not an absolute error between a third heartbeat time interval and a fourth heartbeat time interval that correspond to each other in a time sequence among a plurality of third heartbeat time intervals and a plurality of fourth heartbeat time intervals is larger than the third threshold value. Then, in a case where it is determined that the absolute error is larger than the third threshold value, the correlation value computing unit 113 compares the number of third peak points and the number of fourth peak points. The correlation value computing unit 113 specifies which of the third heartbeat time interval and the fourth heartbeat time interval for which the absolute error is larger than the third threshold value is a heartbeat time interval calculated by using a peak point of a wave determined to have a larger number of peak points as a result of the comparison. The correlation value computing unit 113 excludes the peak point used for computation of the specified heartbeat time interval from computation of the specified heartbeat time interval.

An excessive number of peak points are obtained because an obtained wave (a visible light wave or an infrared light wave) contains much noise. In view of this, it is determined whether the wave in which an excessive number of peak points have been obtained is a visible light wave or an infrared light wave, and a signal such as a "FALSE, RGB" signal is generated as described above and is then transmitted to the light source control unit 114. That is, in a case where the light source control unit 114 receives a "FALSE, RGB" signal, the light source control unit 114 finds that heartbeat time intervals of a visible light wave and heartbeat time intervals of an infrared light wave do not match each other and that a cause of the mismatch lies in the visible light wave. In this way, a data discrepancy between peak points obtained in the visible light wave and peak points obtained in the infrared light wave can be grasped, and information on the grasped result can be transmitted to the light source control unit 114. It is therefore possible to more accurately obtain a user's pulse wave in the visible light wave and the infrared light wave.

In the above description, the second threshold value used in the process for determining a correlation value between first heartbeat time intervals and second heartbeat time intervals by the correlation value computing unit 113 is 0.8. However, the present embodiment is not limited to this. Specifically, the second threshold value may be changed depending on desired accuracy of biological information measured by a user. For example, in a case where a user wants to more accurately obtain biological information during sleep such as a heartbeat or a blood pressure by precisely extracting a pulse wave by using infrared light during sleep, the second threshold value used as a criteria in the determining process may be made larger, for example, 0.9.

In a case where the second threshold value used as the criteria concerning a correlation coefficient is adjusted, reliability of obtained data may be displayed on a presenting device 40 in accordance with the adjusted second threshold value. For example, in a case where match in features between a visible light wave and an infrared light wave cannot be achieved and therefore the amount of light emitted from a visible light source cannot be reduced during sleep, the second threshold value used as the criteria concerning a correlation coefficient may be changed to a value (e.g., 0.6) smaller than 0.8. In this case, accuracy concerning a correlation value decreases, and therefore a decrease in reliability may be displayed on the presenting device 40.

The correlation value computing unit 113 may determine a correlation value between a visible light wave and an infrared light wave by using inflection points of the visible light wave and the infrared light wave in a case where a correlation coefficient between first and second heartbeat time intervals obtained in a time sequence from the visible light wave and the infrared light wave is smaller than the second threshold value or in a case where an excessive number of peak points has been obtained within a first predetermined period in the visible light wave computing unit 111 and the infrared light wave computing unit 112. That is, a plurality of third heartbeat time intervals may be calculated by using first inflection points, and a plurality of fourth heartbeat time intervals may be calculated by using second inflection points. Then, a correlation coefficient between the plurality of third heartbeat time intervals and the plurality of fourth heartbeat time intervals that correspond to each other in a time sequence may be computed as a second correlation coefficient by using equation 2.

Specifically, the correlation value computing unit 113 may determine a correlation value between time interval information indicative of time intervals between inflection points in a visible light wave and time interval information indicative of time intervals between inflection points in an infrared light wave in a case where a correlation coefficient between first heartbeat time intervals in the visible light wave and second heartbeat time intervals in the infrared light wave is smaller than the second threshold value (e.g., 0.8) or in a case where the number of peak points obtained by the visible light wave computing unit 111 and the number of peak point obtained by the infrared light wave computing unit 112 do not match within a first predetermined interval (e.g., 5 seconds) and the number of peak points in at least one of the visible light wave and the infrared light wave is larger than a first threshold value (e.g., 10).

That is, the correlation value computing unit 113 performs a tenth determining process for determining whether or not the number of third peak points or the number of fourth peak points within the first predetermined period is larger than the first threshold value. The correlation value computing unit 113 may perform the following process in a case where it is determined that the number of third peak points or the number of fourth peak points within the first predetermined period is larger than the first threshold value.

Specifically, the correlation value computing unit 113 causes the visible light wave computing unit 111 to extract a plurality of first inflection points by extracting, for each of the plurality of third top points, a first inflection point that is an inflection point between the third top point and a third bottom point that immediately follows the third top point in a time sequence among the plurality of third bottom points. Furthermore, the correlation value computing unit 113 causes the infrared light wave computing unit 112 to extract a plurality of second inflection point by extracting, for each of the plurality of fourth top points, a second inflection point that is an inflection point between the fourth top point and a fourth bottom point that immediately follows the fourth top point in a time sequence among the plurality of fourth bottom points. Furthermore, the correlation value computing unit 113 causes the visible light wave computing unit 111 to calculate, for each of the plurality of extracted first inflection points, a third heartbeat time interval that is a time interval between a ninth time point of the first inflection point and a tenth time point of another first inflection point adjacent to the first inflection point. Furthermore, the correlation value computing unit 113 causes the infrared light wave computing unit 112 to calculate, for each of the plurality of extracted second inflection points, a fourth heartbeat time interval that is a time interval between a seventh time point of the second inflection point and an eighth time point of another second inflection point adjacent to the second inflection point. Then, the correlation value computing unit 113 computes, as a second correlation value, a second correlation coefficient between (i) the plurality of third heartbeat time intervals, calculated by using the first inflection points, and (ii) the plurality of fourth heartbeat time intervals, calculated by using the second inflection points, that correspond to each other in a time sequence by using equation 2.

In the following case, the correlation value computing unit 113 may compute, as a second correlation value, a second correlation coefficient between a plurality of third heartbeat time intervals calculated by using the first inflection points and a plurality of fourth heartbeat time interval calculated by using the second inflection points by using formula 2 as described above irrespective of a result of the tenth determining process. This case is a case where a standard deviation of heartbeat time intervals calculated from peak points of a wave that has been determined to have a smaller number of peak points as a result of comparison is equal to or larger than a fourth threshold value.

Figure 17:
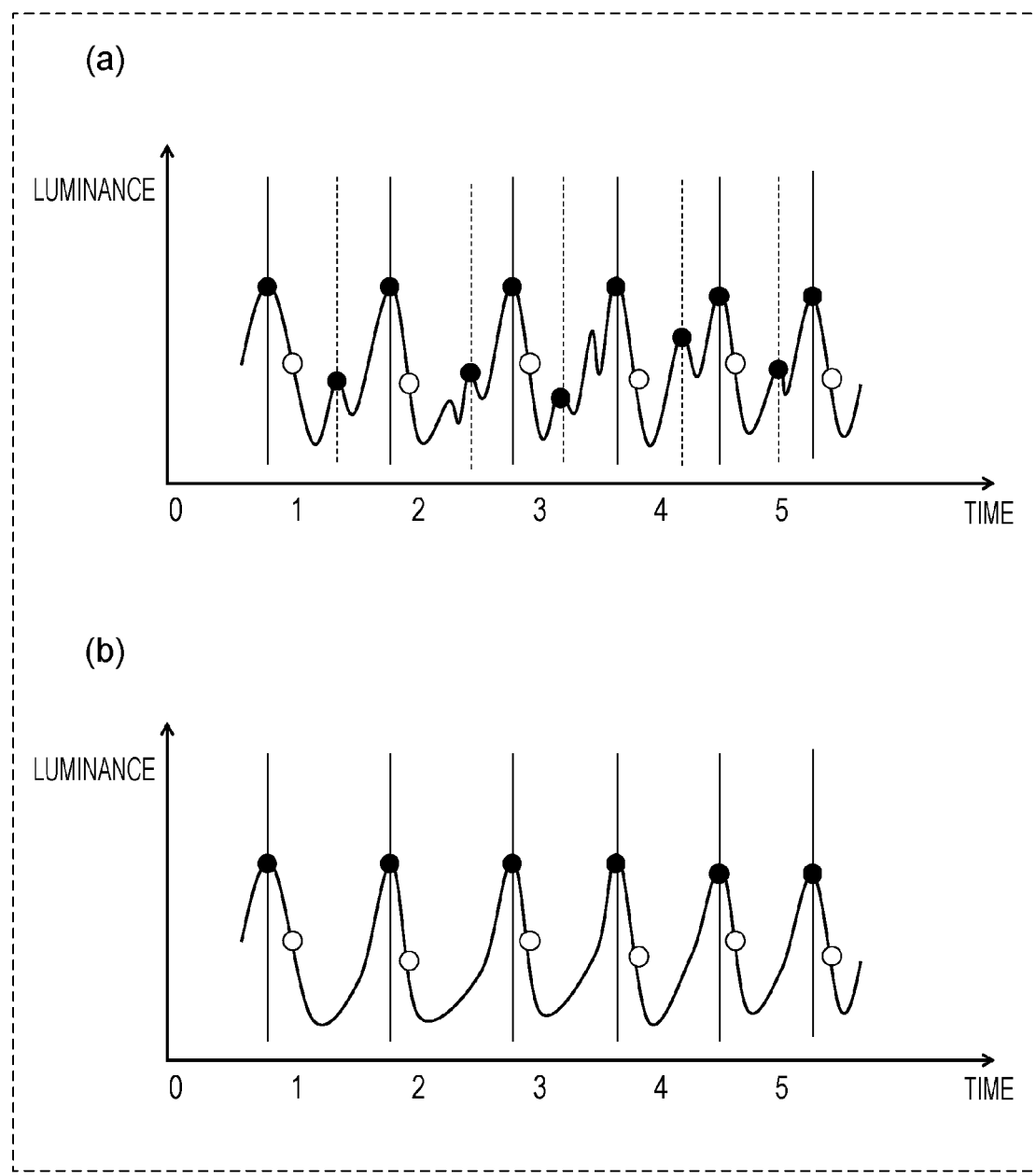
FIG. 17 is a diagram for explaining a case where a correlation value is calculated by using inflection points.

FIG. 17 is a diagram for explaining a case where a correlation value is calculated by using inflection points. FIG. 17(*a*) is a graph illustrating peak points (top points) obtained in a visible light wave, and FIG. 17(*b*) is a graph illustrating peak points (top points) obtained in an infrared light wave. In FIGS. 17(*a*) and 17(*b*), the horizontal axis represents a time, the vertical axis represents luminance, the black circles represent obtained top points, and the white circles represent obtained inflection points.

In FIG. 17(*a*), an excessive number of peak points have been obtained in a visible light wave. Specifically, the number of peak points within the first predetermined period (five seconds) is 10 or 11, which is equal to or larger than the first threshold value. Meanwhile, in FIG. 17(*b*), peak points have been obtained in an infrared light wave at a constant heartbeat time interval, and a standard deviation is 100 ms or smaller. In this case, a discrepancy occurs between time-series data numbers indicative of the first heartbeat time intervals in the visible light wave and time-series data numbers indicative of the second heartbeat time intervals in the infrared light wave.

Therefore, the correlation value computing unit 113 may compute a correlation value between the visible light wave and the infrared light wave by using inflection points that are obtained by the visible light wave computing unit 111 and the infrared light wave computing unit 112 and each of which is located between a top point and a bottom point of a pulse wave. For example, the correlation value computing unit 113 causes the visible light wave computing unit 111 and the infrared light wave computing unit 112 to calculate first heartbeat time intervals and second heartbeat time intervals, respectively, by using inflection points and then computes a correlation value between the first heartbeat time intervals and the second heartbeat time intervals. As a specific computing method, the correlation value computing unit 113 makes an evaluation by using correlation and/or an absolute error between a heartbeat time interval between inflection points of the visible light wave and a heartbeat time interval between inflection points of the infrared light wave.

In the above description, the correlation value computing unit 113 computes a correlation value between a visible light wave and an infrared light wave by using heartbeat time intervals between inflection points in a case where a correlation coefficient between heartbeat time intervals in the visible light wave and heartbeat time intervals in the infrared light wave is smaller than the second threshold value or in a case where the number of peak points in at least one of the visible light wave and the infrared light wave within the first predetermined period is larger than the first threshold value. However, the present embodiment is not limited to this. For example, the correlation value computing unit 113 may compute a correlation value between the visible light wave and the infrared light wave by using heartbeat time intervals between inflection points from the start without using peak points. This makes it possible to calculate time intervals that are similar to heartbeat time intervals by calculating heartbeat time intervals between inflection points even in a case where peak points cannot be accurately obtained from the visible light wave or the infrared light wave. However, although a heartbeat time interval between inflection points tends to contain less noise than a heartbeat time interval obtained from peak points, an inflection point easily fluctuates between a top point and a bottom point. That is, a heartbeat time interval between top points tends to be stable (for example, a standard deviation thereof tends to be within 100 ms) and tends to be smaller in terms of a time error than a heartbeat time interval between inflection points. For this reason, in the present disclosure, a heartbeat time interval computed from peak points are preferentially used unless otherwise specified.

The correlation value computing unit 113 may compute a correlation value by using heartbeat time intervals between inflection points instead of heartbeat time intervals computed from peak points in a case where the following condition is met irrespective of the above determining process. The condition is, for example, that a standard deviation of heartbeat time intervals in one of a visible light wave and an infrared light wave that has a smaller number of peak points is equal to or smaller than the fourth threshold value (e.g., 100 ms). This is because in a case where it is determined whether or not an excessive number of peak points have been obtained on the basis of the number of peak points within the first predetermined period, there is a possibility that an excess in the number of obtained peak points may be overlooked because the condition that the number of peak points within the first predetermined period is larger than the first threshold value is not met even though the number of peak points is actually excessive.

Figure 18:
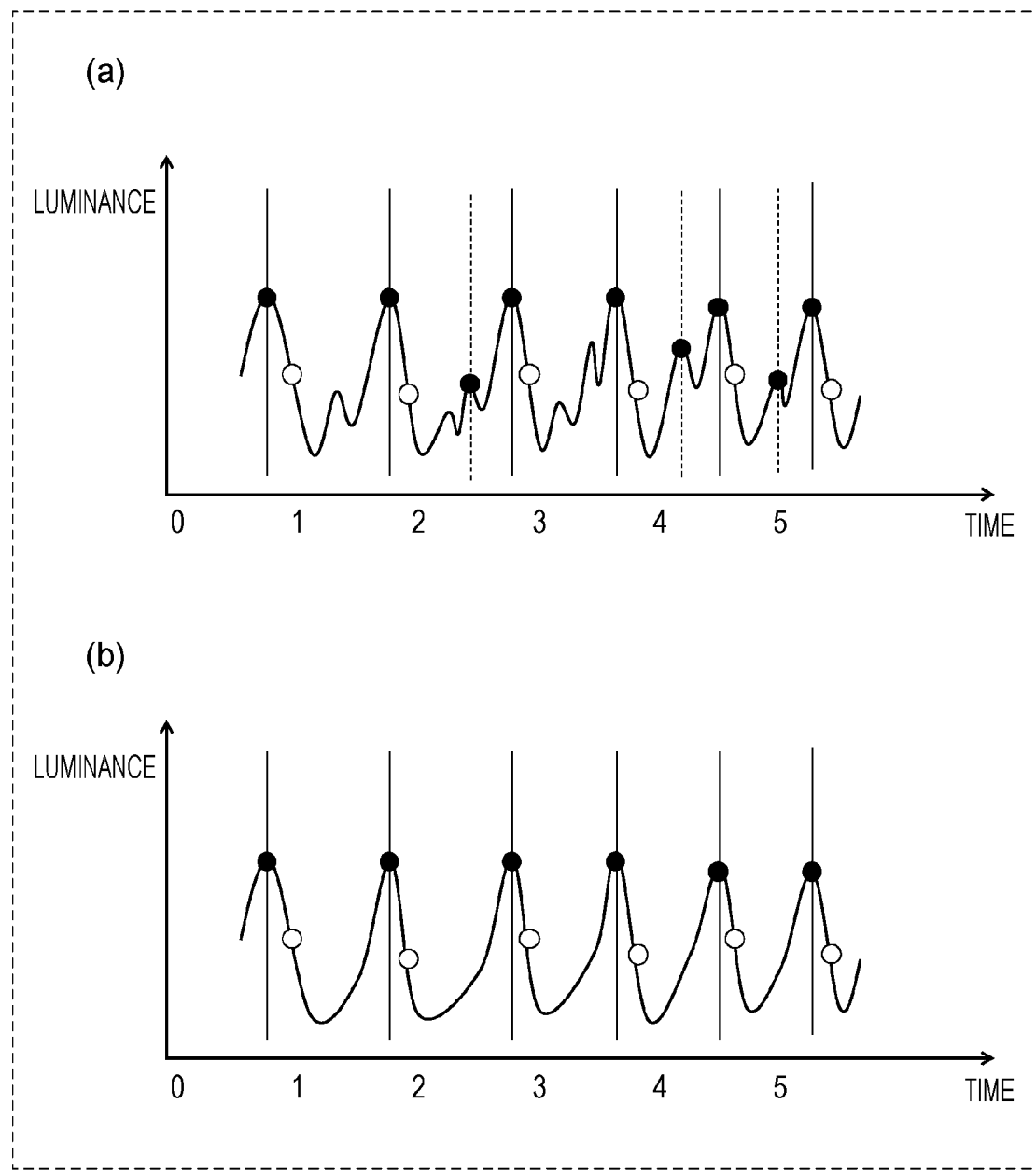
FIG. 18 is a diagram for explaining an example in which a condition that the number of peak points within a first predetermined period is larger than a first threshold value is not met although the number of peak points is excessive.

For example, FIG. 18 is a diagram for explaining an example in which the condition that the number of peak points within the first predetermined period is larger than the first threshold value is not met although the number of peak points is excessive. In FIGS. 18(a) and 18(b), the horizontal axis represents a time, the vertical axis represents luminance, the black circles represent obtained top points, and the white circles represent obtained inflection points.

In a case where the number of peak points obtained within five seconds in a visible light wave is 8 as illustrated in FIG. 18(a), the number of peak points obtained in the visible light wave is different from the number of peak points obtained in an infrared light wave illustrated in FIG. 18(b) although the condition that the number of peak points within the first predetermined period is larger than the first threshold value is not met. Even a single excessive peak point undesirably causes each of data numbers of first heartbeat time intervals to be deviated by one from a corresponding one of data numbers of second heartbeat time intervals. In view of this, as long as it can be determined that heartbeat time intervals in one of the visible light wave and the infrared light wave are almost constant, the number of peak points can be adjusted (a peak point can be deleted) in accordance with the number of peak points in the one of the visible light wave and the infrared light wave. Details of the adjustment of the number of peak points have been described above with reference to FIG. 16.

The correlation value computing unit 113 determines that a proper pulse wave timing cannot be obtained in both of a visible light wave and an infrared light wave in a case where a standard deviation of heartbeat time intervals within the first predetermined period is larger than the fourth threshold value in both of the visible light wave and the infrared light wave, and then the correlation value computing unit 113 supplies a "FALSE, BOTH" signal indicative of failure to obtain a proper pulse wave timing from both of the waves to the light source control unit 114.

The correlation value computing unit 113 causes the visible light wave computing unit 111 to compute a slope between a top point and a bottom point of a visible light wave and then causes the computed slope to be stored as a first slope A in a memory at the start of use of the pulse wave measuring device 10 in a case where peak points have been properly obtained within the first predetermined period by the visible light wave computing unit 111 (i.e., a standard deviation of heartbeat time intervals is smaller than the fourth threshold value). Then, the correlation value computing unit 113 sends a command to the light source control unit 114 so that a second slope between a top point and a bottom point of an infrared light wave becomes the first slope A every time the light amount of the visible light source 121 or the light amount of the infrared light source 123 is changed by the light source control unit 114. Furthermore, the correlation value computing unit 113 need not use, for computation of a correlation value between the visible light wave and the infrared light wave, peak points obtained during adjustment of the light amount of a light source by the light source control unit 114.

Figure 19:
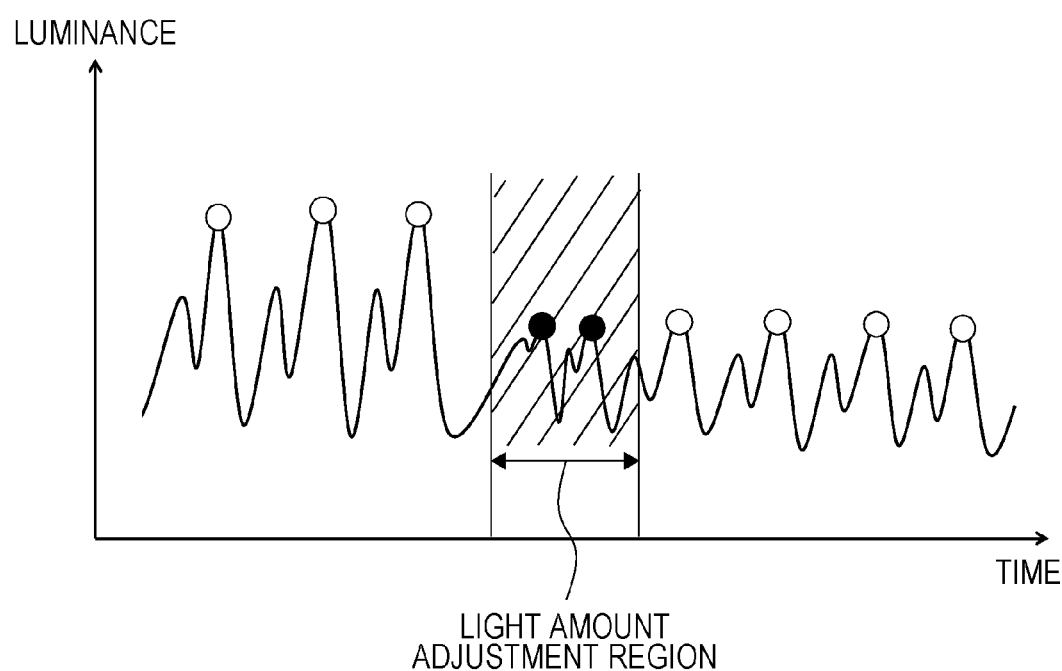
FIG. 19 is a diagram illustrating an example for explaining that a peak point obtained during adjustment of a light amount of a light source is not used for computation of a correlation value between a visible light wave and an infrared light wave.

FIG. 19 is a diagram illustrating an example for explaining that peak points obtained during adjustment of a light amount of a light source are not used for computation of a correlation value between a visible light wave and an infrared light wave. In the graph of FIG. 19, the horizontal axis represents a time, the vertical axis represents luminance, and the region with the diagonal lines indicates a region where a light amount of a light source is adjusted. The white circles and the black circles represent obtained peak points.

As illustrated in FIG. 19, in a case where a light amount of a light source is adjusted, a gain of luminance of a visible light wave or an infrared light wave changes, and sharpness of a peak point also changes accordingly. In a case where the peak point whose sharpness has been changed is filtered in the visible light wave computing unit 111 or the infrared light wave computing unit 112, the position of the peak point changes forward or backward on the temporal axis depending on sharpness of the peak of the raw wave that has not been filtered. This error does not pose a problem in a case where a heart rate is calculated as biological information but has large influence, for example, in a case where a blood pressure is calculated from a pulse wave propagation period. In view of this, the pulse wave measuring device 10 of the present disclosure need not extract a predetermined feature point (i.e., peak point) from a visible light wave or an infrared light wave obtained during control of the light amount of the visible light source 121 or the infrared light source 123 based on first through fourth control signals (described later).

That is, the visible light wave computing unit 111 extracts a plurality of first peak points from a first visible light wave obtained during a period excluding a period in which the light amount of the visible light source 121 is controlled on the basis of the first control signal. Furthermore, the visible light wave computing unit 111 extracts a plurality of third peak points from a second visible light wave obtained during a period excluding a period in which the light amount of the visible light source 121 is controlled on the basis of the third control signal.

The infrared light wave computing unit 112 extracts a plurality of second peak points from a first infrared light wave obtained during a period excluding a period in which the light amount of the infrared light source 123 is controlled on the basis of the second control signal. Furthermore, the infrared light wave computing unit 112 extracts a plurality of fourth peak points from a second infrared light wave obtained during a period excluding a period in which the light amount of the infrared light source 123 is controlled on the basis of the fourth control signal.

In the above description, in a case where a correlation coefficient between heartbeat time intervals in a visible light wave and heartbeat time intervals in an infrared light wave is smaller than the second threshold value, the correlation value computing unit 113 determines that the number of peak points in one of the waves or in both of the waves is excessive, calculates an error between heartbeat time intervals and/or a standard deviation of heartbeat time intervals, and uses heartbeat time intervals between inflection points each located between a top point and a bottom point of a wave in a case where the predetermined condition is met. However, the present embodiment is not limited to this. For example, the correlation value computing unit 113 transmits a "FALSE" signal to the light source control unit 114 in a case where peak points have been properly obtained in both of the waves (e.g., the standard deviations of heartbeat time intervals in both of the waves are equal to or smaller than the fourth threshold value) although a correlation coefficient between first heartbeat time intervals and second heartbeat time intervals is smaller than the second threshold value.

In this way, the correlation value computing unit 113 transmits, to the light source control unit 114, a signal (e.g., "TRUE", "FALSE", " FALSE, RGB", FALSE, IR", or "FALSE, BOTH") corresponding to a computed correlation value and a result of extraction of predetermined feature points from a visible light wave and an infrared light wave.

As described above, the correlation value computing unit 113 performs the following determining processes on the basis of first heartbeat time intervals and second heartbeat time intervals.

Specifically, the correlation value computing unit 113 performs a second determining process for determining whether or not the first standard deviation is larger than the fourth threshold value and the second standard deviation is larger than the fourth threshold value. In a case where it is determined as a result of the second determining process that the first standard deviation is larger than the fourth threshold value and the second standard deviation is larger than the fourth threshold value, the correlation value computing unit 113 performs a third determining process for determining whether or not a first time difference between one of a plurality of first heartbeat time intervals and one of a plurality of second heartbeat time intervals that corresponds, in a time sequence, to the one first heartbeat time interval is smaller than a fifth threshold value and a fourth determining process for determining whether or not the first time difference is larger than a sixth threshold value that is larger than the fifth threshold value.

Meanwhile, in a case where it is determined as a result of the third determining process and the fourth determining process that the first time difference is smaller than the fifth threshold value, the correlation value computing unit 113 performs a fifth determining process for determining whether or not the second standard deviation is equal to or smaller than the fourth threshold value.

The correlation value computing unit 113 may perform the following determining processes on the basis of third heartbeat time intervals and fourth heartbeat time intervals.

Specifically, the correlation value computing unit 113 may perform a sixth determining process for determining whether or not the third standard deviation is larger than the fourth threshold value and the fourth standard deviation is larger than the fourth threshold value. In a case where it is determined as a result of the sixth determining process that the third standard deviation is larger than the fourth threshold value and the fourth standard deviation is larger than the fourth threshold value, the correlation value computing unit 113 performs a seventh determining process for determining whether or not a second time difference between one of a plurality of third heartbeat time intervals and one of a plurality of fourth heartbeat time interval that corresponds, in a time sequence, to the one third heartbeat time interval is smaller than the fifth threshold value and an eighth determining process for determining whether or not the second time difference is larger than the sixth threshold value.

Meanwhile, in a case where it is determined as a result of the seventh determining process and the eighth determining process that the second time difference is smaller than the fifth threshold value, the correlation value computing unit 113 performs a ninth determining process for determining whether or not the fourth standard deviation is equal to or smaller than the fourth threshold value.

Light Source Control Unit

The light source control unit 114 decides to increase, decrease, or maintain at least one of the light amount of visible light emitted from the visible light source 121 and the light amount of infrared light emitted from the infrared light source 123 in accordance with a signal corresponding to a correlation value and a result of extraction received from the correlation value computing unit 113 and then supplies any of the first through fourth control signals that corresponds to a result of the decision to the visible light source 121 and the infrared light source 123.

In a case where the light source control unit 114 receives a "FALSE" signal, it can be determined that heartbeat time intervals in each wave have been properly obtained although a correlation coefficient between first heartbeat time intervals in a visible light wave and second heartbeat time intervals an infrared light wave is smaller than the second threshold value. In this case, the light source control unit 114 can determines that a signal of the infrared light wave is weak relative to the visible light wave and positions of peaks are deviated every time as a result of filtering processing or the like, for example, because of small sharpness of peak points although predetermined feature points can be obtained in each wave. Therefore, in this case, the light source control unit 114 increases the light amount of the infrared light source 123 until the second slope from a top point to a bottom point of the infrared light wave becomes the first slope A stored in the memory.

Meanwhile, in a case where the light source control unit 114 receives a "TRUE" signal, the light source control unit 114 can determine that predetermined feature points in the visible light wave and predetermined feature points in the infrared light wave match each other. Therefore, the light source control unit 114 decreases the light amount of visible light emitted from the visible light source 121 and increases the light amount of infrared light emitted from the infrared light source 123 until the second slope from a top point to a bottom point of the infrared light wave becomes the first slope A stored in the memory. That is, in a case where the correlation value is equal to or larger than the second threshold value, the light source control unit 114 increases the light amount of visible light emitted from the visible light source and increases the light amount of infrared light emitted from the infrared light source. In this case, the light source control unit 114 increases the light amount of infrared light until the second slope in the infrared light wave becomes the first slope A stored in the memory (the storage 103).

The process for obtaining second visible light images, the process for extracting a second visible light wave, the process for obtaining second infrared light images, the process for extracting a second infrared light wave, and the process for computing a second correlation coefficient are repeatedly performed by the processing units of the pulse wave computing device 100. In repeated computation of the second correlation coefficient, the light source control unit 114 compares the second slope and the first slope stored in the memory and supplies a second control signal to the infrared light source 123 until the second slope becomes the first slope.

In a case where the light source control unit 114 receives, for example, a "FALSE, IR" signal, the light source control unit 114 can determine that predetermined feature points have not been properly obtained in an infrared light wave by the infrared light wave computing unit 112. That is, for example, the "FALSE, IR" signal indicates that the infrared light wave contains much noise. For this reason, the light source control unit 114 increases the light amount of the infrared light source 123 without adjusting the light amount of the visible light source 121.

That is, in a case where it is determined as a result of the third determining process and the fourth determining process that an absolute error e that is the first time difference is larger than a sixth threshold value (200 [ms]), the light source control unit 114 supplies the second control signal to the infrared light source 123. In a case where it is determined as a result of the seventh determining process and the eighth determining process that an absolute error e that is the second time difference is larger than the sixth threshold value (200 [ms]), the light source control unit 114 supplies the second control signal to the infrared light source 123.

The light source control unit 114 increases the light amount of the infrared light source 123 by supplying the second control signal to the infrared light source 123.

In a case where the light source control unit 114 receives a "FALSE, RGB" signal, the light source control unit 114 can determine that predetermined feature points have not been properly obtained in a visible light wave by the visible light wave computing unit 111. In this case, the light source control unit 114 cannot determine whether or not predetermined feature points have been properly obtained in an infrared light wave by the infrared light wave computing unit 112. Therefore, for example, in a case where a standard deviation of heartbeat time intervals within the first predetermined period in the infrared light wave is equal to or smaller than the fourth threshold value, the light source control unit 114 decreases the light amount of the visible light source 121 and increases the light amount of the infrared light source 123 until a slope from a top point to a bottom point of the infrared light wave becomes the slope A. In a case where the standard deviation in the infrared light wave is larger than the fourth threshold value, the light source control unit 114 determines that neither a signal of the visible light wave nor a signal of the infrared light wave have been obtained and changes the signal to "FALSE, BOTH".

That is, in a case where it is determined as a result of the fifth determining process that the second standard deviation is equal to or smaller than the fourth threshold value, the light source control unit 114 supplies the first control signal to the visible light source 121 and supplies the second control signal to the infrared light source 123. In a case where it is determined that the second standard deviation is larger than the fourth threshold value, the light source control unit 114 supplies the third control signal to the visible light source 121 and supplies the fourth control signal to the infrared light source. The fifth determining process is a determining process performed in a case where it is determined as a result of the third determining process and the fourth determining process that the first time difference is smaller than the fifth threshold value and is a determining process for determining whether or not the second standard deviation is equal to or smaller than the fourth threshold value, as described above.

In a case where it is determined as a result of the ninth determining process that the fourth standard deviation is equal to or smaller than the fourth threshold value, the light source control unit 114 supplies the first control signal to the visible light source 121 and supplies the second control signal to the infrared light source 123. In a case where it is determined as a result of the ninth determining process that the fourth standard deviation is larger than the fourth threshold value, the light source control unit 114 supplies the third control signal to the visible light source 121 and supplies the fourth control signal to the infrared light source 123. The ninth determining process is a determining process performed in a case where it is determined as a result of the seventh determining process and the eighth determining process that the second time difference is smaller than the fifth threshold value and is a determining process for determining whether or not the fourth standard deviation is equal to or smaller than the fourth threshold value, as described above.

In a case where the light source control unit 114 receives a "FALSE, BOTH" signal, the light source control unit 114 can determine that predetermined feature points have been obtained in neither the visible light wave nor the infrared light wave. In this case, the light source control unit 114 increases the light amount of the visible light source 121 until a slope from a top point to a bottom point of the visible light wave becomes the first slope A. The light source control unit 114 may increase the light amount of the visible light source 121 until the light amount of the visible light wave becomes an initial light amount thereof in a case where the initial light amount is stored in the memory. Furthermore, the light source control unit 114 decreases the light amount of the infrared light source 123 to zero. That is, in a case where predetermined feature points can be obtained in neither the visible light wave nor the infrared light wave, the light source control unit 114 sets the light amount of the visible light source 121 and the light amount of the infrared light source 123 to the initial states, in which the predetermined feature points can be obtained with the most certainty, and adjust the light amounts again.

That is, in a case where it is determined as a result of the third determining process and the fourth determining process that an absolute error e that is the first time difference is not less than the fifth threshold value and not more than the sixth threshold value, the light source control unit 114 supplies the third control signal to the visible light source 121 and supplies the fourth control signal to the infrared light source 123. Furthermore, in a case where it is determined as a result of the seventh determining process and the eighth determining process that an absolute error e that is the second time difference is not less than the fifth threshold value and not more than the sixth threshold value, the light source control unit 114 supplies the third control signal to the visible light source 121 and supplies the fourth control signal to the infrared light source 123. The light source control unit 114 increases the light amount of the visible light source 121 by supplying the third control signal to the visible light source 121 and decreases the light amount of the infrared light source 123 by supplying the fourth control signal to the infrared light source 123.

That is, in a case where a standard deviation of a plurality of first heartbeat time intervals is larger than the fourth threshold value, where a standard deviation of a plurality of second heartbeat time interval is larger than the fourth threshold value, and where a difference between a first heartbeat time interval and a second heartbeat time interval that correspond to each other in a time sequence is smaller than the fifth threshold value ((−1)× the third threshold value), the light source control unit 114 decreases the light amount of the visible light emitted from the visible light source 121 and increases the light amount of the infrared light emitted from the infrared light source 123 until the second slope in the infrared light wave becomes the first slope A stored in the memory.

In a case where a standard deviation of a plurality of first heartbeat time intervals is larger than the fourth threshold value, where a standard deviation of a plurality of second heartbeat time interval is larger than the fourth threshold value, and where a difference between a first heartbeat time interval and a second heartbeat time interval that correspond to each other in a time sequence is larger than the sixth threshold value (i.e., the third threshold value), the light source control unit 114 increases the light amount of infrared light emitted from the infrared light source 123 until the second slope in the infrared light wave becomes the first slope A stored in the memory.

In a case where a standard deviation of a plurality of first heartbeat time intervals is larger than the fourth threshold value, where a standard deviation of a plurality of second heartbeat time interval is larger than the fourth threshold value, and where a difference between a first heartbeat time interval and a second heartbeat time interval that correspond to each other in a time sequence is a value between the fifth threshold value and the sixth threshold value, the light source control unit 114 increases the light amount of visible light emitted from the visible light source 121 and decreases the light amount of infrared light emitted from the infrared light source 123.

In the above description, the light source control unit 114 increases the light amount of the infrared light source 123 until the second slope of the infrared light wave becomes the first slope A in cases other than a case where predetermined feature points have been obtained in neither the visible light wave nor the infrared light wave (e.g., "FALSE, BOTH"). However, the present embodiment is not limited to this. For example, in a case where an average luminance value in an ROI is larger than a seventh threshold value (e.g., 240), an image of a user's skin is buried in noise information due to a too large light amount of a light source. The average luminance "240" is "240" among values from 0 to 255 indicative of luminance, and a larger average luminance value indicates higher luminance. In this case, since it can be assumed that the second slope of the infrared light wave is larger than the first slope A, the light source control unit 114 may decrease the light amount of infrared light until the second slope becomes the first slope A.

Figure 20:
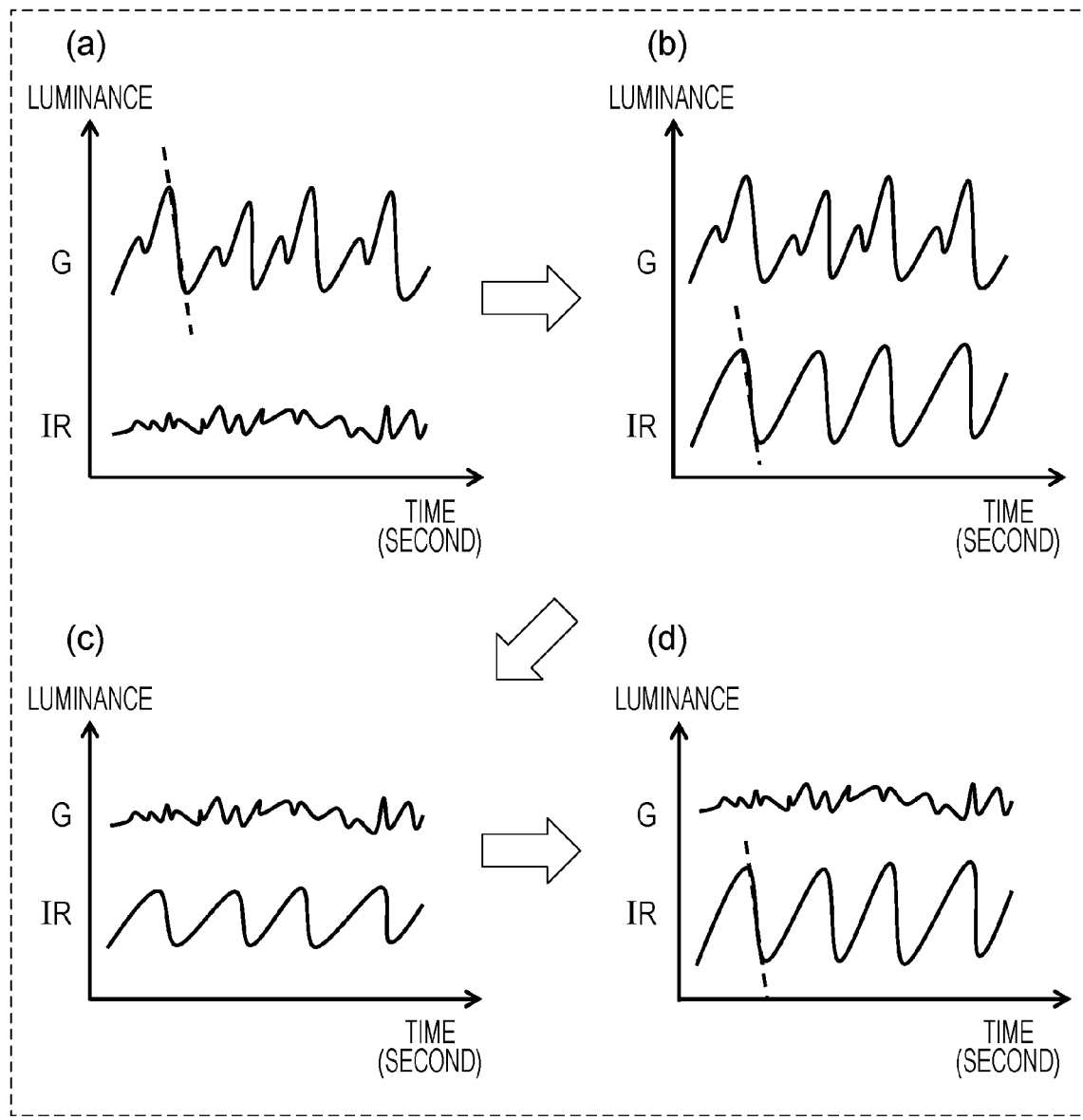
FIG. 20 is a diagram illustrating an example of simplest steps for decreasing the light amount of a visible light source to zero and increasing the light amount of an infrared light source to a proper light amount by using the pulse wave measuring device.

FIG. 20 is a diagram illustrating an example of the simplest steps for decreasing the light amount of the visible light source to zero and increasing the light amount of the infrared light source to a proper light amount by using the pulse wave measuring device. In all of the graphs illustrated in FIGS. 20(a) through 20(d), the horizontal axis represents a time, and the vertical axis represents luminance. In FIG. 20, a visible light wave is indicated by "RGB", and an infrared light wave is indicated by "IR".

FIG. 20(a) is a diagram illustrating a visible light wave and an infrared light wave that are obtained in an initial state where a user turns on the visible light source 121 in the pulse wave measuring device 10. The visible light wave illustrated in FIG. 20(a) is a wave in which a slope from a top point to a bottom point is largest among the visible light waves illustrated in FIGS. 20(a) through 20(d). Accordingly, the slope from a top point to a bottom point of the visible light wave in this state is stored as the first slope A in the memory.

In this state, the infrared light source 123 is off. Accordingly, almost no infrared light wave is obtained. In this state, the correlation value computing unit 113 transmits, for example, a "FALSE, IR" signal to the light source control unit 114. Accordingly, the light source control unit 114 increases the light amount of the infrared light source 123. As the light source control unit 114 increases the light amount of the infrared light source 123, the infrared light wave computing unit 112 becomes able to obtain predetermined feature points of an infrared light wave and therefore obtain second heartbeat time intervals. Furthermore, a standard deviation of the obtained second heartbeat time intervals becomes equal to or smaller than the fourth threshold value. Then, as illustrated in FIG. 20(b), the light source control unit 114 increases the light amount of the infrared light source 123 until the second slope between a top point and a bottom point of the infrared light wave becomes the first slope A while maintaining the state where the standard deviation of the second heartbeat time intervals is equal to or smaller than the fourth threshold value. In a case where the second slope becomes the first slope A, the correlation value computing unit 113 transmits, for example, a "TRUE, AMP=A" signal to the light source control unit 114. Upon receipt of the "TRUE, AMP=A" signal, the light source control unit 114 suspends adjustment of the light source.

Next, from the state illustrated in FIG. 20(b), the light source control unit 114 gradually decreases the light amount of a visible light source of the visible light source 121. FIG. 20(c) illustrates a state where the standard deviation of the heartbeat time intervals is equal to or smaller than the fourth threshold value in the infrared light wave computing unit 112 and the light source of the visible light source 121 is off. FIG. 20(d) illustrates a state where the light source of the visible light source 121 is off and the second slope of the infrared light wave is the first slope A, i.e., a state that is finally aimed at.

In the process from the state of FIG. 20(b) to the state of FIG. 20(c), the light amount of visible light is decreased by a certain amount (e.g., by 1W). Every time the light amount of visible light is decreased, the infrared light wave computing unit 112 and the correlation value computing unit 113 check whether or not predetermined feature points have been properly obtained in the infrared light wave. In a case where the infrared light wave computing unit 112 and the correlation value computing unit 113 confirm that predetermined feature points have been properly obtained in the infrared light wave, the light amount of the light source of the infrared light source 123 is increased until the second slope of the infrared light wave becomes the first slope A as illustrated in FIG. 20(d).

Accordingly, in the process from the state of FIG. 20(b) to the state of FIG. 20(c), the correlation value computing unit 113 transmits a "TRUE" signal or a "FALSE, IR" signal to the light source control unit 114, and the light source control unit 114 adjusts the light amount of the infrared light source 123 until the "FALSE, IR" signal becomes "TRUE" every time the "FALSE, IR" signal is received. Then, when the light source control unit 114 receives "FALSE, RGB" from the correlation value computing unit 113 by decreasing the light amount of the visible light source 121, the light source control unit 114 finishes this process.

In the process from the state of FIG. 20(c) to the state of FIG. 20(d), the correlation value computing unit 113 transmits a "FALSE, RGB" signal to the light source control unit 114, and the light source control unit 114 continues to increase the light amount of the light source of the infrared light source 123 until the second slope of the infrared light wave becomes the first slope A. The light source control unit 114 finishes control of the light amounts of the light sources, for example, upon receipt, from the correlation value computing unit 113, of a "FALSE, RGB, AMP=A" signal indicating that a visible light wave has not been obtained and that the second slope has become the first slope A.

The light source control unit 114 controls a light source after two or more successive predetermined feature points have been obtained from a visible light wave or an infrared light wave by the visible light wave computing unit 111 or the infrared light wave computing unit 112. That is, the light source control unit 114 suspends output of the first control signal or the third control signal until two or more successive first peak points are extracted within a second predetermined period from a first visible light wave or until two or more successive third peak points are extracted within the second predetermined period from a second visible light wave. Furthermore, the light source control unit 114 suspends output of the second control signal or the fourth control signal until two or more successive second peak points are extracted within the second predetermined period from a first infrared light wave or until two or more successive fourth peak points are extracted within the second predetermined period from a second infrared light wave.

Figure 21:
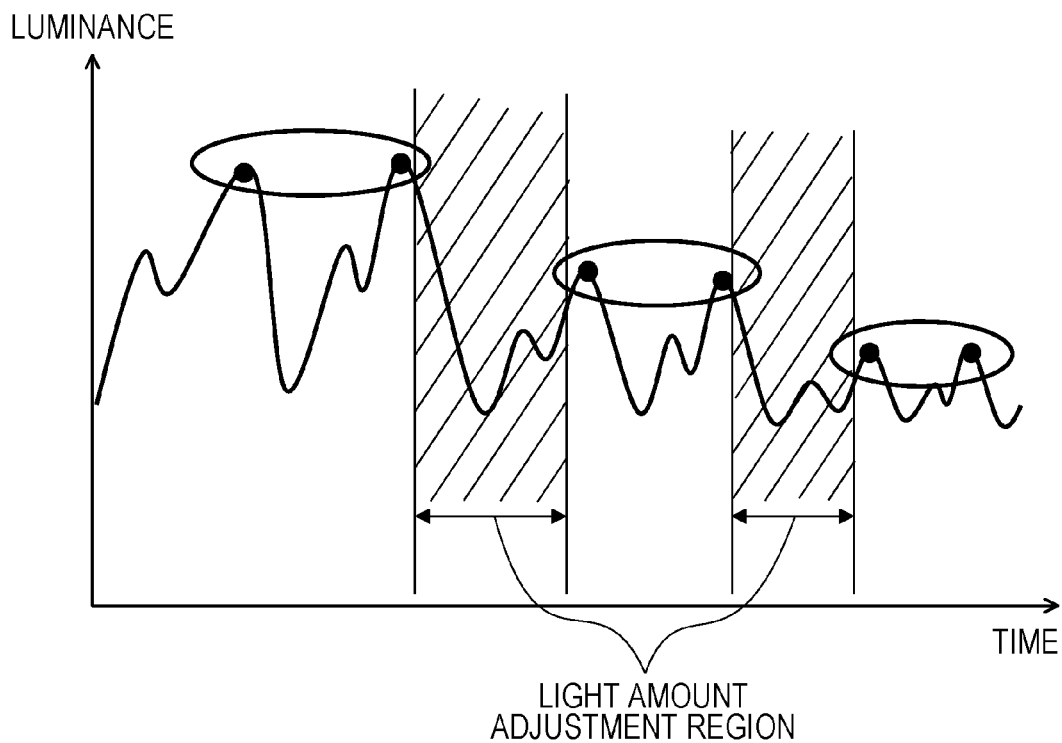
FIG. 21 is a diagram for explaining that control of a light source is suspended until two or more successive predetermined feature points are extracted within a second predetermined period from a visible light wave or an infrared light wave.

FIG. 21 is a diagram for explaining that control of a light source is suspended until two or more successive predetermined feature points are extracted within the second predetermined period from a visible light wave or an infrared light wave. The graph illustrated in FIG. 21 shows a visible light wave or an infrared light wave. In the graph illustrated in FIG. 21, the horizontal axis represents a time, and the vertical axis represents luminance.

When the light source control unit 114 changes the light amount of the visible light source 121 or the light amount of the infrared light source 123, a gain of luminance of the visible light wave or the infrared light wave changes. When the gain of luminance changes, the position of a pulse wave timing is deviated. This causes a large error in calculation of a timing such as a heartbeat time interval. In the present disclosure, a heartbeat time interval is mainly used to determine a correlation value between a visible light wave and an infrared light wave, and two successive peak points are needed for calculation of a heartbeat time interval. Therefore, the light source control unit 114 adjusts a light source amount after it is confirmed that two or more successive peak points have been obtained in a visible light wave or an infrared light wave, as illustrated in FIG. 21.

Biological Information Calculating Unit

The biological information calculating unit 115 calculates biological information of a user by using either features of a visible light wave obtained by the visible light wave computing unit 111 or features of an infrared light wave obtained by the infrared light wave computing unit 112. Specifically, the biological information calculating unit 115 obtains first heartbeat time intervals from the visible light wave computing unit 111 in a case where the visible light source 121 is on and where a visible light wave can be obtained by the visible light wave computing unit 111. Then, the biological information calculating unit 115 calculates biological information such as a heart rate or a stress index by using the first heartbeat time intervals.

Meanwhile, the biological information calculating unit 115 obtains second heartbeat time intervals from the infrared light wave computing unit 112 in a case where the visible light source 121 is off or in a case where a visible light wave cannot be obtained by the visible light wave computing unit 111 and where an infrared light wave can be obtained by the infrared light wave computing unit 112. Then, similarly, the biological information calculating unit 115 calculates biological information such as a heart rate or a stress index by using the second heartbeat time intervals.

The biological information calculating unit 115 calculates biological information by using the first heartbeat time intervals obtained from the visible light wave computing unit 111 in a case where features (heartbeat time intervals) of a wave (a visible light wave or an infrared light wave) have been extracted by both of the visible light wave computing unit 111 and the infrared light wave computing unit 112. This is because visible light has robustness to noise such as a body motion and therefore has high reliability as compared with infrared light.

The biological information calculating unit 115 may calculate biological information by using obtained features of a visible light wave or may calculate biological information by using obtained features of an infrared light wave. The biological information calculating unit 115 may calculate biological information of a user by using features of a second visible light wave obtained after output of the second control signal from the light source control unit 114 or may calculate biological information of a user by using features of a first visible light wave obtained before output of the second control signal from the light source control unit 114. Similarly, the biological information calculating unit 115 may calculate biological information of a user by using features of a second infrared light wave obtained after output of the first control signal from the light source control unit 114 or may calculate biological information of a user by using features of a first infrared light wave obtained before output of the first control signal from the light source control unit 114.

A heart rate and a stress index have been described above as examples of calculated biological information, but the biological information is not limited to these. For example, an arteriosclerotic index may be calculated by calculating an acceleration pulse wave from an obtained pulse wave. Alternatively, a blood pressure may be estimated by accurately obtaining a pulse wave timing from two different portions of a user and calculating a time difference (pulse wave propagation time) between the pulse wave timings thus obtained. Alternatively, a sleep stage may be calculated by calculating superiority of a sympathetic nerve or a parasympathetic nerve from a fluctuation in heartbeat time interval.

The biological information calculating unit 115 may output, as a stress index, information indicating, for example, "high stress" or "low stress" in accordance with an LF/HF value.

The biological information calculating unit 115 may calculate a sleep stage as described in Japanese Unexamined Patent Application Publication No. 2007-130182. Specifically, a sleep stage can be determined on the basis of LF, HF, and the presence or absence of a body motion. The sleep stage is an index indicative of a degree of activity of a subject's brain. For example, non-REM sleep or REM sleep may be determined as a sleep stage. In the case of non-REM sleep, shallow sleep or deep sleep may be further determined.

The biological information calculating unit 115 may give values to respective determined sleep stages and output such a value as a sleep stage.

The low frequency (LF) and high frequency (HF) are obtained by performing processing like the one described in Japanese Unexamined Patent Application Publication No. 2007-130182. That is, pulse interval data (a heartbeat time interval) is converted into a frequency spectrum distribution, for example, by fast Fourier transform (FFT). Next, the LF and HF are obtained from the obtained frequency spectrum distribution. Specifically, an arithmetic mean of sums of values of three points, i.e., a peak point and previous and next points spaced at regular intervals from the peak point in a plurality of power spectra is obtained as the LF and HF. Other examples of the FFT method used as a frequency analysis method include an AR model, a maximum entropy method, and a wavelet method.

Presenting Device

The presenting device 40 is a device that presents biological information received from the biological information calculating unit 115. Specifically, the presenting device 40 is a device that presents biological information such as a heart rate, a stress index, or a sleep stage obtained from the biological information calculating unit 115. The presenting device 40 is realized, for example, by the mobile terminal 30 and may display graphics indicative of biological information on the display 204 of the mobile terminal 30 or may output sound indicative of biological information from a speaker (not illustrated) of the mobile terminal 30.

In a case where the pulse wave measuring device 10 has a display, the presenting device 40 may be realized by this display. In a case where the pulse wave measuring device 10 has a speaker, the presenting device 40 may be realized by this speaker.

In the above description, the presenting device 40 presents biological information obtained from the biological information calculating unit 115. However, the present embodiment is not limited to this. For example, the presenting device 40 may always present the light amount of a light source of the visible light source 121 and the light amount of a light source of the infrared light source 123. Furthermore, the presenting device 40 may present a degree of matching at a current time obtained by the correlation value computing unit 113, for example, as reliability in percentage terms. Specifically, the presenting device 40 may present a correlation coefficient between a visible light wave and an infrared light wave.

Figure 22:
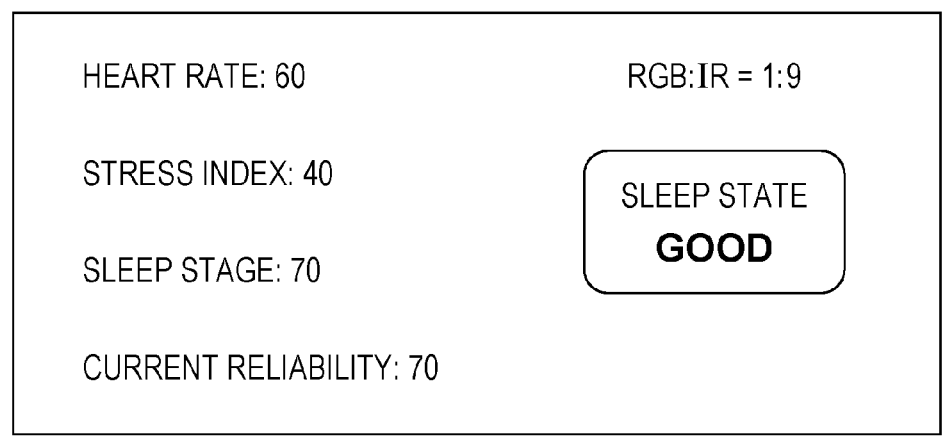
FIG. 22 is a diagram illustrating a display example on a presenting device.

FIG. 22 illustrates an example of display on the presenting device. As illustrated in FIG. 22, the presenting device 40 displays graphics indicating a heart rate, a stress index, a sleep stage, and current reliability (i.e., a correlation coefficient between heartbeat time intervals of a visible light wave and heartbeat time intervals of an infrared light wave). Furthermore, the presenting device 40 may display a ratio of a light amount of a visible light source and a light amount of an infrared light source at a current time. Furthermore, the presenting device 40 may determine a user's sleep state on the basis of these parameters by referring to a table in which values of a heart rate, a stress index, and a sleep stage are associated with sleep states in advance and display the determined sleep state. For example, in a case where the heart rate is 65 or less, the stress index is 40 or less, and the sleep stage is 70 or more, the presenting device 40 displays "GOOD". The presenting device 40 need not display aforementioned presented items such as biological information as soon as these items are calculated. That is, since a user is basically sleeping, presented items such as biological information obtained by calculation need not promptly presented and instead may be recorded (accumulated) and be presented when the user wakes up, for example, next morning. This allows the user to check if the user slept well.

1-3. Operation

Figure 23:
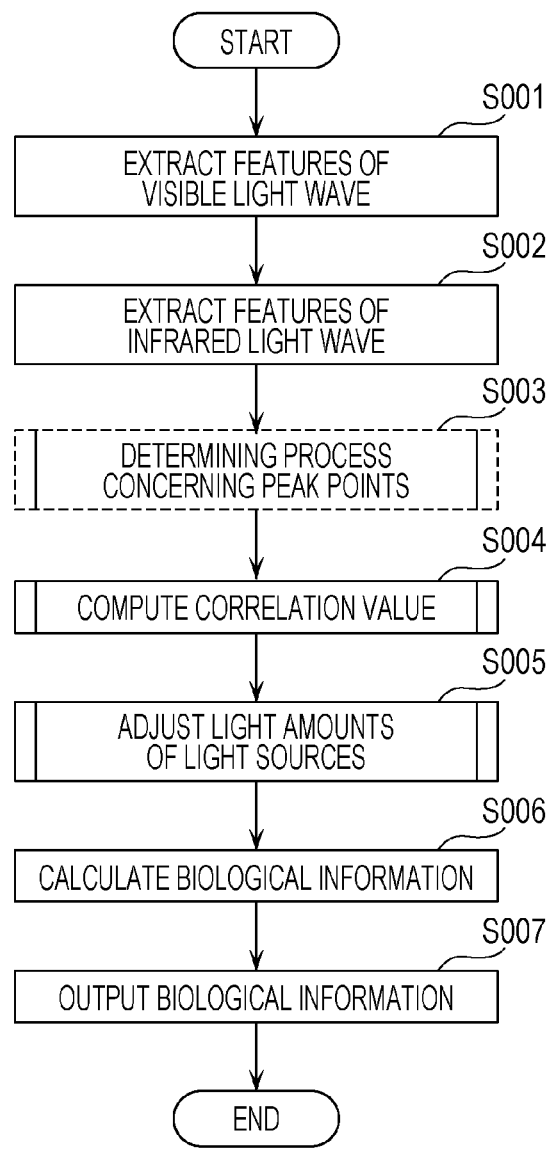
FIG. 23 is a flowchart illustrating a flow of processes of the pulse wave measuring device according to the present embodiment.

Next, operation of the pulse wave measuring device 10 according to the present embodiment is described. FIG. 23 is a flowchart illustrating a flow of processing of the pulse wave measuring device 10 according to the present embodiment.

First, the visible light source 121 is activated when a user enter a room or when the user controls the controller. The visible light wave computing unit 111 obtains visible light images, in a visible light wavelength range, of the user irradiated with visible light by the visible light source 121 and then extracts a visible light wave that is a wave indicative of a users pulse wave from the obtained visible light images. The visible light wave computing unit 111 extracts a plurality of first feature points that are predetermined feature points from the visible light wave. Then, the visible light wave computing unit 111 calculates first heartbeat time intervals as features of the visible light wave (S001). Furthermore, the visible light wave computing unit 111 causes a slope from a top point to a bottom point of the visible light wave at this point in time to be stored as a first slope A in the memory.

Next, the infrared light wave computing unit 112 obtains infrared light images, in an infrared light wavelength range, of the user irradiated with infrared light by the infrared light source 123 and then extracts an infrared light wave that is a wave indicative of a user's pulse wave from the obtained infrared light images. The infrared light wave computing unit 112 extracts a plurality of second feature points that are predetermined feature points from the infrared light wave. Then, the infrared light wave computing unit 112 calculates second heartbeat time intervals as features of the infrared light wave (S002).

Then, the correlation value computing unit 113 performs a determining process concerning peak points (S003). Specifically, the correlation value computing unit 113 determines, as for the first feature points extracted from the visible light wave, whether or not an excessive number of peak points have been obtained. Furthermore, the correlation value computing unit 113 determines, as for the second feature points extracted from the infrared light wave, whether or not an excessive number of peak points have been obtained. Details of the determining process concerning peak points performed by the correlation value computing unit 113 will be described later.

Next, the correlation value computing unit 113 computes a correlation value between the visible light wave and the infrared light wave (S004). Details of the correlation value computing process performed by the correlation value computing unit 113 will be described later.

Next, the light source control unit 114 adjusts light amounts of light sources (S005). The light source control unit 114 outputs control signals for controlling the light amounts of the light sources in accordance with a result of adjustment of the light amounts. Details of the light amount adjusting process performed by the light source control unit 114 will be described later.

Next, the biological information calculating unit 115 calculates biological information from at least one of the features of the visible light wave and the features of the infrared light wave (S006).

Next, the biological information calculating unit 115 supplies the calculated biological information to the presenting device 40 (S007).

Figure 24:
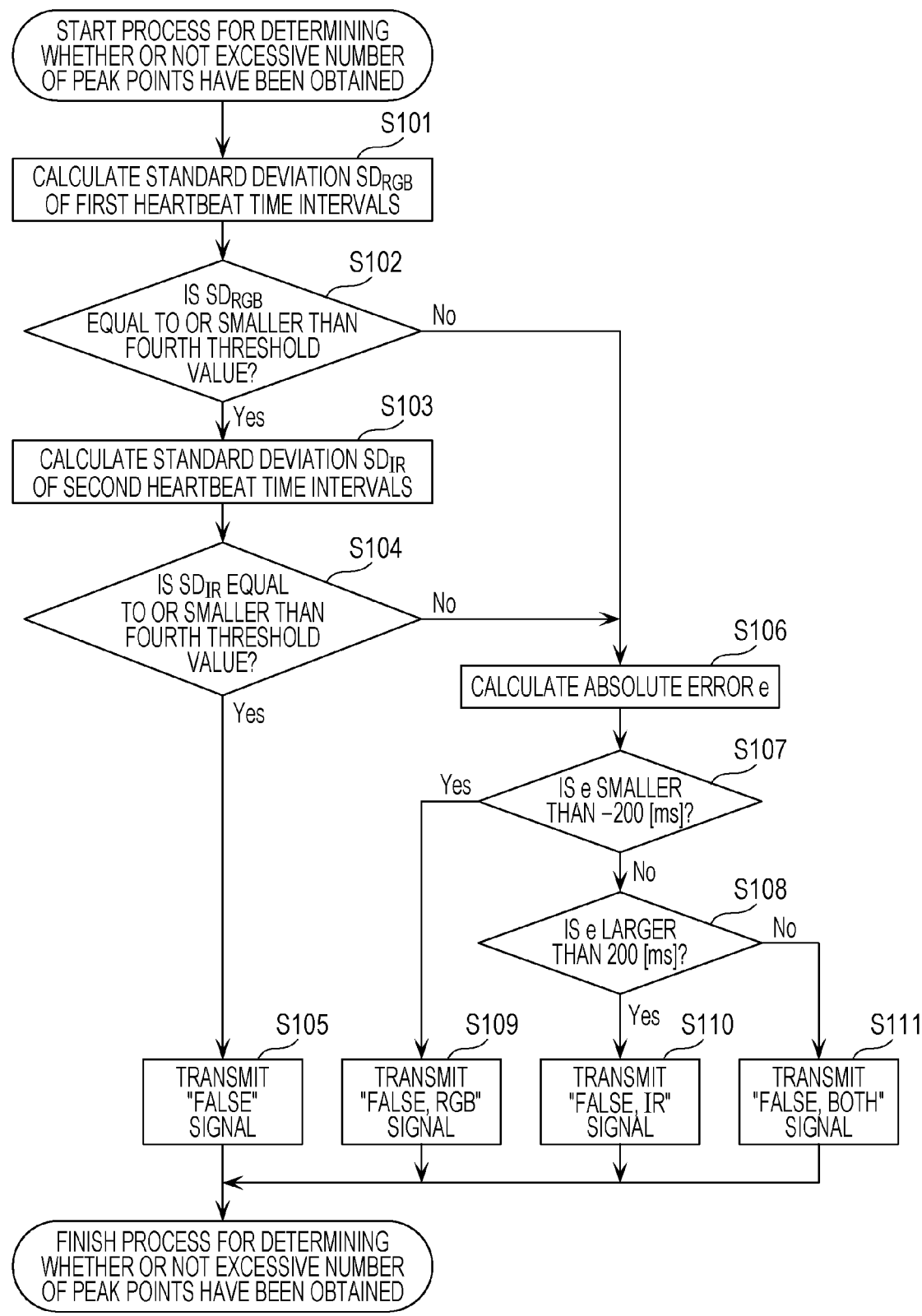
FIG. 24 is a flowchart illustrating details of a process for determining whether or not an excessive number of peak points have been obtained according to the present embodiment.

FIG. 24 is a flowchart illustrating details of the process for determining whether or not an excessive number of peak points have been obtained according to the present embodiment.

The correlation value computing unit 113 calculates a standard deviation $SD_{RGB}$ of the first heartbeat time intervals (S101).

Next, the correlation value computing unit 113 determines whether or not the standard deviation $SD_{RGB}$ is equal to or smaller than the fourth threshold value (S102).

In a case where it is determined that the standard deviation $SD_{RGB}$ is equal to or smaller than the fourth threshold value (YES in S102), the correlation value computing unit 113 calculates a standard deviation $SD_{IR}$ of the second heartbeat time intervals (S103).

Then, the correlation value computing unit 113 determines whether or not the standard deviation $SD_{IR}$ is equal to or smaller than the fourth threshold value (S104).

By thus performing at east one of Step S102 and Step S104, the correlation value computing unit 113 performs the second process for determining whether or not the calculated standard deviation $SD_{RGB}$ is larger than the fourth threshold value and the calculated standard deviation $SD_{IR}$ is larger than the fourth threshold value.

In a case where it is determined that the standard deviation $SD_{IR}$ is equal to or smaller than the fourth threshold value (Yes in S104), the correlation value computing unit 113 transmits a "FALSE" signal to the light source control unit 114 (S105).

Meanwhile, in a case where it is determined that the standard deviation $SD_{RGB}$ is larger than the fourth threshold value (No in S102) or in a case where it is determined that the standard deviation $SD_{IR}$ is larger than the fourth threshold value (No in S104), the correlation value computing unit 113 calculates an absolute error e between a first heartbeat time interval and a second heartbeat time interval that correspond to each other (S106).

The correlation value computing unit 113 determines whether or not the absolute error e is smaller than −200 [ms] (S107).

In a case where it is determined that the absolute error e is smaller than −200 [ms] (Yes in S107), the correlation value computing unit 113 supplies a "FALSE, RGB" signal to the light source control unit 114 (S109).

Meanwhile, in a case where it is determined that the absolute error e is equal to or larger than −200 [ms] (No in S107), the correlation value computing unit 113 determines whether or not the absolute error e is larger than 200 [ms] (S108).

That is, in a case where it is determined as a result of the second determining process that the standard deviation $SD_{RGB}$ is larger than the fourth threshold value and that the standard deviation $SD_{IR}$ is larger than the fourth threshold value, the correlation value computing unit 113 performs the third determining process for determining whether or not an absolute error e (time difference) between a first heartbeat time interval and a second heartbeat time interval that correspond to each other in a time sequence is smaller than the fifth threshold value and the fourth determining process for determining whether or not the time difference is larger than the sixth threshold value that is larger than the fifth threshold value.

In a case where it is determined that the absolute error e is larger than 200 [ms] (Yes in S108), the correlation value computing unit 113 transmits a "FALSE, IR" signal to the light source control unit 114 (S110).

In a case where it is determined that the absolute error e is equal to or smaller than 200 [ms] (No in S108), the correlation value computing unit 113 transmits a "FALSE, BOTH" signal to the light source control unit 114 (S111).

Figure 25:
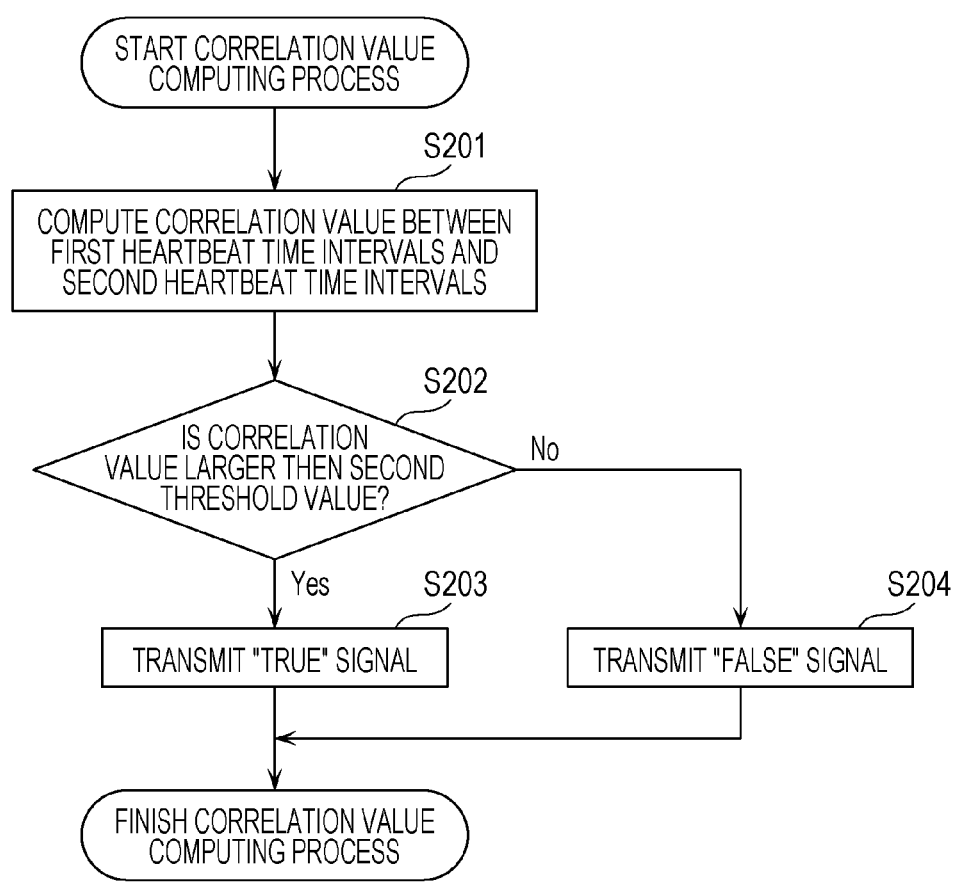
FIG. 25 is a flowchart illustrating details of a correlation value computing process according to the present embodiment.

FIG. 25 is a flowchart illustrating details of the correlation value computing process according to the present embodiment.

First, the correlation value computing unit 113 computes a correlation value between a plurality of first heartbeat time intervals and a plurality of second heartbeat time intervals (S201).

The correlation value computing unit 113 determines whether or not the correlation value thus computed is larger than the second threshold value (S202). That is, the correlation value computing unit 113 performs the first determining process for determining whether or not the computed correlation value is equal to or larger than the second threshold value, In a case where it is determined that the correlation value is larger than the second threshold value (Yes in S202), the correlation value computing unit 113 transmits a "TRUE" signal to the light source control unit 114 (S203).

Meanwhile, in a case where it is determined that the correlation value is equal to or smaller than the second threshold value (No in S202), the correlation value computing unit 113 transmits a "FALSE" signal to the light source control unit 114 (S204).

Figure 26:
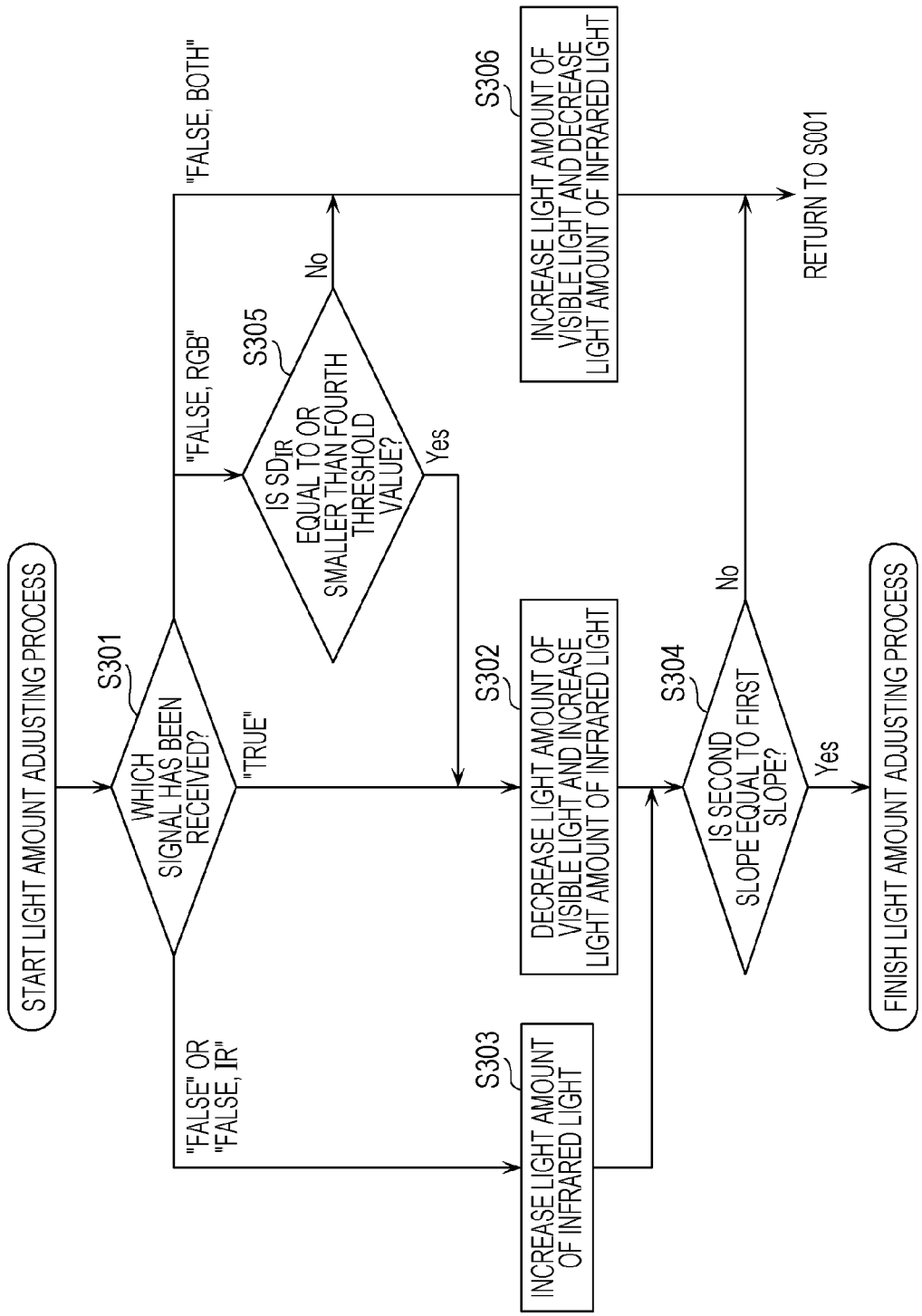
FIG. 26 is a flowchart illustrating details of a light amount adjusting process according to the present embodiment.

FIG. 26 is a flowchart illustrating details of the light amount adjusting process according to the present embodiment.

The light source control unit 114 determines which of the "TRUE", "FALSE", "FALSE, IR", "FALSE, RGB", and "FALSE, BOTH" has been received from the correlation value computing unit 113 (S301).

In a case where the "TRUE" signal has been received, the light source control unit 114 decreases a light amount of visible light and increases a light amount of infrared light (S302).

In a case where the "FALSE" signal or the "FALSE, IR" signal is received, the light source control unit 114 increases the light amount of infrared light (S303). That is, in a case where the correlation value computing unit 113 determines that the absolute error e is larger than the sixth threshold value, the light source control unit 114 receives the "FALSE, IR" signal and therefore supplies, as the second control signal, a control signal for increasing the light amount of infrared light emitted from the infrared light source 123 to the infrared light source 123.

In a case where the light amount of infrared light is increased in Step S302 or Step S303, the light source control unit 114 determines whether or not the second slope of the infrared light wave is equal to the first slope A stored in the memory (S304).

In a case where it is determined that the second slope of the infrared light wave is equal to the first slope A (Yes in S304), the light source control unit 114 finishes the light amount adjusting process.

In a case where the "FALSE, RGB" is received, the light source control unit 114 determines whether or not the standard deviation $SD_{IR}$ is equal to or smaller than the fourth threshold value (S305). That is, in a case where the correlation value computing unit 113 determines that the absolute error e is smaller than the fifth threshold value, the light source control unit 114 performs the fifth determining process for determining whether or not the standard deviation $SD_{IR}$ is equal to or smaller than the fourth threshold value.

In a case where it is determined that the standard deviation $SD_{IR}$ is equal to or smaller than the fourth threshold value (Yes in S305), the light source control unit 114 performs the process in Step S302. That is, in a case where the correlation value computing unit 113 determines that the standard deviation $SD_{IR}$ is equal to or smaller than the fourth threshold value, the light source control unit 114 supplies the first control signal for decreasing the light amount of visible light emitted from the visible light source 121 to the visible light source 121 and supplies the second control signal for increasing the light amount infrared light emitted from the infrared light source 123 to the infrared light source 123.

In a case where the "FALSE, BOTH" signal is received or in a case where it is determined that the standard deviation $SD_{IR}$ is larger than the fourth threshold value (No in S305), the light source control unit 114 increases the light amount of visible light back to an initial light amount and decreases the light amount of infrared light and turns off the infrared light source 123 (S306). That is, in a case where the correlation value computing unit 113 determines that the absolute error e is not less than the fifth threshold value and not more than the sixth threshold value, the light source control unit 114 receives the "FALSE, BOTH" signal, and therefore supplies, as the first control signal, a control signal for increasing the light amount of visible light emitted from the visible light source 121 to the visible light source 121 and supplies, as the second control signal, a control signal for decreasing the light amount of infrared light emitted from the infrared light source 123 to the infrared light source 123. Alternatively, in a case where the correlation value computing unit 113 determines that the standard deviation $SD_{IR}$ is larger than the fourth threshold value, the light source control unit 114 supplies, as the first control signal, a control signal for increasing the light amount of visible light emitted from the visible light source 121 and supplies, as the second control signal, a control signal for decreasing the light amount of infrared light emitted from the infrared light source 123 to the infrared light source 123.

In a case where it is determined in Step S304 that the second slope is different from the first slope A (No in S304) or in a case where Step S306 is finished, the light source control unit 114 returns to Step S001. That is, in a case where the condition in Step S304 is not met even after change of the light amount of visible light emitted from the visible light source 121 and the light amount of infrared light emitted from the infrared light source 123, the pulse wave measuring device 10 returns to Step S001, and repeats the process for obtaining visible light images, the process for obtaining infrared light images, the process for extracting a visible light wave, the process for extracting an infrared light wave, and the process for computing a correlation value and outputs a first control signal and a second control signal in accordance with a result of the repeated computation of the correlation value. That is, the process for obtaining visible light images, the process for obtaining infrared light images, the process for extracting a visible light wave, the process for extracting an infrared light wave, the process for computing a correlation value, the process for outputting the first control signal, and the process for outputting the second control signal are repeatedly performed until the condition in Step S304 is met. Visible light images obtained in the second or later process are referred to as second visible light images, infrared light images obtained in the second or later process are referred to as second infrared light images, a visible light wave extracted in the second or later process is referred to as a second visible light wave, and an infrared light wave extracted in the second or later process is referred to as a second infrared light wave.

For example, the first visible light images are visible light images taken by the visible light imaging unit 122 before output of the first control signal or the third control signal, and the second visible light images are visible light images taken by the visible light imaging unit 122 after output of the first control signal or the third control signal. The first infrared light images are infrared light images taken by the infrared light imaging unit 124 before output of the second control signal or the fourth control signal, and the second infrared light images are infrared light images taken by the infrared light imaging unit 124 after output of the second control signal or the fourth control signal.

1-4. Effects and Other Remarks

According to the pulse wave measuring device 10 according to the present embodiment, a correlation value between a visible light wave obtained from visible light images capturing a user's pulse wave and an infrared light wave obtained from infrared light images capturing the same pulse wave is computed, and the light amount of infrared light emitted from an infrared light source is controlled in accordance with the correlation value. This makes it possible to properly adjust the light amount of infrared light, thereby making it possible to obtain biological information of the user even in a dark state (e.g., during sleep). It is therefore possible to achieve, for example, non-contact biological monitoring during sleep without the need for a biological sensor used in contact with a human.

Furthermore, according to the pulse wave measuring device 10, the correlation value computing unit 113 computes a correlation value by comparing first heartbeat time intervals calculated from a visible light wave and second heartbeat time intervals calculated from an infrared light wave. It is therefore possible to easily compute a correlation value between the visible light wave and the infrared light wave.

Furthermore, according to the pulse wave measuring device 10, since the second slope in the infrared light wave after adjustment of the light amount of the infrared light source and the first slope A stored in the memory are compared, it is possible to determine whether or not the light amount of the infrared light source has become a proper light amount.

Furthermore, according to the pulse wave measuring device 10, in a case where an absolute error e between a first heartbeat time interval and a second heartbeat time interval is larger than the third threshold value, a predetermined feature point used for computation of one of the first and second heartbeat time intervals in a wave having a larger number of predetermined feature points is excluded from computation of the one of the first and second heartbeat time intervals. This makes it possible to delete an excessive peak point, thereby making it possible to obtain a proper first heartbeat time interval or second heartbeat time interval.

Furthermore, the pulse wave measuring device 10 decides to increase, decrease, or maintain the light amount of the visible light source and the light amount of the infrared light source in accordance with the computed correlation value and a result of extraction of predetermined feature points from the visible light wave and the infrared light wave and supplies a control signal corresponding to a result of the decision to the visible light source and the infrared light source. This makes it possible to properly adjust the light amount of the visible light source and the light amount of the infrared light source.

Furthermore, according to the pulse wave measuring device 10, predetermined feature points are not extracted from a visible light wave or an infrared light wave obtained during control of the light amount of the visible light source 121 or the light amount of the infrared light source 123 based on the control signal. It is therefore possible to properly extract predetermined feature points, thereby making it possible to precisely calculate biological information.

Furthermore, according to the pulse wave measuring device 10, output of a control signal for controlling the light amount of visible light emitted from the visible light source 121 or output of a control signal for controlling the light amount of infrared light emitted from the infrared light source is suspended until two or more successive predetermined feature points are extracted within the second predetermined period from a visible light wave or an infrared light wave. This makes it possible to properly extract predetermined feature points, thereby making it possible to precisely calculate biological information.

1-5. Modifications

In a case where the visible light source 121 is activated from a light amount 0, the light amount may be controlled to a preset initial value although this is not mentioned in particular in the above embodiment. This makes it possible to promptly obtain user's favorite illuminance or illuminance at which a pulse wave is easily obtained in a case where such illuminance is set by the user.

A light amount of the visible light source 121 at a time when a visible light wave can be obtained and a slope between a top point and a bottom point of the visible light wave is largest may be recorded by the visible light wave computing unit 111, and the light amount of the visible light source 121 may be controlled to the recorded value every time a user enters a room.

Figure 27:
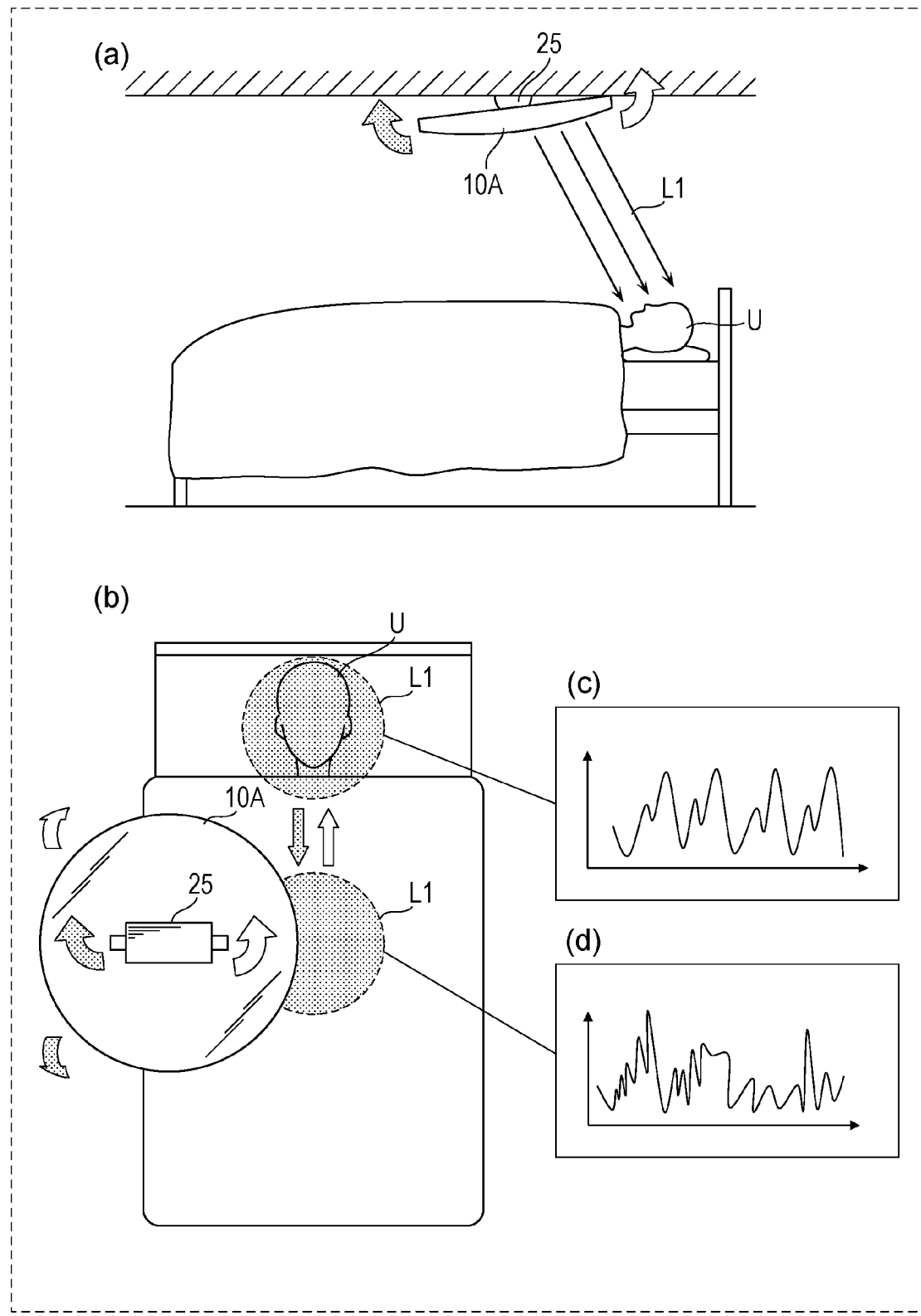
FIG. 27 is a diagram for explaining characteristics of a pulse wave measuring device according to a modification.

In the above embodiment, the visible light source 121 is fixed and is, for example, realized by a fluorescent lamp or a white LED. However, the present disclosure is not limited to this. For example, the visible light source 121 may be configured to have a driving unit so that not only a light amount, but also a direction of irradiation and a direction of imaging can be changed. FIG. 27 illustrates this example.

FIG. 27 is a diagram for explaining characteristics of a pulse wave measuring device 10A according to a modification. FIG. 27(*a*) is a diagram illustrating the pulse wave measuring device 10A and a user U viewed from a side. FIG. 27(*b*) is a diagram illustrating the pulse wave measuring device 10A and the user U viewed from a ceiling side. FIG. 27(*c*) is a diagram illustrating a visible light wave or an infrared light wave obtained in a case where a face of the user U is irradiated with light emitted from a light source of the pulse wave measuring device 10A. FIG. 27(*d*) is a diagram illustrating a visible light wave or an infrared light wave obtained in a case where a surface of a covering for a bed (a portion excluding skin of the user U) is irradiated with light emitted from a light source of the pulse wave measuring device 10A.

As illustrated in FIGS. 27(*a*) and 27(*b*), the pulse wave measuring device 10A can change a direction of irradiation of visible light or infrared light by driving the driving unit 25 with respect to a direction along the ceiling. This makes it possible to precisely obtain features of a visible light wave and an infrared light wave, for example, by driving the driving unit 25 so that a light irradiation range and an imaging range are changed from a state where a body portion (i.e., the surface of the covering for the bed) is irradiated to a state where the face of the user U is irradiated, as illustrated in FIG. 27(*b*). As a method for specifying the light irradiation portion and the imaging portion, the position of the face of the user U may be specified, for example, by face recognition using a taken image, and the angle of the pulse wave measuring device 10A may be adjusted by driving the driving unit 25 so that a portion (e.g., cheek) of the specified face is irradiated.

The driving unit 25 is mounted on an upper side of the pulse wave measuring device 10A as illustrated in FIGS. 27(*a*) and 27(*b*) and includes a motor.

When the user sends a control signal for controlling the motor to the pulse wave measuring device 10 by using a controller such as the mobile terminal 30, the angle of the pulse wave measuring device 10 can be changed, for example, in a body height direction of the user. This makes it possible to cope with large longitudinal displacement of the irradiation position. The pulse wave measuring device 10 may image the face by controlling the motor in accordance with a result of face recognition.

In the example of FIG. 27, the angle is controlled in the body height direction of the user (a top-bottom direction of the user in a state where the user is lying). However, the present modification is not limited to this. For example, the angle may be controlled in a body width direction of the user (a left-right direction of the user in a state where the user is lying). This makes it possible to make fine adjustment in a wider range. For example, it is possible to specify a user's face and obtain a pulse wave even in a case where lying direction and position vary from one user to another.

In this case, a pulse wave is not sometimes obtained depending on an irradiation direction of the visible light source 121. Accordingly, in a case where the light amount of visible light in the light source control unit 114 is larger than a predetermined threshold value and where features of a pulse wave have not been obtained in the visible light wave computing unit 111, a light irradiation direction may be changed so that a face is irradiated by specifying the user's face by using a face recognition program on an image obtained by the visible light imaging unit 122. In a case where the whole face is irradiated with light, strong light enters the user's eyes. In view of this, the light may be narrowed to a region around a cheek by recognizing the eyes, for example, in a case where the visible light source 121 is a light source (e.g., laser light) that can irradiate only a narrow region with light.

Continuous irradiation of human eyes with infrared light has a risk of a deterioration of eyesight although this is not mentioned in particular in the above embodiment. In view of this, the infrared light source 123 may irradiate only an ROI set in a region of a user's face other than human eyes with infrared light. In a case where the infrared light source 123 irradiates, for example, a users face with light, a pulse wave is easy to obtain especially in a cheek. Accordingly, the light source control unit 114 may specify, for example, a portion below a user's eye and may cause the infrared light source 123 to irradiate this portion with infrared light. The light source control unit 114 specifies the portion below the user's eye, for example, by using a result of face recognition performed by analyzing an image taken by the infrared light imaging unit 124. The light source control unit 114 may adjust the light amount of the infrared light source 123 so that the light amount of infrared light becomes smaller than a predetermined light amount in a case where the power of infrared light emitted from the infrared light source 123 is equal to or larger than a predetermined threshold value and where a predetermined period has elapsed. Furthermore, since infrared light affects user's eyesight as described above, an irradiation region may be narrowed so that a user's cheek is irradiated with infrared light by specifying a cheek region through face recognition of the user's face.

In the above embodiment, the pulse wave computing device 100 of the pulse wave measuring device 10 is provided in the pulse wave measuring device 10. However, the present disclosure is not limited to this. For example, the pulse wave computing device 100 may be realized by an external server device, may be realized by the mobile terminal 30, or may be realized by an information terminal such as a PC. That is, in this case, the pulse wave computing device 100 may be realized by any device as long as the pulse wave computing device 100 is capable of obtaining images taken by the visible light imaging unit 122 and the infrared light imaging unit 124 and controlling the light amount of the visible light source 121 and the light amount of the infrared light source 123.

The constituent elements included in the pulse wave measuring device and other devices may be circuits. These circuits may constitute a single circuit as a whole or may be different circuits. Furthermore, these circuits may be general-purpose circuits or may be dedicated-purpose circuits. That is, in the above embodiment, each of the constituent elements may be realized by dedicated hardware or may be realized by execution of a software program suitable for the constituent element.

Furthermore, each of the constituent elements may be realized by causing a program executing unit such as a CPU or a processor to read out and execute a software program recorded on a recording medium such as a hard disc or a semiconductor memory. Software for realizing the display control method and the like according to the above embodiment is the following program.

That is, this program is a pulse wave measuring method executed by a pulse wave measuring device including a processor and a memory, the pulse wave measuring method including: obtaining visible light images, in a visible light wavelength range, of a user irradiated with visible light by a visible light source; obtaining infrared light images, in an infrared light wavelength range, of the user irradiated with infrared light by an infrared light source; extracting a visible light wave that is a wave indicative of a pulse wave of the user from the obtained visible light images; extracting an infrared light wave that is a wave indicative of the pulse wave of the user from the obtained infrared light images; computing a correlation value between the extracted visible light wave and the extracted infrared light wave; supplying a control signal for controlling a light amount of infrared light emitted from the infrared light source to the infrared light source in accordance with the computed correlation value; calculating biological information from at least one of features of the visible light wave and features of the infrared light wave; and outputting the calculated biological information.

A pulse wave measuring device and the like according to one or more aspects have been described on the basis of the embodiment, but the present disclosure is not limited to this embodiment. Various modifications of the present embodiment which a person skilled in the art can think of and combinations of constituent elements in different embodiments may also be encompassed within the scope of the one or more aspects without departing from the scope of the present disclosure.

For example, in the above embodiment, a process performed by a specific constituent element may be performed by another constituent element instead of this specific constituent element. Furthermore, processes may be performed in a different order or may be performed in parallel.

The present disclosure is useful as a pulse wave measuring device that can precisely calculate biological information.

What is claimed is:

1. A pulse wave measuring device comprising:
   a processor; and
   a memory,
   wherein the processor directs processes to be performed including:
   acquiring a first visible light image, in a visible light wavelength range, of a user irradiated with visible light by a visible light source,
   acquiring a first infrared light image, in an infrared light wavelength range, of the user irradiated with infrared light by an infrared light source,
   extracting a first visible light wave that is a wave indicative of a pulse wave of the user from the acquired first visible light image,
   extracting a first infrared light wave that is a wave indicative of a pulse wave of the user from the acquired first infrared light image,
   computing a first correlation value between the extracted first visible light wave and the extracted first infrared light wave,
   performing a first determining process for determining whether or not the computed first correlation value is equal to or larger than a second threshold value,
   supplying a first control signal for decreasing a light amount of the visible light emitted from the visible light source to the visible light source and supplying a second control signal for increasing a light amount of the infrared light emitted from the infrared light source to the infrared light source in a case where the processor determines, as a result of the first determining process, that the computed first correlation value is equal to or larger than the second threshold value,
   acquiring a second visible light image, in the visible light wavelength range, of the user irradiated with visible light based on the first control signal by the visible light source,
   acquiring a second infrared light image, in the infrared light wavelength range, of the user irradiated with infrared light based on the second control signal by the infrared light source,
   extracting a second visible light wave that is a wave indicative of a pulse wave of the user from the acquired second visible light image,
   extracting a second infrared light wave that is a wave indicative of a pulse wave of the user from the acquired second infrared light image,
   calculating heart rate information by using at least one of the extracted second visible light wave and second infrared light wave, and
   outputting the calculated heart rate information.

2. The pulse wave measuring device according to claim 1, wherein in the computing the first correlation value, the processor directs processes to be performed including:
   extracting a plurality of first peak points from the first visible light wave by dividing the first visible light wave into a plurality of first unit waves on a basis of a pulse wave cycle that is a cycle of the pulse wave and then extracting, for each of the plurality of first unit waves, a first peak point that is a first top point indicative of a maximum value of the first unit wave or a first bottom point indicative of a minimum value of the first unit wave,
   extracting a plurality of second peak points from the first infrared light wave by dividing the first infrared light wave into a plurality of second unit waves on a basis of the pulse wave cycle and then extracting, for each of the plurality of second unit waves, a second peak point that is a second top point indicative of a maximum value of the second unit wave or a second bottom point indicative of a minimum value of the second unit wave,
   calculating a plurality of first heartbeat time intervals by calculating, for each of the plurality of extracted first peak points, a first heartbeat time interval that is a time interval between a first time point of the first peak point and a second time point of another first peak point that is adjacent, in a time sequence, to the first peak point,
   calculating a plurality of second heartbeat time intervals by calculating, for each of the plurality of extracted second peak points, a second heartbeat time interval that is a time interval between a third time point of the second peak point and a fourth time point of another second peak point that is adjacent, in a time sequence, to the second peak point, and
   computing, as the first correlation value, a first correlation coefficient between the plurality of first heartbeat time intervals and the plurality of second heartbeat time intervals that correspond to each other in a time sequence by using an equation 1:

$$\rho 1 = \frac{\sigma_{12}}{\sigma_1 \sigma_2}$$

where ρ1 is the first correlation value, $\sigma_{12}$ is a covariance of the plurality of first heartbeat time intervals and the plurality of second heartbeat time intervals, $\sigma_1$ is a first standard deviation that is a standard deviation of the plurality of first heartbeat time intervals, and $\sigma_2$ is a second standard deviation that is a standard deviation of the plurality of second heartbeat time intervals.

3. The pulse wave measuring device according to claim 2, wherein
the processor further directs processes to be performed including:
performing a second determining process for determining whether or not the first standard deviation is larger than a fourth threshold value and the second standard deviation is larger than the fourth threshold value,
performing a third determining process and a fourth determining process in a case where the processor determines, as a result of the second determining process, that the first standard deviation is larger than the fourth threshold value and the second standard deviation is larger than the fourth threshold value, the third determining process being a process for determining whether or not a first time difference between one of the plurality of first heartbeat time intervals and one of the plurality of second heartbeat time intervals that corresponds to the one first heartbeat time interval in a time sequence is smaller than a fifth threshold value, and the fourth determining process being a process for determining whether or not the first time difference is larger than a sixth threshold value that is larger than the fifth threshold value,
supplying the second control signal to the infrared light source in a case where the processor determines, as a result of the third determining process and the fourth determining process, that the first time difference is larger than the sixth threshold value, and
supplying a third control signal for increasing the light amount of the visible light emitted from the visible light source to the visible light source and supplying a fourth control signal for decreasing the light amount of the infrared light emitted from the infrared light source to the infrared light source in a case where the processor determines, as a result of the third determining process and the fourth determining process, that the first time difference is not less than the fifth threshold value and not more than the sixth threshold value.

4. The pulse wave measuring device according to claim 3, wherein
the processor further directs processes to be performed including:
performing a fifth determining process for determining whether or not the second standard deviation is equal to or smaller than the fourth threshold value in a case where the processor determines, as a result of the third determining process and the fourth determining process, that the first time difference is smaller than the fifth threshold value,
supplying the first control signal to the visible light source and supplying the second control signal to the infrared light source in a case where the processor determines, as a result of the fifth determining process, that the second standard deviation is equal to or smaller than the fourth threshold value, and
supplying the third control signal to the visible light source and supplying the fourth control signal to the infrared light source in a case where the processor determines, as a result of the fifth determining process, that the second standard deviation is larger than the fourth threshold value.

5. The pulse wave measuring device according to claim 4, wherein
the processor further directs processes to be performed including:
storing, as a first slope in the memory, a slope of a first straight line connecting one of the plurality of first top points and one of the plurality of first bottom points that immediately follows, in a time sequence, the one first top point,
extracting a plurality of third peak points from the second visible light wave by dividing the second visible light wave into a plurality of third unit waves on a basis of the pulse wave cycle and then extracting, for each of the plurality of third unit waves, a third peak point that is a third top point indicative of a maximum value of the third unit wave and a third bottom point indicative of a minimum value of the third unit wave,
extracting a plurality of fourth peak points from the second infrared light wave by dividing the second infrared light wave into a plurality of fourth unit waves on a basis of the pulse wave cycle and then extracting, for each of the plurality of fourth unit waves, a fourth peak point that is a fourth top point indicative of a maximum value of the fourth unit wave or a fourth bottom point indicative of a minimum value of the fourth unit wave,
calculating a plurality of third heartbeat time intervals by calculating, for each of the plurality of extracted third peak points, a third heartbeat time interval that is a time interval between a fifth time point of the third peak point and a sixth time point of another third peak point that is adjacent, in a time sequence, to the third peak point, calculating a plurality of fourth heartbeat time intervals by calculating, for each of the plurality of extracted fourth peak points, a fourth heartbeat time interval that is a time interval between a seventh time point of the fourth peak point and an eighth time point of another fourth peak point that is adjacent, in a time sequence, to the fourth peak point;
computing a second correlation coefficient between the plurality of third heartbeat time intervals and the plurality of fourth heartbeat time intervals that correspond to each other in a time sequence by using an equation 2:

$$\rho 2 = \frac{\sigma_{34}}{\sigma_3 \sigma_4}$$

where ρ2 is the second correlation coefficient, $\sigma_{34}$ is a covariance of the plurality of third heartbeat time intervals and the plurality of fourth heartbeat time intervals, $\sigma_3$ is a third standard deviation that is a standard deviation of the plurality of third heartbeat time intervals, and $\sigma_4$ is a fourth standard deviation that is a standard deviation of the plurality of fourth heartbeat time intervals,
repeatedly acquiring the second visible light image, repeatedly extracting the second visible light wave, repeatedly acquiring the second infrared light image, repeatedly extracting the second infrared light wave, and repeatedly computing the second correlation coefficient, in the repeated computing the second correlation coefficient, comparing, with the first slope stored in the memory, a second slope that is a slope of a second straight line connecting one of the plurality of fourth top points and one of the plurality of fourth bottom points that immediately follows, in a time sequence, the one fourth top point in the second infrared light wave thus repeatedly acquired, and supplying the second control signal to the infrared light source until the second slope becomes the first slope.

6. The pulse wave measuring device according to claim 5, wherein the processor further directs processing to be performed including:

performing a sixth determining process for determining whether or not the third standard deviation is larger than the fourth threshold value and the fourth standard deviation is larger than the fourth threshold value, performing a seventh determining process and an eighth determining process in a case where the processor determines, as a result of the sixth determining process, that the third standard deviation is larger than the fourth threshold value and the fourth standard deviation is larger than the fourth threshold value, the seventh determining process being a process for determining whether or not a second time difference between one of the plurality of third heartbeat time intervals and one of the plurality of fourth heartbeat time intervals that corresponds, in a time sequence, to the one third heartbeat time interval is smaller than the fifth threshold value, and the eighth determining process being a process for determining whether or not the second time difference is larger than the sixth threshold value, supplying the second control signal to the infrared light source in a case where the processor determines, as a result of the seventh determining process and the eighth determining process, that the second time difference is larger than the sixth threshold value, and supplying the third control signal to the visible light source and supplying the fourth control signal to the infrared light source in a case where the processor determines, as a result of the seventh determining process and the eighth determining process, that the second time difference is not less than the fifth threshold value and not more than the sixth threshold value.

7. The pulse wave measuring device according to claim 6, wherein the processor further directs processes to be performed including:

performing a ninth determining process for determining whether or not the fourth standard deviation is equal to or smaller than the fourth threshold value in a case where the processor determines, as a result of the seventh determining process and the eighth determining process, that the second time difference is smaller than the fifth threshold value;

supplying the first control signal to the visible light source and supplying the second control signal to the infrared light source in a case where the processor determines, as a result of the ninth determining process, that the fourth standard deviation is equal to or smaller than the fourth threshold value, and supplying the third control signal to the visible light source and supplying the fourth control signal to the infrared light source in a case where the processor determines, as a result of the ninth determining process, that the fourth standard deviation is larger than the fourth threshold value.

8. The pulse wave measuring device according to claim 5, wherein in the repeated computing the second correlation coefficient, the processor directs to be performed a tenth determining process for determining whether or not the number of third peak points or the number of fourth peak points within a first predetermined period is larger than a first threshold value;

in a case where the processor determines, as a result of the tenth determining process, that the number of third peak points or the number of fourth peak points within the first predetermined period is larger than the first threshold value, the processor directs to be performed processes including:

extracting a plurality of first inflection points by extracting, for each of the plurality of third top points, a first inflection point that is an inflection point between the third top point and a third bottom point that immediately follows, in a time sequence, the third top point among the plurality of third bottom points, extracting a plurality of second inflection points by extracting, for each of the plurality of fourth top points, a second inflection point that is an inflection point between the fourth top point and a fourth bottom point that immediately follows, in a time sequence, the fourth top point among the plurality of fourth bottom points, calculating, as the third heartbeat time interval, for each of the plurality of extracted first inflection points, a time interval between a ninth time point of the first inflection point and a tenth time point of another first inflection point adjacent to the first inflection point, calculating, as the fourth heartbeat time interval, for each of the plurality of extracted second inflection points, a time interval between an eleventh time point of the second inflection point and a twelfth time point of another second inflection point adjacent to the second inflection point, and computing, as the second correlation coefficient, a correlation coefficient between (i) the plurality of third heartbeat time intervals, calculated by using the first inflection points, and (ii) the plurality of fourth heartbeat time intervals, calculated by using the second inflection points interval, that correspond to each other in a time sequence by using the equation 2.

9. The pulse wave measuring device according to claim 5, wherein in a case where an absolute error between the third heartbeat time interval and the fourth heartbeat time interval that correspond to each other in a time sequence among the third heartbeat time intervals and the fourth heartbeat time intervals is larger than a third threshold value, the processor further directs processes to be performed including:

comparing the number of third peak points and the number of fourth peak points, specifying which of the third heartbeat time interval and the fourth heartbeat time interval for which the absolute error is larger than the third threshold value is a heartbeat time interval computed by a peak point included in peak points that have been determined to be smaller in number as a result of the comparing, and excluding the peak point used for computation of the specified heartbeat time interval from computation of the specified heartbeat time interval.

10. The pulse wave measuring device according to claim 5, wherein
the processor further directs processes to be performed including:
comparing the number of third peak points and the number of fourth peak points, and
specifying which of the plurality of third heartbeat time intervals and the plurality of fourth heartbeat time intervals are heartbeat time intervals computed by peak points that have been determined to be smaller in number as a result of the comparing; and
in a case where a standard deviation of the specified heartbeat time intervals is equal to or smaller than the fourth threshold value, the processor directs processes to be performed including:
extracting a plurality of first inflection points by extracting, for each of the plurality of third top points, a first inflection point that is an inflection point between the third top point and a third bottom point that immediately follows, in a time sequence, the third top point among the plurality of third bottom points,
extracting a plurality of second inflection points by extracting, for each of the plurality of fourth top points, a second inflection point that is an inflection point between the fourth top point and a fourth bottom point that immediately follows, in a time sequence, the fourth top point among the plurality of fourth bottom points,
calculating, as the third heartbeat time interval, for each of the plurality of extracted first inflection points, a time interval between a thirteenth time point of the first inflection point and a fourteenth time point of another first inflection point adjacent to the first inflection point,
calculating, as the fourth heartbeat time interval, for each of the plurality of extracted second inflection points, a time interval between a fifteenth time point of the second inflection point and a sixteenth time point of another second inflection point adjacent to the second inflection point, and
calculating, as the second correlation coefficient, a correlation coefficient between (i) the plurality of third heartbeat time intervals, calculated by using the first inflection points, and (ii) the plurality of fourth heartbeat time intervals, calculated by using the second inflection points, that correspond to each other in a time sequence by using the equation 2.

11. The pulse wave measuring device according to claim 5, wherein
in the extracting the plurality of first peak points, the processor directs the extracting of the plurality of first peak points from the first visible light wave acquired during a period other than a period in which the light amount of the visible light source is controlled by the first control signal;
in the extracting the plurality of second peak points, the processor directs the extracting of the plurality of second peak points from the first infrared light wave acquired during a period other than a period in which the light amount of the infrared light source is controlled by the second control signal;
in the extracting the plurality of third peak points, the processor directs the extracting of the plurality of third peak points from the second visible light wave acquired during a period other than a period in which the light amount of the visible light source is controlled by the third control signal; and
in the extracting the plurality of fourth peak points, the processor directs the extracting of the plurality of fourth peak points from the second infrared light wave acquired during a period other than a period in which the light amount of the infrared light source is controlled by the fourth control signal.

12. The pulse wave measuring device according to claim 5, wherein
in the supplying the first control signal or the third control signal, the processor directs the suspension of supply of the first control signal or the third control signal until successive two or more first peak points are extracted within a second predetermined period from the first visible light wave or until successive two or more third peak points are extracted within the second predetermined period from the second visible light wave; and
in the supplying the second control signal or the fourth control signal, the processor directs the suspension of supply of the second control signal or the fourth control signal until successive two or more second peak points are extracted within the second predetermined period from the first infrared light wave or until successive two or more fourth peak points are extracted within the second predetermined period from the second infrared light wave.

13. A pulse wave measuring method executed by a pulse wave measuring device including a processor and a memory, wherein the processor directs processes to be performed, comprising:
acquiring a first visible light image, in a visible light wavelength range, of a user irradiated with visible light by a visible light source;
acquiring a first infrared light image, in an infrared light wavelength range, of the user irradiated with infrared light by an infrared light source;
extracting a first visible light wave that is a wave indicative of a pulse wave of the user from the acquired first visible light image;
extracting a first infrared light wave that is a wave indicative of a pulse wave of the user from the acquired first infrared light image;
computing a first correlation value between the extracted first visible light wave and the extracted first infrared light wave;
performing a first determining process for determining whether or not the computed first correlation value is equal to or larger than a second threshold value;
supplying a first control signal for decreasing a light amount of the visible light emitted from the visible light source to the visible light source and supplying a second control signal for increasing a light amount of the infrared light emitted from the infrared light source to the infrared light source in a case where the processor determines, as a result of the first determining process, that the computed first correlation value is equal to or larger than the second threshold value;
acquiring a second visible light image, in the visible light wavelength range, of the user irradiated with visible light based on the first control signal by the visible light source;
acquiring a second infrared light image, in the infrared light wavelength range, of the user irradiated with infrared light based on the second control signal by the infrared light source;
extracting a second visible light wave that is a wave indicative of a pulse wave of the user from the acquired second visible light image;

extracting a second infrared light wave that is a wave indicative of a pulse wave of the user from the acquired second infrared light image;

calculating heart rate information by using at least one of the extracted second visible light wave and second infrared light wave; and outputting the calculated heart rate information.

14. A non-volatile computer-readable recording medium storing a control program for causing a device including a processor to direct processes to be executed including:

acquiring a first visible light image, in a visible light wavelength range, of a user irradiated with visible light by a visible light source, acquiring a first infrared light image, in an infrared light wavelength range, of the user irradiated with infrared light by an infrared light source, extracting a first visible light wave that is a wave indicative of a pulse wave of the user from the acquired first visible light image, extracting a first infrared light wave that is a wave indicative of a pulse wave of the user from the acquired first infrared light image, computing a first correlation value between the extracted first visible light wave and the extracted first infrared light wave, performing a first determining process for determining whether or not the computed first correlation value is equal to or larger than a second threshold value, supplying a first control signal for decreasing a light amount of the visible light emitted from the visible light source to the visible light source and supplying a second control signal for increasing a light amount of the infrared light emitted from the infrared light source to the infrared light source in a case where the processor determines, as a result of the first determining process, that the computed first correlation value is equal to or larger than the second threshold value, acquiring a second visible light image, in the visible light wavelength range, of the user irradiated with visible light based on the first control signal by the visible light source, acquiring a second infrared light image, in the infrared light wavelength range, of the user irradiated with infrared light based on the second control signal by the infrared light source, extracting a second visible light wave that is a wave indicative of a pulse wave of the user from the acquired second visible light image, extracting a second infrared light wave that is a wave indicative of a pulse wave of the user from the acquired second infrared light image, calculating heart rate information by using at least one of the extracted second visible light wave and second infrared light wave, and outputting the calculated heart rate information.

15. A pulse wave measuring method, comprising:

acquiring first visible light images, in a visible light wavelength range, of a user irradiated with first visible light by a visible light source;

acquiring first infrared light images, in an infrared light wavelength range, of the user irradiated with first infrared light by an infrared light source;

extracting a first visible light wave from the first visible light images;

extracting a first infrared light wave from the first infrared light images;

computing a correlation value between the first visible light wave and the first infrared light wave;

causing, when the correlation value is equal to or larger than a threshold value, (i) the visible light source to emit second visible light, an amount per unit time of the second visible light being smaller than an amount per unit time of the first visible light and (ii) the infrared light source to emit second infrared light, an amount per unit time of the second infrared light being larger than an amount per unit time of the first infrared light;

acquiring second visible light images, in the visible light wavelength range, of the user irradiated with the second visible light;

acquiring second infrared light images, in the infrared light wavelength range, of the user irradiated with the second infrared light;

extracting a second visible light wave from the second visible light images;

extracting a second infrared light wave from the second infrared light images;

calculating heart rate information by using at least one of the second visible light wave and the second infrared light wave; and outputting the heart rate information, wherein the computation of the correlation value includes:

extracting first peak points at first times included in first unit waves, the first peak points being either first maximum points included in the first unit waves or first minimum points included in the first unit waves, the first visible light wave including the first unit waves, the first maximum points corresponding to the first unit waves, respectively, the first minimum points corresponding to the first unit waves, respectively, and the first unit waves corresponding to the first times, respectively, extracting second peak points at second times included in second unit waves, the second peak points being either second maximum points included in the second unit waves or second minimum points included in the second unit waves, the first infrared light wave including the second unit waves, the second maximum points corresponding to the second unit waves, respectively, the second minimum points corresponding to the second unit waves, respectively, and the second unit waves corresponding to the second times, respectively, calculating first heartbeat time periods on a basis of the first times, each of the first heartbeat time periods being a time period between a first time and a second time, the first time and the second time being included in the first times, none of times included in the first times being provided between the first time and the second time, calculating second heartbeat time periods on a basis of the second times, each of the second heartbeat time periods being a time period between a third time and a fourth time, the third time and the fourth time being included in the second times, none of times included in the second times being provided between the third time and the fourth time, and calculating the correlation value using an equation:

$$\rho 1 = \frac{\sigma_{12}}{\sigma_1 \sigma_2}$$

where $\rho 1$ is the correlation value, $\sigma_{12}$ is a covariance of the first heartbeat time periods and the second heartbeat time periods, $\sigma 1$ is a first standard deviation that is a standard deviation of the first heartbeat time periods, and $\sigma 2$ is a second standard deviation that is a standard deviation of the second heartbeat time periods.

* * * * *